US007279548B2

(12) United States Patent
Pirozzi et al.

(10) Patent No.: US 7,279,548 B2
(45) Date of Patent: *Oct. 9, 2007

(54) IDENTIFICATION AND ISOLATION OF NOVEL POLYPEPTIDES HAVING WW DOMAINS AND METHODS OF USING SAME

(75) Inventors: Gregorio Pirozzi, East Windsor, NJ (US); Brian K. Kay, Madison, WI (US); Dana M. Fowlkes, Chapel Hill, NC (US)

(73) Assignees: Cytogen Corporation, Princeton, NJ (US); The University of North Carolina at Chapel Hill, Chapel Hill, NC (US)

( * ) Notice: Subject to any disclaimer, the term of this patent is extended or adjusted under 35 U.S.C. 154(b) by 657 days.

This patent is subject to a terminal disclaimer.

(21) Appl. No.: 10/185,050

(22) Filed: Jun. 28, 2002

(65) Prior Publication Data
US 2003/0077577 A1    Apr. 24, 2003

Related U.S. Application Data

(63) Continuation of application No. 08/826,516, filed on Apr. 3, 1997, now abandoned, which is a continuation-in-part of application No. 08/630,916, filed on Apr. 3, 1996, now Pat. No. 6,011,137.

(51) Int. Cl.
C07K 14/00     (2006.01)
C12P 21/04     (2006.01)
(52) U.S. Cl. .................... 530/324; 530/350; 435/69.7; 435/810
(58) Field of Classification Search .................... None
See application file for complete search history.

(56) References Cited

U.S. PATENT DOCUMENTS

| 5,096,815 | A |   | 3/1992 | Ladner et al. | ............. 435/69.1 |
|---|---|---|---|---|---|
| 5,198,346 | A |   | 3/1993 | Ladner et al. | ............. 435/69.1 |
| 5,223,409 | A |   | 6/1993 | Ladner et al. | ............. 435/69.7 |
| 6,011,137 | A | * | 1/2000 | Pirozzi et al. | ............. 530/324 |
| 6,022,740 | A |   | 2/2000 | Sudol et al. |   |

FOREIGN PATENT DOCUMENTS

| WO | WO94/18318 | 8/1994 |
|---|---|---|
| WO | WO95/24419 | 9/1995 |

OTHER PUBLICATIONS

C. Baglioni, 1992, "Mechanisms of cytotoxicity, cytolysis, and growth stimulation by TNF" in *Tumor Necrosis Factors*, pp. 425-438, (B. Beutler, ed.) Raven Press, New York.
Bock et al., 1992, "Selection of single-stranded DNA molecules that bind and inhibit human thrombin", *Nature* 355:564-566.
Chen et al., 1993, "Biased combinatorial libraries: Novel ligands for the SH3 domain of phosphatidylinositol 3-kinase", *J. Am. Chem. Soc.* 115:12591-12592.
Chen & Sudol, 1995, "WW domain of Yes-associated protein binds a proline-rich ligand that differs from the consensus established for Src homology 3-binding modules", *Proc. Natl. Acad. Sci. USA* 92:7819-7823.
Chien et al., 1991, "The two-hybrid system: A method to identify and clone genes for proteins that interact with a protein of interest", *Proc. Natl. Sci. USA* 88:9578-9582.
Chinnaiyan et al., 1995, "FADD, a novel death domain-containing protein, interacts with the death domain of Fas and initiates apoptosis", *Cell* 81:505-512.
Cho et al., 1992, "The rat brain postsynaptic density fraction contains a homolog of the Drosophilla discs-large tumor suppressor protein", *Neuron* 9:929-942.
Cicchetti et al., 1992, "Identification of a protein that binds to the SH3 region of AbI and is similar to Bcr and GAP-rho", *Science* 257:803-806.
A. Ciechanover, 1994, "The ubiquitin-proteasome proteolytic pathway", *Cell* 79:13-21.
Cohen et al., 1995, "Modular binding domains in signal transduction proteins", *Cell* 80:237-248.
Davletov & Südhof, 1993, "A single $C_2$ domain from synaptotagmin I is sufficient for high affinity $Ca^{2+}$/phospholipid binding", *J. Biol. Chem.* 268:26386-26390.
Eisenmann et al., 1992, "SPT3 interacts with TFIID to allow normal transcription in *Saccharomyces cerevisiae*", *Genes & Dev.* 6:1319-1331.
Ellington & Szostak, 1992, "Selection *in vitro* single-stranded DNA molecules that fold into specific ligand-binding structures", *Nature* 355:850-852.
Feng et al., 1994, "Two binding orientations for peptides to the Src SH3 domain: Development of a general model for SH3-ligand interactions", *Science* 266:1241-1247.
Fields & Song, 1989, "A novel genetic system to detect protein-protein interactions", *Nature* 340:245-246.
Fowlkes et al., 1992, "Multipurpose vectors for peptide expression on the M13 viral surface", *Bio Techniques* 13:422-427.
Gibson et al., 1994, "PH domain: The first anniversary", *Trends Biochem. Sci.* 19:349-353.
Hanes et al., 1989, "Sequence and mutational analysis of ESS1, a gene essential for growth in *Saccharomyces cerevisiae*", *Yeast* 5:55-72.
Haslam et al., 1993, "Pleckstrin domain homology", *Nature* 363:309-310.

(Continued)

*Primary Examiner*—Jon Weber
*Assistant Examiner*—Anand U. Desai
(74) *Attorney, Agent, or Firm*—Morgan, Lewis & Bockius LLP

(57) ABSTRACT

Novel polypeptides having WW domains of interest are described, along with DNA sequences that encode the same. A method of identifying these polypeptides by means of a sequence-independent (that is, independent of the primary sequence of the polypeptide sought), recognition unit-based functional screen is also disclosed. Various applications of the method and of the polypeptides identified are described, including their use in assay kits for drug discovery, modification, and refinement.

20 Claims, 34 Drawing Sheets

OTHER PUBLICATIONS

Hein et al., 1995, "NPI1, an essential yeast gene involved in induced degradation of Gap 1 and Fur4 permeases, encodes the Rsp5 ubiquitin-protein ligase", *Mol. Microbiol.* 18:77-87.

Hicke & Riezman, 1996, "Ubiquitination of a yeast plasma membrane receptor signals its ligand-stimulated endocytosis", *Cell* 84:277-287.

Hofmann & Bucher, 1995, "The rsp5-domain is shared by proteins of diverse functions", *FEBS Lett.* 358:153-157.

Hsu et al., 1995, "The TNF receptor 1-associated protein TRADD signals cell death and NF-kB activation", *Cell* 81:495-504.

Huibregtse et al., 1995, "A family of proteins structurally and functionally related to the E6-AP ubiquitin-protein ligase", *Proc. Natl. Sci. USA* 92:2563-2567.

Itoh et al., 1991, "The polypeptide encoded by the cDNA for human cell surface antigen Fas can mediate apoptosis", *Cell* 66:233-243.

Itoh & Nagata, 1993, "A novel protein domain required for apoptosis", *J. Biol. Chem.* 268:10932-10937.

Kaibuchi et al., 1989, "Molecular genetic analysis of the regulatory and catalytic domains of protein kinase C", *J. Biol. Chem.* 264:13489-13496.

Kay et al., 1993, "An M13 phage library displaying random 38-amino-acid peptides as a source of novel sequences with affinity to selected targets", *Gene* 128:59-65.

Koch et al., 1991, "SH2 and SH3 domains: Elements that control interactions of cytoplasmic signaling proteins", *Science* 252:668-674.

Kumar et al., 1992, "Identification of a set of genes with developmentally down-regulated expression in the mouse brain", *Biochem. Biophys. Res. Comm.* 185:1155-1161.

Iwabuchi et al., 1994, "Two cellular proteins that bind to wild-type but not mutant p53", *Proc. Natl. Acad. Sci. USA* 91:6098-6102.

Lehto et al., 1988, "Transforming and membrane proteins", *Nature* 334:388.

Lloyd et al., 1996, "A common molecular basis for three inherited kidney stone diseases", *Nature* 379:445-449.

Mayer et al., 1988, "A novel viral oncogene with structural similarity to phospholipase C", *Nature* 332:272-275.

Mayer et al., 1993, "A putative modular domain present in diverse signaling proteins", *Cell* 73:629-630.

Mori et al., 1992, "Ligand-induced polyubiquitination of the platelet-derived growth factor beta-receptor", *J. Biol. Chem.* 267:6429-6434.

Nuber et al., 1996, "Cloning of human ubiquitin-conjugating enzymes UbcH6 and UbcH7 (E2-F1) and characterization on their interaction with E6-AP and RSP5", *J. Biol. Chem.* 271:2795-2800.

Oldenburg et al., 1992, "Peptide ligands for a sugar-binding protein isolated from a random peptide library", *Proc. Natl. Acad. Sci. USA* 89:5393-5397.

Parmley & Smith, 1988, "Antibody-selectable filamentous fd phage vectors: Affinity purification of target genes", *Gene* 73:305-318.

Parmlay & Smith, 1989, "Filamentous fusion phage cloning vectors for the study of epitopes and design of vaccines", *Adv. Exp. Med. Biol.* 251:215-218.

T. Pawson, 1995, "Protein modules and signalling networks", *Nature* 373:573-580.

Pawson & Gish, 1992, "SH2 and SH3 domains: From structure to funciton", *Cell* 71:359-362.

Rodaway et al., 1989, "Similarity in membrane proteins", *Nature* 342:624.

Rebar & Pabo, 1994, "Zinc finger phage: Affinity selection of finger with new DNA-binding specificities", *Science* 263:671-673.

Ren et al., 1993, "Identification of a ten-amino acid proline-rich SH3 binding site", *Science* 259:1157-1161.

Ruff et al., 1991, "Molecular identification of a major palmitoylated erythrocyte membrane protein containing the src homology 3 motif", *Proc. Natl. Acad. Sci USA* 88:6595-6599.

Scheffner et al., 1993, "The HPV-16 E6 and E6-AP complex functions as a ubiquitin-protein ligase in the ubiquitinationa of p53", *Cell* 76:495-505.

Scott & Smith, 1990, "Searching for peptide ligands with an epitope library", *Science* 249:386-390.

Shimkets et al., 1994, "Liddle's syndrome: Heritable human hypertension caused by mutations in the beta-subunit of the epithelial sodium channel", *Cell* 79:407-414.

Sparks et al., 1994, "Identification and characterization of Src SH3 ligands from phage-displayed random peptide libraries", *J. Biol. Chem.* 269:23853-23856.

Sparks et al., 1996, "Distinct ligands perferences of Src homology 3 domains from Src, Yes, Abl, Cortactin, p53bp2, PlCr, Crk, and Grb2", *Proc. Natl. Acad. Sci USA* 93:1540-1544.

Stahl et al., 1988, "Sequence similarity of phospholipase C with the non-catalytic region of src", *Nature* 332:269-272.

Stanger et al., 1995, "RIP: A novel protein containing a death domain that interacts with Fas/APO-1 (CD95) in yeast and causes cell death", *Cell* 81:513-523.

Staudt et al., 1988, "Cloning of a lymphoid specific cDNA encoding a protein binding the regulatory octamer DNA motif", *Science* 241:577-580.

M. Sudol, 1994, "Yes-associated protein (YAP65) is a proline-rich phosphoprotein that binds to the SH3 domain of the Yes proto-oncogene product", *Oncogene* 9:2145-2152.

Sudol et al., 1995, "Characterization of the mammalian YAP (yes-associated protein) and its role in defining a novel protein module, the WW domain", *J. Biol. Chem.* 270:14733-14741.

Sugita et al., 1990, "Functional murine interleukin 6 receptor with the intracisternal A particle gene product at its cytoplasmic domain: Its possible role in plasmacytomagenesis", *J. Exp. Med.* 171:2001-2009.

Sutton et al., 1995, "Structure of the first $C_2$ domain of synaptotagmin I: A novel $Ca^{2+}$/phospholipid-binding fold", *Cell* 80:929-938.

Tartaglia et al., 1993, "A novel domain within the 55 kd TNF receptor signals cell death", *Cell* 74:845-853.

Trahey et al., 1988, "Molecular cloning of two types of GAP complementary DNA from human placenta", *Science* 242:1697-1700.

Tuerk et al., 1992, "RNA pseudoknots that inhibit human Immunodeficiency virus type 1 reverse transcriptase", *Proc. Natl. Acad. Sci. USA* 89:6988-6992.

Williams et al., 1988, "Cloning and expression of AP-2, a cell-type-specific transcription factor that activates inducible enhancer elements", *Genes & Dev.* 2:1557-1569.

Yu et al., 1994, "Structural basis for the binding of proline-rich peptides to SH3 domains", *Cell* 76:933-945.

Lazar et al., Molecular and Cellular Biology 8:1247-1252, 1988.

Burgess et al., The Journal of Cell Biology 111:2129-2138, 1990.

M. Sudol et al., FEBS Letters, 369 67-71 (1995).

U. Nuber et al., J. Biol. Chem., 271 2795-2800 (1996).

International Search Report for PCT/US97/05547, mailed Aug. 14, 1997.

Cheadle et al., 1994, "Identification of a Src SH3 Domain Binding Motif by Screening a Random Phage Display Library", J. Biol. Chemistry 269:24034-24039.

Andre et al. "WWP, a new amino acid motif present in single or multiple copies in various proteins including dystrophin and the SH3-binding Yes-associated protein YAP65" Biochemical and Biophysical research Communications. vol. 205, pp. 1201-1205.

Bork et al. "The WW domain: a signaling site in dystrophin?" Trends in Biochemical Sciences. vol. 19. No. 12, pp. 531-533.

* cited by examiner

| GENE/SPECIES | POS. | WW DOMAIN SEQUENCES | ACC. NO. | SEQ. ID NO. |
|---|---|---|---|---|
| WWP1-1 | ? | LPSGWGWEQRKDPHGRTYYVDHNTRTTTWERPQPLPPG | | 30 |
| WWP1-2 | ? | QPLPPGWERRVDDRRRVYYVDHNTRTTTWQRPTMESVR | | 131 |
| WWP1-3 | ? | GPLPPGWEKRVDSTDRVYFVNHNTKTTQWEDPRTQGLQ | | 32 |
| WWP1-4 | ? | EPLPEGWEIRYTREGVRYFVDHNTRTTTFKDPRNGKSS | | 33 |
| WWP2-1 | ? | DALPAGWEQRELPNGRVYYVDHNTKTTTWERPLPPGWE | | 34 |
| WWP2-2 | ? | RPLPPGWEKRTDPRGRFYYVDHNTRTTTWQRPTAEYVR | | 35 |
| WWP2-3 | ? | GPLPPGWEKRQD.NGRVYYVNHNTRTTQWEDPRTQGMI | | 36 |
| WWP2-4 | ? | PALPPGWEMKYTSEGVRYFVDHNTRTTTFKDPRPGFES | | 37 |
| WWP3 | ? | GPLPENWEMAYTENGEVYFIDHNTKTTSWLDPRCLNKO | | 38 |
| WWP4-1 | ? | PGLPSGWEERKDAKGRTYYVNHNNRTTTWTRPIMQLAE | | 132 |
| WWP4-2 | ? | SFLPPGWEMRIAPNGRPFFIDHNTKTTTWEDPRLKFPV | | 133 |
| WWP4-3 | ? | GPLPPGWEERIHLDGRTFYIDHNSKITQWEDPRLQNPA | | 134 |
| Yap/HUMAN | 171 | VPLPAGWEMAKTSSGQRYFLNHIDQTTTWQDPRKAMLS | X80507 | 12 |
| Yap/MOUSE-1 | 151 | VPLPAGWEMAKTSSGQRYFLNHNDQTTTWQDPRKAMLS | X80508 | 15 |
| Yap/CHICK-1 | 169 | VPLPPGWEMAKTPSGQRYFLNHIDQTTTWQDPRKAMLS | X76483 | 13 |
| Yap/CHICK-2 | 229 | GPLPDGWEQAMTQDGEIYYINHKNKTTSWLDPRLDPRF | X76483 | 14 |
| Yap/MOUSE-2 | 218 | GPLPDGWEQAMTQDGEVYYINHKNKTTSWLDPRLDPRF | X80508 | 16 |
| Ned4/HUMAN-1 | 218 | SPLPPGWEERQDILGRTYYVNHESRRTQWKRPTPQDNL | D42055 | 17 |
| Ned4/MOUSE-1 | ? | SPLPPGWEERQDVLGRTYYVNHESRRTQWKRPSPDDDL | D10714 | 18 |
| Rsp5/YEAST-1 | 228 | GRLPPGWERRTDNFGRTYYVDHNTRTTTWKRPTLDQTE | L11119 | 19 |
| Ned4/HUMAN-2 | 375 | SGLPPGWEEKQDERGRSYYVDHNSRTTTWTKPTVQATV | D42055 | 21 |
| Ned4/MOUSE-2 | ? | SGLPPGWEEKQDDRGRSYYVDHNSKTTTWSKPTMQDDP | D10714 | 20 |
| Rsp5/YEAST-2 | 331 | GELPSGWEQRFTPEGRAYFVDHNTRTTTWVDPRRQQYI | L11119 | 22 |
| Ned4/HUMAN-3 | 448 | GFLPKGWEVRHAPNGRPFFIDHNTKTTTWEDPRLKIPA | D42055 | 23 |
| NED4/MOUSE-3 | ? | GPLPPGWEERTHTDGRVFFINHNIKKTQWEDPRLQNVA | D10714 | 24 |
| Rsp5/YEAST-3 | 387 | GPLPSGWEMRLTNTARVYFVDHNTKTTTWDDPRLPSSL | L11119 | 26 |
| Ned4/HUMAN-4 | 500 | GPLPPGWEERTHTDGRIFYINHNIKRTQWEDPRLENVA | D42055 | 25 |
| Dmd_HUMAN | 3052 | TSVQGPWERAISPNKVPYYINHETQTTCWDHPKMTELY | P11532 | 27 |
| Dmd/Torca | 253 | TSVQGPWERAISPNKVPYYMNHQTQTTCWDHPKMTELY | M37645 | 28 |
| Utro/HUMAN | 2813 | TSVQLPWQRSISHNKVPYYINHQTQTTCWDHPKMTELF | X69086 | 29 |
| CONSENSUS | | LPtGWEXXXttGtXYYhXHNTtTTtWXtPt | | |

FIG.5

| | | | | WW DOMAIN CLONES | | |
|---|---|---|---|---|---|---|
| PEPTIDE | NAME | SEQUENCE | SEQ. ID NO. | WWP1 | WWP2 | WWP3 |
| SH3001 | WBP-1 | PGTPPPPYTVGPGY | 85 | +++ | +++ | +++ | - |
| TPPY | WBP-1 | HGPTPPPPYTVGP | 86 | +++ | ++ | ++ | - |
| QPPY | WBP-2 | YVQPPPPPYPGPM | 87 | +++ | +++ | +++ | ++ |
| YPPE | WBP-2 | PGYPYPPPEFY | 88 | - | - | - | - |
| WW005 | WBP-1 | PGTPAPPYTVGPGY | 89 | +++ | +++ | +++ | - |
| WW006 | WBP-1 | PGTPPAPYTVGPGY | 90 | - | - | - | - |
| bSH3002 | K+ CHANNEL | DSGVRPLPPLPDPGV | 91 | - | - | - | - |
| bSH3003 | K+ CHANNEL | VRPLPPLPEELPRPRRPPPED | 92 | - | - | - | - |
| bSH3004 | M4 AChr | PPPALPPPPRPVADK | 93 | - | - | - | - |
| bSH3005 | β1 ADRENERGIE | APAPPPGPPRPAAAA | 94 | - | - | - | - |
| bSH3006 | RasGap | GGGPPPLPPPPYLPPLG | 95 | ++ | ++ | ++ | - |
| bsH3007 | MEK | SISPRPRPPGRPVSG | 96 | - | - | - | - |
| bSH3008 | P Tyr PHOSP. | PPPEHIPPPPPKRILE | 97 | - | - | - | - |
| bSH3009 | Fak | KEGERALPSIPKLAN | 98 | - | - | - | - |
| bSH3010 | c-Abl | SRLKPAPPPPAASAG | 99 | - | - | - | - |
| bSH3011 | c-Cbl | QASLPPVPPRDLLLP | 100 | - | - | - | - |
| bSH3012 | c-Cbl | PVPPTLRDLPPPPPPDRPYS | 101 | - | - | - | - |
| bSH3013 | Ca2+ CHANNEL | SDQGRNLPGTPVPAS | 102 | - | - | - | - |
| bSH3014 | Ca2+ CHANNEL | RHSRRQLPPVPPKPRPLL | 103 | - | - | - | - |
| bSH3015 | Nef | EKVGFPVTPQVPLRPMTY | 104 | - | - | - | - |
| bSH3016 | Mus CADHERIN | PQPHRVLPTSPDIA | 105 | - | - | - | - |
| bSH3017 | AP2 | ADFQPPYFPPPYQPTYPQS | 106 | ++ | ++ | ++ | - |
| bSH3018 | ACTIN BINDING | SSAAPPPPPRRATPEK | 107 | - | - | - | - |
| bSH3019 | EZRIN | SKKGVMTAPPPPPPPVYEPGG | 108 | - | - | - | - |
| bSH3020 | VINCULIN | EAFQPQEPDFPPPPPDLE | 109 | - | - | - | - |
| bSH3021 | VINCULIN | DELAPPKPPLPEGEVPPPRPPPPE | 110 | - | - | - | - |
| bSH3022 | DYNAMIN | PQRRAPAVPPARPGSR | 111 | - | - | - | - |
| bSH3023 | DYNAMIN | LGGAPPVPSRPGASPDG | 112 | - | - | - | - |
| NUMBER OF DOMAINS ENCODED BY CLONE | | | | 4 | 4 | 4 | 1 |

| GENE | HECT DOMAIN SEQUENCE | SEQ ID NO. |
|---|---|---|
| | *-100 | |
| WWP1: | YR-HYTRNSKQ---IIWFWQFVKETDNEVRMRLLQFWTGTCRLPGGFAELMGSN | 115 |
| WWP2: | YR-HYTKNSKQ---IQWFWQVVKEMDNEKRIRLLQFVTGTCRLPVGGFAELIGSN | 116 |
| RSP5: | YR-GYQESDEV---IQWFWKCVSEWDNEQRARLLQFTTIGTSRIPVNGFKDLQGSD | 117 |
| NEDD-4: | FNDESGENAEKLL-IHWFWKAVWMDSEKRIRLLQFVTGTSRVPMNGFAELYGSN | 118 |
| E6-AP: | YDGGYTRDSVL---IREFWEIVHSFTDEQRRLFLQFTTIGTDRAPVGGLGRL--- | 119 |
| RAT p100: | YKGDYSATHPT-QFKRWFWSIVERMSMTERQDLVYFWTSSPSLPASEEGFQPM-- | 120 |
| D13635: | YSGGYSADHPV---IRVEWRVVFGFTDEEKRKLLKFVTSCSRPPLLGFKELYP--- | 121 |
| D25215: | PDHGYTHDSRAVK-VRLFWETFHEFPLEKKRKFLLFLTGSDRIPIYGMASL---- | 122 |
| D28476: | AEHGYTMDSSI----FLF-EILSSFDNEQQRLFLQFVTGSPRLPVGGFRSLNPPL | 123 |
| DROS.HYD: | FNDESSEGPDKLKFKRWFWSIVEKMNIMERQHLVYFWTGSPALPASEEGFQPL-- | 70 |
| YKL162 | YKNGYSMNHQV---IHDFISIISAFGKHERRLFLQFLTGSPRLPIGGFKSLNPKF | 71 |
| ScORF: | YVGGFSDDSRA----VCWFWEIIESWDYPLQRKLLQFVTASDRIPATGISTI--- | 72 |
| UreB1: | Y-HKYQSNSIQ---IQWFWRALRSFDQADRAKFLQFVGTSRVPLQGFAALEGMN | 73 |
| | -50 | |
| WWP2: | GPQKFCID-KVGKETWPRSHTCFNRLDLPPYKSYEQLREKLLYAI-EETEGFGQE | 124 |
| RSP5: | GPRRFTIE-KAGEVQQLPKSHTCFNRVDLPQYVDYDSMRQRLTLAV-EETIGFGQE | 74 |
| NEDD-4: | GPQSFTVE-QWGTPDRLPRAHTCFNRLDLPPYESFDELWDRLQMAI-ENTQGFDHVD | 75 |
| E6-AP: | ---KMIIAKNGPDTERLPTSHTCFNVLLPEYSSKEKLRERLLKAIT-YARGFGML | 76 |
| RAT p100: | ---PSITIRPPDDQH-PTANTCISRLYVPLYSSRQILRQRLLLAIK--TRNFGFV | 77 |
| D13635: | ---AFCIHNGGSDLERLPTASTQMNLLKLPEFYDETLLRSRLLYAI-ECAAGEELS | 78 |
| D25215: | ---PSITIQSTASGEEYLPVAHTCYNLLDLPKYSSREILSARLTQAL-DNYEGESLA | 79 |
| D28476: | ---PSVTI--RPADDSHLPTAHTCYNYLKLPDYSSIEIMRERLLIAAREGQQSFHLS | 80 |
| Dros.HYD | ---QIVIESTENPDDFLPSVMTCVNYLKLPKYTSRDIMRSRLCQAIEEGAGAFLLS | 81 |
| YKL162 | TIVRKTFEDGLTADEYLPSVMTCANYLKLPKYTSRDIMRSRLCQAIEEGAGAFLLS | 82 |
| ScORF: | ---PFKISLLGSHDSDDLPLAHTCFNEICLWNYSSRKRLELRLLWAI-NESEGYGFR | 83 |
| UreB1: | GIQKFQIHRDDRSTDRLPSAHTCFNQLDLPAYESFEKLRHMLLLAIQECSEGFGLANK | 84 |

FIG. 15A

| PEPTIDE | SEQUENCE | SEQ. ID NO. | WWP1.1 | WWP1.2 | WWP1.3 | WWP1.4 | WWP2.1 | WWP2.2 | WWP2.3 | WWP2.4 | WWP3 | Fyn | Lyn |
|---|---|---|---|---|---|---|---|---|---|---|---|---|---|
| WBP-1 | PGTPPPPYTVGPGY | 85 | +++ | - | ++ | - | ++ | - | - | - | - | - | - |
| WBP-2A | YVQPPPPYPGPM | 8 | +++ | + | +++ | - | +++ | - | +++ | +++ | ++++ | - | - |
| WBP-2B | PGYPYPPPEFY | 7 | - | - | - | - | - | - | - | - | - | - | - |
| WBP-2C | TSQPPPPYYPP | 135 | +++ | - | +++ | - | +++ | - | +++ | ++++ | - | - | - |
| WBP-1-Pro1 | PGTAPPPYTVGPGY | 53 | +++ | - | - | - | - | - | +++ | - | - | - | - |
| WBP-1-Pro2 | PGTPPAPYTVGPGY | 89 | ++ | + | +++ | - | +++ | - | + | - | - | - | - |
| WBP-1-Pro3 | PGTPPAPYTVGPGY | 90 | - | - | - | - | - | - | - | - | - | - | - |
| WBP-1-Pro4 | PGTPPAYTVGPGY | 54 | +++ | - | +++ | - | +++ | - | - | - | - | - | - |
| WBP-2A-Pro1 | YVQAPPPYPGPM | 136 | +++ | + | +++ | - | +++ | - | +++ | ++ | +++ | - | - |
| WBP-2A-Pro2 | YVQAPPPYPGPM | 137 | +++ | - | +++ | - | +++ | - | +++ | +++ | +++ | - | - |
| WBP-2A-Pro3 | YVQPPAPYPGPM | 138 | + | - | + | - | + | - | ± | - | ± | - | - |
| WBP-2A-Pro4 | YVQPPAPYPGPM | 139 | +++ | - | +++ | - | +++ | - | ± | - | +++ | - | - |
| WBP-2A-Pro5 | YVQPPPAYPGPM | 140 | ++ | - | +++ | - | +++ | - | ++ | - | - | - | - |
| pWBP-1 | PGTPPPpYTVGPGY | 55 | - | - | - | - | - | - | - | - | - | - | - |
| RasGap | GGGFPPLPPPPYLPPLG | 95 | +++ | - | +++ | - | ++ | - | ++ | - | - | - | - |
| AP-2 | ADFQPPYFPPPYQPIYPQS | 106 | +++ | ++ | +++ | ± | +++ | +++ | ++ | - | + | - | - |
| p53BP-2 | EYPYPPPPPYPSGE | 56 | +++ | + | +++ | ± | +++ | ++ | +++ | - | +++ | - | - |
| IL-6Rα | SKTTSPPPPYSLGPLK | 57 | ± | - | - | - | ++ | - | ++ | - | - | - | - |
| CLCN5 | HSPPLPPYTPPTL | 58 | ± | - | + | - | ± | - | ± | ±± | - | - | - |
| ENaCβ | PGTPPPNYDSLRL | 59 | ± | - | - | - | ++ | - | ++ | - | - | - | - |
| ENaCβ-P616L | PGTPPLNYDSLRL | 1 | - | - | - | - | - | - | - | - | - | - | - |
| ENaCγ | PGTPPKYNTLRL | 60 | +++ | - | +++ | - | ++ | - | + | - | ± | - | - |
| FORMIN | APPTPPPLPP | 141 | - | - | - | - | ± | - | + | - | - | - | - |
| M4 A ChR | PPPALPPPPRPVADK | 61 | - | - | + | - | + | - | - | - | - | - | - |
| c-Abl | SRLKPAPPPPAASAG | 99 | - | - | - | - | - | - | - | - | - | ± | ± |
| Src | GILAPPVPPRNTR | 62 | - | - | - | - | - | - | - | - | - | ± | ± |
| Crk | SVPAPPLPPKSGG | 63 | - | - | - | - | - | - | - | - | - | + | - |

O.D UNITS SCALE (-)=0-0.5  (+)=0.5-1.0  (++)=1.0-2.0  (+++)=2.0-3.0  (++++)=>3.0

| PEPTIDE | SEQUENCE | SEQ. ID NO. | GST FUSION PROTEINS ||| 
|---|---|---|---|---|---|
| | | | WWP4.1 | WWP4.2 | WWP4.3 |
| WBP-1 | PGTPPPPYTVGPGY | 85 | +++ | ++ | + |
| WBP-2A | YVQPPPPYPGPM | 8 | +++ | +++ | +++ |
| WBP-2B | PGYPYPPPPEFY | 7 | − | − | − |
| WBP-2C | TSQPPPPYYPP | 135 | +++ | +++ | − |
| WBP-1-Pro1 | PGTAPPPYTVGPGY | 53 | +++ | +++ | + |
| WPB-1-Pro2 | PGTPPAPYTVGPGY | 89 | − | − | − |
| WBP-1-Pro3 | PGTPPAPYTVGPGY | 90 | − | − | − |
| WBP-1-Pro4 | PGTPPPAYTVGPGY | 54 | +++ | ++ | − |
| WBP-2A-Pro1 | YVQAPPPYPGPM | 136 | +++ | +++ | +++ |
| WBP-2A-Pro2 | YVQPAPPYPGPM | 137 | +++ | +++ | +++ |
| WBP-2A-Pro3 | YVQPPAPYPGPM | 138 | + | ++ | + |
| WBP-2A-Pro4 | YVQPPPAPYPGPM | 139 | − | − | − |
| WBP-2A-Pro5 | YVQPPPAYPGPM | 140 | +++ | +++ | +++ |
| pWBP-1 | PGTPPPPpYTVGPGY | 55 | − | − | − |
| RasGap | GGGFPPLPPPPYLPPLG | 95 | ++ | ++ | + |
| AP-2 | ADFQPPYFPPPYQPIYPQS | 106 | ++ | ++ | − |
| p53BP-2 | EYPPYPPPPYPSGE | 56 | +++ | +++ | ++ |
| IL-6Rα | SKTTSPPPPYSLGPLK | 57 | − | − | + |
| CLCN5 | HSPPLPPYTPPTL | 58 | − | − | − |
| FORMIN | APPTPPPLPP | 141 | − | − | − |
| M4 A ChR | PPPALPPPPRPVADK | 61 | − | − | − |
| c-Abl | SRLKPAPPPPAASAG | 99 | − | − | − |
| Src | GILAPPVPPRNTR | 62 | − | − | − |
| Crk | SVPAPPPLPPKSGG | 63 | − | − | − |

FIG.15B

| PEPTIDE | SEQUENCE | SEQ. ID NO. | GST FUSION PROTEINS | | |
|---|---|---|---|---|---|
| | | | WWP4.1 | WWP4.2 | WWP4.3 |
| IL-2R Hum | QHSPYWAPPCYTLKPET | 142 | ++ | − | − |
| IL-7R | RDGDRNRPPVYQDLLP | 143 | − | +++ | ++ |
| Dystcan-1 | EKAPLPPPEYPNQS | 144 | − | + | − |
| Dystcan-2 | MTPYRSPPPYVPP | 145 | − | + | − |
| MAPKAP2 | GVIMYILLCGYPPFYSNHGLA | 146 | − | − | − |
| PRKACG | GVLIYEMAVGFPPFYADQPIQ | 147 | − | + | − |
| LAP Hum | FRMQAQPPGYRHVAD | 148 | − | − | − |
| HTLV-1 | PDSDPQIPPPYVEPTA | 149 | − | ++ | − |
| RSV-1 | TATASAPPPPYVGSGL | 150 | + | ++ | − |
| EGR2 | HLYSPPPPPPPYSGCA | 151 | +++ | +++ | +++ |
| FIBNECT | PHPQPPPYGHCV | 152 | +++ | +++ | ++ |
| LAMININ | PRRGPPTYRADD | 153 | − | − | − |
| NTPHIN-3 | PLEPPPLYLMED | 154 | − | − | − |
| CDX BOX | PPPAPPQYPDFS | 155 | − | − | − |
| MEL. AG | PNSDPPRYQFLW | 156 | +++ | +++ | +++ |
| FU TARZAZU | PHSLPPTYYDNS | 157 | − | − | − |
| INSCUTEABLE | IAPPPPPPYNNET | 158 | − | + | − |
| WWP3.CW3 | SRGMPSYEEAVMA | 159 | − | ++ | ++ |

FIG.15C

| PEPTIDE | SEQUENCE | SEQ. ID NO. | WW DOMAIN/GST FUSION PROTEINS ||||||||| SH3 DOMAINS ||
| --- | --- | --- | --- | --- | --- | --- | --- | --- | --- | --- | --- | --- | --- |
| | | | WWP1.1 | WWP1.2 | WWP1.3 | WWP1.4 | WWP2.1 | WWP2.2 | WWP2.3 | WWP2.4 | WWP3 | Fyn | Lyn |
| Ras-Gap | GGGFPPLPPPPYLPPLG | 95 | +++ | − | +++ | − | +++ | − | +++ | − | − | − | − |
| AP-2 | ADFQPPYEPPYQPIYPQS | 106 | +++ | + | +++ | − | +++ | − | − | − | + | − | − |
| p53BP-2 | EYPPYPPPPYPSGE | 56 | +++ | +++ | +++ | ++ | ++++ | +++ | +++ | − | − | − | − |
| CLCN5 | HSPPLPPYTPPTL | 58 | ++ | +++ | + | ++ | ++ | − | − | +++ | − | − | − |
| IL-2Rγ | QHSPYWAPPCYTLKPET | 174 | + | − | − | − | − | − | ++ | − | − | − | − |
| IL-6Rα | SKTTSPPPPYSLGPLK | 57 | +++ | + | ++++ | − | +++ | ++ | +++ | − | +++ | − | − |
| β-DYSTROGLYCAN | MTPYRSPPPYVPP | 175 | + | − | + | − | − | − | ++ | − | − | − | − |
| HTLV-1 Gag | PDSDPQIPPPYVEPTA | 176 | + | − | +++ | − | ++ | − | ++ | − | − | − | − |
| RSV-1 Gag | TATASAPPPPYVGSGL | 177 | ++++ | +++ | +++ | − | +++ | − | ++ | − | +++ | − | − |
| FORMIN | APPTPPPLPP | 178 | − | − | − | − | − | − | − | − | − | − | − |

FIG.15D

```
GACTAATCATGTACCTACAAGCACTCTAGTCCAAAACTCA    40
TGCTGCTCGTATGTAGTTAATGGAGACAACACACCTTCAT    80
CTCCGTCTCAGGTTGCTGCCAGACCCAAAAATACACCAGC   120
TCCAAAACCACTCGCATCTGAGCCTGCCGATGACACTGTT   160
AATGGAGAATCATCCTCATTTGCACCAACTGATAATGCGT   200
CTGTCACGGGTACTCCAGTAGTGTCTGAAGAAAATGCCTT   240
GTCTCCAAATTGCACTAGTACTACTGTTGAAGATCCTCCA   280
GTTCAAGAAATACTGACTTCCTCAGAAAACAATGAATGTA   320
TTCCTTCTACCAGTGCAGAATTGGAATCTGAAGCTAGAAG   360
TATATTAGAGCCTGACACCTCTAATTCTAGAAGTAGTTCT   400
GCTTTTGAAGCAGCCAAATCAAGACAGCCAGATGGGTGTA   440
TGGATCCTGTACGGCAGCAGTCTGGGAATGCCAACACAGA   480
AACCTTGCCATCAGGGTGGGAACAAAGAAAAGATCCTCAT   520
GGTAGAACCTATTATGTGGATCATAATACTCGAACTACCA   560
CATGGGAGAGACCACAACCTTTACCTCCAGGTTGGGAAAG   600
AAGAGTTGATGATCGTAGAAGAGTTTATTATGTGGATCAT   640
AACACCAGAACAACAACGTGGCAGCGGCCTACCATGGAAT   680
CTGTCCGAAATTTTGAACAGTGGCAATCTCAGCGGAACCA   720
ATTGCAGGGAGCTATGCAACAGTTTAACCAACGATACCTC   760
TATTCGGCTTCAATGTTAGCTGCAGAAAATGACCCTTATG   800
GACCTTTGCCACCAGGCTGGGAAAAAGAGTGGATTCAAC   840
AGACAGGGTTTACTTTGTGAATCATAACACAAAAACAACC   880
CAGTGGGAAGATCCAAGAACTCAAGGCTTACAGAATGAAG   920
AACCCCTGCCAGAAGGCTGGGAAATTAGATATACTCGTGA   960
AGGTGTAAGGTACTTTGTTGATCATAACACAAGAACAACA  1000
ACATTCAAAGATCCTCGCAATGGGAAGTCATCTGTAACTA  1040
AAGGTGGTCCACAAATTGCTTATGAACGCGGCTTTAGGTG  1080
GAAGCTTGCTCACTTCCGTTATTTGTGCCAGTCTAATGCA  1120
CTACCTAGTCATGTAAAGATCAATGTGTCCCGGCAGACAT  1160
TGTTTGAAGATTCCTTCCAACAGATTATGGCATTAAAACC  1200
CTATGACTTGAGGAGGCGCTTATATGTAATATTTAGAGGA  1240
GAAGAAGGACTTGATTATGGTGGCCTAGCGAGAGAATGGT  1280
TTTTCTTGCTTTCACATGAAGTTTTGAACCCAATGTATTG  1320
CTTATTTGAGTATGCGGGCAAGAACAACTATTGTCTGCAG  1360
ATAAATCCAGCATCAACCATTAATCCAGACCATCTTTCAT  1400
ACTTCTGTTTCATTGGTCGTTTATTGCCATGGCACTATT   1440
TCATGGAAAGTTTATCGATACTGGTTTCTCTTTACCATTC  1480
TACAAGCGTATGTTAAGTAAAAAACTTACTATTAAGGATT  1520
TGGAATCTATTGATACTGAATTTATAACTCCCTTATCTG   1560
GATAAGAGATAACAACATTGAAGAATGTGGCTTAGAAATG  1600
TACTTTTCTGTTGACATGGAGATTTTGGGAAAAGTTACTT  1640
CACATGACCTGAAGTTGGGAGGTTCCAATATTCTGGTGAC  1680
TGAGGAGAACAAAGATGAATATATTGGTTTAATGACAGAA  1720
TGGCGTTTTTCTCGAGGAGTACAAGAACAGACCAAAGCTT  1760
```

FIG.16A

```
TCCTTGATGGTTTTAATGAAGTTGTTCCTCTTCAGTGGCT 1800
ACAGTACTTCGATGAAAAAGAATTAGAGGTTATGTTGTGT 1840
GGCATGCAGGAGGTTGACTTGGCAGATTGGCAGAGAAATA 1880
CTGTTTATCGACATTATACAAGAAACAGCAAGCAAATCAT 1920
TTGGTTTTGGCAGTTTGTGAAAGAGACAGACAATGAAGTA 1960
AGAATGCGACTATTGCAGTTCGTCACTGGAACCTGCCGTT 2000
TACCTCTAGGAGGATTTGCTGAGCTCATGGGAAGTAATGG 2040
GCCCCGGAATTC 2052 (SEQ ID NO: 45)
```

FIG.16B

```
TNHVPTSTLVQNSCCSYVVNGDNTPSSPSQVAARPKNTPA  40
PKPLASEPADDTVNGESSSFAPTDNASVTGTPVVSEENAL  80
SPNCTSTTVEDPPVQEILTSSENNECIPSTSAELESEARS  120
ILEPDTSNSRSSSAFEAAKSRQPDGCMDPVRQQSGNANTE  160
TLPSGWEQRKDPHGRTYYVDHNTRTTTWERPQPLPPGWER  200
RVDDRRRVYYVDHNTRTTTWQRPTMESVRNFEQWQSQRNQ  240
LQGAMQQFNQRYLYSASMLAAENDPYGPLPPGWEKRVDST  280
DRVYFVNHNTKTTQWEDPRTQGLQNEEPLPEGWEIRYTRE  320
GVRYFVDHNTRTTTFKDPRNGKSSVTKGGPQIAYERGFRW  360
KLAHFRYLCQSNALPSHVKINVSRQTLFEDSFQQIMALKP  400
YDLRRRLYVIFRGEEGLDYGGLAREWFFLLSHEVLNPMYC  440
LFEYAGKNNYCLQINPASTINPDHLSYFCFIGRFIAMALF  480
HGKFIDTGFSLPFYKRMLSKKLTIKDLESIDTEFYNSLIW  520
IRDNNIEECGLEMYFSVDMEILGKVTSHDLKLGGSNILVT  560
EENKDEYIGLMTEWRFSRGVQEQTKAFLDGFNEVVPLQWL  600
QYFDEKELEVMLCGMQEVDLADWQRNTVYRHYTRNSKQII  640
WFWQFVKETDNEVRMRLLQFVTGTCRLPLGGFAELMGSNG  680
PRN  683  (SEQ ID NO: 46)
```

FIG. 17

```
GAATTCGCGGCCGCGTCGACCGCTTCTGTGGCCACGGCAG    40
ATGAAACAGAAAGGCTAAAGAGGGCTGGAGTCAGGGGACT    80
TCTCTTCCACCAGCTTCACGGTGATGATATGGCATCTGCC   120
AGCTCTAGCCGGGCAGGAGTGGCCCTGCCTTTTGAGAAGT   160
CTCAGCTCACTTTGAAAGTGGTGTCCGCAAAGCCCAAGGT   200
GCATAATCGTCAACCTCGAATTAACTCCTACGTGGAGGTG   240
GCGGTGGATGGACTCCCCAGTGAGACCAAGAAGACTGGGA   280
AGCGCATTGGGAGCTCTGAGCTTCTCTGGAATGAGATCAT   320
CATTTTGAATGTCACGGCACAGAGTCATTTAGATTTAAAG   360
GTCTGGAGCTGCCATACCTTGAGAAATGAACTGCTAGGCA   400
CCGCATCTGTCAACCTCTCCAACGTCTTGAAGAACAATGG   440
GGGCAAAATGGAGAACATGCAGCTGACCCTGAACCTGCAG   480
ACGGAGAACAAAGGCAGCGTTGTCTCAGGCGGAAAACTGA   520
CAATTTTCCTGGACGGGCCAACTGTTGATCTGGGAAATGT   560
GCCTAATGGCAGTGCCCTGACAGATGGATCACAGCTGCCT   600
TCGAGAGACTCCAGTGGAACAGCAGTAGCTCCAGAGAACC   640
GGCACCAGCCCCCCAGCACAAACTGCTTTGGTGGAAGATC   680
CCGGACGCACAGACATTCGGGTGCTTCAGCCAGAACAACC   720
CCAGCAACCGGCGAGCAAAGCCCCGGTGCTCGGAGCCGGC   760
ACCGCCAGCCCGTCAAGAACTCAGGCCACAGTGGCTTGGC   800
CAATGGCACAGTGAATGATGAACCCACAACAGCCACTGAT   840
CCCGAAGAACCTTCCGTTGTTGGTGTGACGTCCCCACCTG   880
CTGCACCCTTGAGTGTGACCCCGAATCCCAACACGACTTC   920
TCTCCCTGCCCCAGCCACACCGGCTGAAGGAGAGGAACCC   960
AGCACTTCGGGTACACAGCAGCTCCCAGCGGCTGCCCAGG  1000
CCCCCGACGCTCTGCCTGCTGGATGGGAACAGCGAGAGCT  1040
GCCCAACGGACGTGTCTATTATGTTGACCACAATACCAAG  1080
ACCACCACCTGGGAGCGGCCCCTTCCTCCAGGCTGGGAAA  1120
AACGCACAGATCCCCGAGGCAGGTTTTACTATGTGGATCA  1160
CAATACTCGGACCACCACCTGGCAGCGTCCGACCGCGGAG  1200
TACGTGCGCAACTATGAGCAGTGGCAGTCGCAGCGGAATC  1240
AGCTCCAGGGGGCCATGCAGCACTTCAGCCAAAGATTCCT  1280
ATACCAGTTTTGGAGTGCTTCGACTGACCATGATCCCCTG  1320
GGCCCCCTCCCTCCTGGTTGGGAGAAAAGACAGGACAATG  1360
GACGGGTGTATTACGTGAACCATAACACTCGCACGACCCA  1400
GTGGGAGGATCCCCGGACCCAGGGGATGATCCAGGAACCA  1440
GCTTTGCCCCCAGGATGGGAGATGAAATACACCAGCGAGG  1480
GGGTGCGATACTTTGTGGACCACAATACCCGCACCACCAC  1520
CTTTAAGGATCCTCGCCCGGGGTTTGAGTCGGGGACGAAG  1560
CAAGGTTCCCCTGGTGCTTATGACCGCAGTTTTCGGTGGA  1600
AGTATCACCAGTTCCGTTTCCTCTGCCATTCAAATGCCCT  1640
ACCTAGCCACGTGAAGATCAGCGTTTCCAGGCAGACGCTT  1680
TTCGAAGATTCCTTCCAACAGATCATGAACATGAAACCCT  1720
ATGACCTGCGCCGCCGGCTTTACATCATCATGCGTGGCGA  1760
GGAGGGCCTGGACTATGGGGGCATCGCCAGAGAGTGGTTT  1800
```

FIG.18A

```
TTCCTCCTGTCTCACGAGGTGCTCAACCCTATGTATTGTT 1840
TATTTGAATATGCCGGAAAGAACAATTACTGCCTGCAGAT 1880
CAACCCCGCCTCCTCCATCAACCCGGACCACCTCACCTAC 1920
TTTCGCTTTATAGGCAGATTCATCGCCATGGCGCTGTACC 1960
ATGGAAAGTTCATCGACACGGGCTTCACCCTCCCTTTCTA 2000
CAAGCGGATGCTCAATAAGAGACCAACCCTGAAAGACCTG 2040
GAGTCCATTGACCCTGAGTTCTACAACTCCATTGTCTGGA 2080
TCAAAGAGAACAACCTGGAAGAATGTGGCCTGGAGCTGTA 2120
CTTCATCCAGGACATGGAGATACTGGGCAAGGTGACGACC 2160
CACGAGCTGAAGGAGGGCGGCGAGAGCATCCGGGTCACGG 2200
AGGAGAACAAGGAAGAGTACATCATGCTGCTGACTGACTG 2240
GCGTTTCACCCGAGGCGTGGAAGAGCAGACCAAAGCCTTC 2280
CTGGATGGCTTCAACGAGGTGGCCCCGCTGGAGTGGCTGC 2320
GCTACTTTGACGAGAAGAGCTGGAGCTGATGCTGTGCGG 2360
CATGCAGGAGATAGACATGAGCGACTGGCAGAAGAGCACC 2400
ATCTACCGGCACTACACCAAGAACAGCAAGCAGATCCAGT 2440
GGTTCTGGCAGGTGGTGAAGGAGATGGACAACGAGAAGAG 2480
GATCCGGCTGCTGCAGTTTGTCACCGGTACCTGCCGCCTG 2520
CCCGTCGGGGGATTTGCCGAACTCATCGGTAGCAACGGAC 2560
CACAGAAGTTTTGCATTGACAAAGTTGGCAAGGAAACCTG 2600
GCTGCCCAGAAGCCACACCTGCTTCAACCGTCTGGATCTT 2640
CCACCCTACAAGAGCTACGAACAGCTGAGAGAAGCTGC 2680
TGTATGCCATTGAGGAGACCGAGGGCTTTGGACAGGAGTA 2720
ACCGAGGCCGCCCCTCCCACGCCCCCCAGCGCACATGTAG 2760
TCCTGAGTCCTCCCTGCCTGAGAGGCCACTGGCCCCGCAG 2800
CCCTTGGGAGGCCCCCGTGGATGTGGCCCTGTGTGGGACC 2840
ACACTGTCATCTCGCTGCTGGCAGAAAAGCCTGATCCCAG 2880
GAGGCCCTGCAGTTCCCCCGACCCGCGGATGGCAGTCTGG 2920
AATAAAGCCCCCTAGTTGCCTTTGGCCCCACCTTTGCAAA 2960
GTTCCAGAGGGCTGACCCTCTCTGCAAAACTCTCCCCTGT 3000
CCTCTAGACCCCACCCTGGGTGTATGTGAGTGTGCAAGGG 3040
AAGGTGTTGCATCCCCAGGGGCTGCCGCAGAGGCCGGAGA 3080
CCTCCTGGACTAGTTCGGCGAGGAGACTGGCCACTGGGGG 3120
TGGCTGTTCGGGACTGAGAGCGCCAAGGGTCTTTGCCAGC 3160
AAAGGAGGTTCTGCCTGTAATTGAGCCTCTCTGATGATGG 3200
AGATGAAGTGAAGGTCTGAGGGACGGGCCCTGGGGCTAGG 3240
CCATCTCTGCCTGCCTCCCTAGCAGGCGCCAGCGGTGGAG 3280
GCTGAGTCGCAGGACACATGCCGGCCAGTTAATTCATTCT 3320
CAGCAAATGAAGGTTTGTCTAAGCTGCCTGGGTATCCACG 3360
GGACAAAAACAGCAAACTCCCTCCAGACTTTGTCCATGTT 3400
ATAAACTTGAAAGTTGGTTGTTGTTTGTTAXGGTTTGCCA 3440
GGTTTTTTTGTTTACGCCTGCTGTCACTTTCCTGTC 3476 (SEQ ID NO:47)
```

FIG.18B

```
EFAAASTASVATADETERLKRAGVRGLLFHQLHGDDMASA    40
SSSRAGVALPFEKSQLTLKVVSAKPKVHNRQPRINSYVEV    80
AVDGLPSETKKTGKRIGSSELLWNEIIILNVTAQSHLDLK   120
VWSCHTLRNELLGTASVNLSNVLKNNGGKMENMQLTLNLQ   160
TENKGSVVSGGKLTIFLDGPTVDLGNVPNGSALTDGSQLP   200
SRDSSGTAVAPENRHQPPSTNCFGGRSRTHRHSGASARTT   240
PATGEQSPGARSRHRQPVKNSGHSGLANGTVNDEPTTATD   280
PEEPSVVGVTSPPAAPLSVTPNPNTTSLPAPATPAEGEEP   320
STSGTQQLPAAAQAPDALPAGWEQRELPNGRVYYVDHNTK   360
TTTWERPLPPGWEKRTDPRGRFYYVDHNTRTTTWQRPTAE   400
YVRNYEQWQSQRNQLQGAMQHFSQRFLYQFWSASTDHDPL   440
GPLPPGWEKRQDNGRVYYVNHNTRTTQWEDPRTQGMIQEP   480
ALPPGWEMKYTSEGVRYFVDHNTRTTFKDPRPGFESGTK    520
QGSPGAYDRSFRWKYHQFRFLCHSNALPSHVKISVSRQTL   560
FEDSFQQIMNMKPYDLRRRLYIIMRGEEGLDYGGIAREWF   600
FLLSHEVLNPMYCLFEYAGKNNYCLQINPASSINPDHLTY   640
FRFIGRFIAMALYHGKFIDTGFTLPFYKRMLNKRPTLKDL   680
ESIDPEFYNSIVWIKENNLEECGLELYFIQDMEILGKVTT   720
HELKEGGESIRVTEENKEEYIMLLTDWRFTRGVEEQTKAF   760
LDGFNEVAPLEWLRYFDEKELELMLCGMQEIDMSDWQKST   800
IYRHYTKNSKQIQVVFWQWKEMDNEKRIRLLQFVTGTCRL   840
PVGGFAELIGSNGPQKFCIDKVGKETWLPRSHTCFNRLDL   880
PPYKSYEQLREKLLYAIEETEGFGQE    906    (SEQ ID NO:48)
```

FIG. 19

```
GGAGAAGTGCCTGGCGTGGACTATAACTTTCTGACTGTGA 40
AGGAGTTCTTGGACCTCGAGCAGAGTGGGACTCTTCTGGA 80
AGTCGGCACCTATGAAGGAAACTATTATGGGACACCCAAG 120
CCTCCTAGCCAGCCAGTCAGTGGGAAAGTGATCACGACGG 160
ATGCCTTGCACAGCCTTCAGTCTGGCTCTAAGCAGTCGAC 200
CCCGAAGCGAACCAAGTCCTACAATGATATGCAAAATGCT 240
GGCATAGTCCACGCGGAGAATGAGGAGGAGGATGACGTTC 280
CTGAAATGAACAGCAGCTTTACAGCCGATTCTGGTGAACA 320
AGAGGAGCACACTCTCCAAGAAACAGCATTACCACCTGTG 360
AATAGTAGCATCATCGCTGCTCCCATCACGGACCCTTCTC 400
AGAAGTTCCCTCAATACCTACCTCTTTCTGCAGAGGATAA 440
TTTAGGTCCTCTACCTGAAAACTGGGAGATGGCCTATACT 480
GAAAATGGAGAAGTCTATTTTATAGACCATAACACGAAAA 520
CAACATCTTGGTTAGACCCTCGGTGCCTAAACAAGCAGCA 560
GAAGCCACTGGAAGAGTGTGAAGATGATGAAGGGGTACAC 600
ACCGAGGAGCTGGACAGTGAACTAGAACTGCCTGCTGGTT 640
GGGAAAAGATTGAAGACCCATCCCCCGGAATTC 673 (SEQ ID NO:49)
```

FIG.20

```
GEVPGVDYNFLTVKEFLDLEQSGTLLEVGTYEGNYYGTPK  40
PPSQPVSGKVITTDALHSLQSGSKQSTPKRTKSYNDMQNA  80
GIVHAENEEEDDVPEMNSSFTADSGEQEEHTLQETALPPV 120
NSSIIAAPITDPSQKFPQYLPLSAEDNLGPLPENWEMAYT 160
ENGEVYFIDHNTKTTSWLDPRCLNKQQKPLEECEDDEGVH 200
TEELDSELELPAGWEKIEDPSPGI 224 (SEQ ID NO:50)
```

FIG.21

TCGGCGGATTCGTCGACCCACGCGTCCGGCCCGAGCCCTCGGAGGGCGGGGATGTCCCCGAGCCTTGGGAGA
CCATTTCAGAGGAAGTGAATATCGCTGGAGACTCTCTCGGTCTGGCTCTGCCCCCACCACCGGCCTCCCCAG
GATCTCGGACCAGCCCTCAGGAGCTGTCAGACGAACTAAGCAGAAGGCTTCAGATCACTCCAGACTCCAATG
GGGAACAGTTCAGCTCTTTGATTCAAAGAGAACCCTCCTCAAGGTTGAGGTCATGCAGTGTCACCGACGCAG
TTGCAGAACAGGGCCATCTACCACCGCCCAGTGCCCCAGCTGGGAGAGCGCGTTCATCAACTGTCACGGGTG
GTGAGGAACCAACGCCATCAGTGGCCTATGTACATACCACGCCGGGTCTGCCTTCAGGCTGGGAAGAAAGAA
AAGATGCTAAGGGGCGCACATACTATGTCAATCATAACAATCGAACCACAACTTGGACTCGACCTATCATGC
AGCTTGCAGAAGATGGTGCGTCCGGATCAGCCACAAACAGTAACAACCATCTAATCGAGCCTCAGATCCGCC
GGCCTCGTAGCCTCAGCTCGCCAACAGTAACTTTATCTGCCCCGCTGGAGGGTGCCAAGGACTCACCCGTAC
GTCGGGCTGTGAAAGACACCCTTTCCAACCCACAGTCCCCACAGCCATCACCTTACAACTCCCCCAAACCAC
AACACAAAGTCACACAGAGCTTCTTGCCACCCGGCTGGGAAATGAGGATAGCGCCAAACGGCCGGCCCTTCT
TCATTGATCATAACACAAAGACTACAACCTGGGAAGATCCACGTTTGAAATTTCCAGTACATATGCGGTCAA
AGACATCTTTAAACCCCAATGACCTTGGCCCCCTTCCTCCTGGCTGGGAAGAAAGAATTCACTTGGATGGCC
GAACGTTTTATATTGATCATAATAGCAAAATTACTCAGTGGGAAGACCCAAGACTGCAGAACCCAGCTATTA
CTGGTCCGGCTGTCCCTTACTCCAGAGAATTTAAGCAGAAATATGACTACTTCAGGAAGAAATTAAAGAAAC
CTGCTGATATCCCCAATAGGTTTGAAATGAAACTTCACAGPAATAACATATTTGAAGAGTCCTATCGGAGAA
TTATGTCCGTGAAAAGACCAGATGTCCTAAAAGCTAGACTGTGGATTGAGTTTGAATCAGAGAAAGGTCTTG
ACTATGGGGTGTGGCCAGAGAATGGTTCTTCTTACTGTCCAAAGAGATGTTCAACCCCTACTACGGCCTCT
TTGAGTACTCTGCCACGGACAACTACACCCTTCAGATCAACCCTAATTCAGGCCTCTGTAATGAGGATCATT
TGTCCTACTTCACTTTTATTGGAAAAGTTGCTGGTCTGGCCGTATTTCATGGGAAGCTCTTAGATGGTTTCT
TCATTAGACCATTTTACAAGATGATGTTGGGPAAGCAGATAACCCTGAATGACATGGAATCTGTGGATAGTG
AATATTACAACTCTTTGAAATGGATCCTGGAGAATGACCCTACTGAGCTGGACCTCATGTTCTGCATAGACG
AAGAAAACTTTGGACAGACATATCAAGTGGATTTGAAGCCCAATGGGTCAGAAATAATGCTCACAAATGAAA
ACAAAAGGGAATATATCGACTTAGTCATCCAGTGGAGATTTGTGAACAGGGTCCAGAAGCAGATGAACGCCT
TCTTGGAGGGATTCACAGAACTACTTCCTATTGATTTGATTAAAATTTTTGATGAAAATGAGCTGGAGTTGC
TCATGTGCCGGCCTCGGTGATGTGGATGTGAATGACTGGAGACAGCATTCTATTTACAAGAACGGCTACTGCC
CAAACCACCCCGTCATTCAGTGGTTCTGGAAGGCTGTGCTACTCATGGACGCCGAAAAGCGTATCCGGTTAC
TGCAGTTTGTCACAGGGACATCGCGAGTACCTATGAATGGATTTGCCGAACTTTATGGTTCCAATGGTCCTC
AGCTGTTTACAATAGAGCAATGGGGCAGTCCTGAGAAACTGCCCAAAGCTCACACATGCTTTAATCGCCTTG
ACTTACCTCCATATGAAACCTTTGAAGATTTACAAGAGAAACTTCTCATGGCCCGTGGAAAATGCTCAAGGAT
TTGAAGCGGTGGATTAAGCACCCTGTGCCTCGGGGGTCGTTGTTCTTCAAGCAATTTCTGCTTGCACTTTTG (SEQ ID NO: 125)

FIG. 22

SAEFVDPRVRPEpSEGGDVPEPWETISEEVNIAGDSLGLALPPPPASPGSRTSPQELSEELSRRLQITPDSN
GEQFSSLIQREPSSRLRSCSVTDAVAEQGHLPPPSAPAGRARSSTVTGGEEPTPSVAYVHTTPGLPSGWEER
KDAKGRTYYVNHNNRTTTWTRPIMQLAEDGASGSATNSNNHLIEPQIRRPRSLSSPTVTLSAPLEGAKDSPV
RRAVKDTLSNPQSPQPSPYNSPKPQHKVTQSFLPPGWEMRIAPNGRPFFIDHNTKTTTWEDPRLKFPVHMRS
KTSLNPNDLGPLPPGWEERIHLDGRTFYIDHNSKITQWEDPRLQNPAITGPAVPYSREFKQKYDYFRKKLKK
PADIPNRFEMKLHRNNIFEESYRRIMSVKRPDVLKARLWIEFESEKGLDYGGVAREWFFLLSKEMFNPYYGL
FEYSATDNYTLQINPNSGLCNEDHLSYFTFIGKVAGLAVFHGKLLDGFFIRPFYKMMLGKQITLNDMESVDS
EYYNSLKwiLENDpTELDLMFCIDEENFGQTYQVDLKPNGSEIMVTNENKREYIDLVIQWRFVNRVQKQMNA
FLEGFTELLPIDLIKIFDENELELLMCGLGDVDVNDWRQHSIYKNGYCPNHPVIQWFWKAVLLMDAEKRIRL
LQFVTGTSRVPMNGFAELYGSNGPQLFTIEQWGSPEKLPKAHTCFNRLDLPPYETFEDLQEKLLMAVENAQG
FEGVD
(SEQ ID NO: 126)

FIG. 23

| PEPTIDE | SEQUENCE | SEQ. ID NO. | WW DOMAIN/GST FUSION PROTEINS | | | | | | | | | SH3 DOMAINS | |
|---|---|---|---|---|---|---|---|---|---|---|---|---|---|
| | | | WWP1.1 | WWP1.2 | WWP1.3 | WWP1.4 | WWP2.1 | WWP2.2 | WWP2.3 | WWP2.4 | WWP3 | Fyn | Lyn |
| ENaCα-WT | LTAPPPAYATLGP | 168 | ++ | - | ++ | - | +++ | - | +++ | - | - | - | - |
| ENaCα | LTAPPPAAATLGP | 169 | - | - | - | - | - | - | ++ | - | - | - | - |
| ENaCβ-WT | PGTPPPNYDSLRL | 59 | ++ | - | - | - | - | - | ++ | - | - | - | - |
| ENaCβ-P616L | PGTPPLNYDSLRL | 1 | - | - | - | - | - | - | - | - | - | - | - |
| ENaCβ-Y618H | PGTPPPNHDSLRL | 160 | ++ | - | - | - | - | - | - | - | - | - | - |
| ENaCβ | PGTAPPNYDSLRL | 161 | - | - | - | - | - | - | + | - | - | - | - |
| ENaCβ | PGTPAPNYDSLRL | 162 | + | - | - | - | - | - | - | - | - | - | - |
| ENaCβ | PGTPPPNADSLRL | 163 | + | - | - | - | - | - | + | - | - | - | - |
| ENaCβ | PGTPPPNYDALRL | 164 | - | - | - | - | - | - | - | - | - | - | - |
| ENaCβ | PGTPPPNYDSARL | 165 | ++ | - | + | - | ++ | - | + | - | - | - | - |
| ENaCβ | PGTPPPNYDSERL | 166 | - | - | - | - | - | - | - | - | - | - | - |
| ENaCγ-WT | PGTPPPKYNTLRL | 60 | - | - | - | - | - | - | - | - | +++ | - | - |
| ENaCγ | PGTPPPKANTLRL | 167 | - | - | - | - | - | - | - | - | - | - | - |

FIG. 24A

| PEPTIDE | SEQUENCE | SEQ. ID NO. | GST FUSION PROTEINS ||||||
|---|---|---|---|---|---|---|---|---|
| | | | WWP4.1 | WWP4.2 | WWP4.3 | YAP-1 | YAP-2 | FE65 |
| ENaCα-WT | LTAPPPAYATLGP | 168 | + | ++++ | ++++ | - | - | - |
| ENaCα | LTAPPPAAATLGP | 169 | - | - | - | - | - | - |
| ENaCα | PPLALTAPPPAYATLGP | 170 | + | ++++ | ++++ | - | - | - |
| ENaCα | PSPALTAPPPAYATLGP | 171 | + | ++++ | ++++ | - | - | - |
| ENaCα | PSPALTAPPPAAATLGP | 172 | - | - | - | - | - | - |
| ENaCα | PSPALTAPPAY | 173 | - | - | - | - | - | - |
| ENaCβ-WT | PGTPPPNYDSLRL | 59 | - | ++++ | ++++ | - | - | - |
| ENaCβ-P616L | PGTPPLNYDSLRL | 1 | - | - | - | - | - | - |
| ENaCβ-Y618H | PGTPPPNHDSLRL | 160 | - | ++++ | - | - | - | - |
| ENaCβ | PGTAPPNYDSLRL | 161 | - | ++++ | ++++ | - | - | - |
| ENaCβ | PGTPAPNYDSLRL | 162 | - | - | - | - | - | - |
| ENaCβ | PGTPPPNADSLRL | 163 | - | - | - | - | - | - |
| ENaCβ | PGTPPPNYDALRL | 164 | - | ++ | + | - | - | - |
| ENaCβ | PGTPPPNYDSARL | 165 | ++ | ++ | ++ | ++ | ++ | + |
| ENaCβ | PGTPPPNYDSERL | 166 | - | ++++ | ++++ | - | - | - |
| ENaCγ-WT | PGTPPPKYNTLRL | 60 | - | - | - | - | - | - |
| ENaCγ | PGTPPPKANTLRL | 167 | - | - | - | - | - | - |
| Src | GILAPPVPPRNTR | 62 | - | - | - | - | - | - |
| Crk | SVPAPPPLPPKSGG | 63 | - | - | - | - | - | - |

FIG.24B

| PEPTIDE | SEQUENCE | SEQ. ID NO. | WWP1.1 | WWP1.2 | WWP1.3 | WWP1.4 | WWP2.1 | WWP2.2 | WWP2.3 | WWP2.4 | WWP3 | WWP4.1 | WWP4.2 | WWP4.3 | YAP1 | YAP2 |
|---|---|---|---|---|---|---|---|---|---|---|---|---|---|---|---|---|
| bWW061 | NRLDLPPYKSYEQ | 179 | - | - | - | + | ++ | - | - | - | - | - | + | - | - | - |
| bWW062 | NRLDLPPAKSYEQ | 180 | + | - | - | - | - | - | - | + | - | - | - | - | - | - |
| bWW059 | NRLDLPPYETFED | 181 | - | - | ++ | - | +++ | + | - | ++ | - | + | ++ | + | - | - |
| bWW060 | NRLDLPPAETFED | 182 | - | - | - | - | - | - | - | - | - | - | - | - | - | - |
| WBP-2A | YVQPPPPPYPGPM | 8 | +++ | ++++ | ++++ | ++++ | ++++ | ++++ | ++++ | ++++ | ++++ | ++++ | ++++ | ++++ | ++++ | ++++ |

FIG. 25

| DOMAIN | WWP1.1 | RELATIVE BINDING AFFINITY | |
|---|---|---|---|
| cw | | | |
| 1 | GLPPPYDLTWVN | **** | 183 |
| 1 | GDVRFWGAPPPY(SRPSR) | **** | 184 |
| 4 | LKLPDYWESSAS | * | 185 |
| 1 | LKLPEYWESSAS | | 186 |

| pp LIBRARY | | |
|---|---|---|
| RSERGVPPTYAEFFPM | | 187 |
| NMPHVMPPPYAQYR | *** | 188 |
| GAHDSPPPYSRYWP | ***** | 189 |
| GPSEQPPPYETVK | **** | 190 |

| xy LIBRARY | | |
|---|---|---|
| SRIKGDPPGYEEVMGL | *** | 191 |
| QTDYPPPGYPWWESR | *** | 192 |
| GVEFGPPPDYEALFKP | ** | 193 |

| | WWP1,4 | RELATIVE BINDING AFFINITY | |
|---|---|---|---|
| cw | LIBRARY | | |
| 1 | MLPEYTEYGFSM | ** | 194 |
| 1 | TLLPGYLSDEYW | ***** | 195 |
| 1 | LKLPDYWESSAS | * | 196 |
| 3 | LLPNYGEWWRGG | * | 197 |
| 2 | SLPTYGHELFW | **** | 198 |
| 1 | SLLPEYNMPLYH | ***** | 199 |
| 1 | LMLPAYNEAVTW | * | 200 |
| 1 | LMLPHYGDMQFA | ** | 201 |
| 1 | LLPMYGEAEAWF | ** | 202 |

| pp LIBRARY | | |
|---|---|---|
| QLPISPPPYSEMGL | *** | 203 |
| GWTLGDPPPYHIAG | ***** | 204 |
| RGGVWLPPPYSSIDN | ** | 205 |
| HKPLTPPPYDAHDF | * | 206 |
| LFWQVGPPSYEEAI | ** | 207 |

| xy LIBRARY | | |
|---|---|---|
| PSMLTLPPYFEHKQDE | ***** | 208 |
| WSMKTSPPSYESIFGL | **** | 209 |
| AVHSLTLPAYEATEYM | ***** | 210 |
| GRVVSHPPAYCELFKC | ***** | 211 |
| SGRMQGPPEYGDMEYV | * | 212 |

| | WWP3 | RELATIVE BINDING AFFINITY | |
|---|---|---|---|
| cw | LIBRARY | | |
| 4 | GMLPSYEEAVMA | **** | 213 |
| 5 | PIAPPTYWEWAL | **** | 214 |
| 1 | RLPAYKEPAATF | * | 215 |
| 1 | LPSYSEWVAETR | **** | 216 |
| 2 | LPTYNEYLTRAA | *** | 217 |

| pp LIBRARY | | |
|---|---|---|
| RVYRDLPPPYPQGT | ** | 218 |
| HRSELPPPYSEAVK | **** | 219 |
| GGWRAVPPPYPGSP | * | 220 |
| LMRRAPPPPYPQVA | * | 221 |
| RLYTTPPPYASLHK | * | 222 |
| PMHRVGPPPPYPGL | **** | 223 |

| xy LIBRARY | | |
|---|---|---|
| PWLRGDPPPYMELVSE | **** | 224 |
| GSWETPPPSYEEMLRK | ** | 225 |
| AHMYRPPPPYRGSSDG | **** | 226 |
| GRFLREPPPYPNRDVA | ** | 227 |
| VAMRDPPPPYNYVDAP | ** | 228 |
| VATLRPPPAYGVEYSR | ** | 229 |
| MLKDVAPPAYEEAVRR | *** | 230 |

FIG. 27

IDENTIFICATION AND ISOLATION OF NOVEL POLYPEPTIDES HAVING WW DOMAINS AND METHODS OF USING SAME

This application is a continuation of U.S. application Ser. No. 08/826,516, filed Apr. 13, 1997, now abandoned, which is a continuation-in-part of U.S. application Ser. No. 08/630,916, filed Apr. 3, 1996, now U.S. Pat. No. 6,011,137, which are incorporated herein by reference in their entirety.

1. FIELD OF THE INVENTION

The present invention is directed to the identification and isolation of polypeptides having WW domains or functional equivalents thereof. Various methods of use of these polypeptides are described including, but not limited to, targeted drug discovery. Also provided are various peptide recognition units that bind to WW domains.

2. BACKGROUND OF THE INVENTION

2.1. Functional Domains in Proteins

Many biological processes involve the specific binding of proteins to one another. Examples of such processes are signal transduction, transcription, DNA replication, cytoskeletal organization, membrane transport, etc. In many cases it has been shown that specific binding is mediated by small portions of the proteins involved and that these portions can function to a large extent independently of the rest of the proteins. Such independent portions of proteins, mediating specific recognition or binding of one protein by another, have come to be called "functional domains". A variety of functional domains have been characterized to a variety of levels of understanding. Some of these are described below.

Src homology 2 domains (SH2) domains are short (about 100 residues) amino acid sequences that were originally found in the non-membrane bound tyrosine kinase Src. Since then they have been shown to occur in about 20 other proteins. SH2 domains recognize certain phosphotyrosine-containing sites on proteins. Proteins containing SH2 domains participate in a variety of signalling pathways. For reviews discussing SH2 domains see Pawson, 1995, Nature 373:573–580; Cohen et al., 1995, Cell 80:237–248; Pawson and Gish, 1992, Cell 71:359–362; Koch et al., 1991, Science 252:668–674.

Src homology 3 (SH3) domains are another class of short amino acid sequences that were originally found by comparing the amino acid sequence of the Src protein with the sequences of Crk, Phospholipase C-γ, α-Spectrin, Myosin IB, Cdc25, and Fusl (Lehto et al., 1988, Nature 334:388; Mayer et al., 1988, Nature 332:272–275; Stahl et al., 1988, Nature 332:269–272; Rodaway et al., 1989, Nature 342:624). In addition to Src, almost 30 proteins are known to contain SH3 domains and these proteins perform a wide range of functions.

For reviews discussing SH3 domains see Pawson, 1995, Nature 373:573–580; Cohen et al., 1995, Cell 80:237–248; Pawson and Gish, 1992, Cell 71:359–362; Koch et al., 1991, Science 252:668–674.

SH3 domains have been shown to specifically bind certain proline-rich amino acid sequences (Chen et al., 1993, J. Am. Chem. Soc. 115:12591–12592; Ren et al., 1993, Science 259:1157–1161; Feng et al., 1994, Science 266:1241–1247; Yu et al., 1994, Cell 76:933–945; Sparks et al., 1994, J. Biol. Chem. 269:23853–23856; Sparks et al., 1996, Proc. Natl. Acad. Sci. USA 93:1540–1544). However, in general, the homology between different sequences that bind SH3 domains tends to be low.

This low homology would explain the specificity that has usually been observed for the interactions between SH3 domains and their natural ligands. Generally, a sequence that is identified by screening for binders to a particular SH3 domain will bind to that particular SH3 domain much more strongly that it binds to other SH3 domains. For example, Cicchetti et al., 1992, Science 257:803–806 probed a λgt11 cDNA expression library with a glutathione S-transferase fusion protein containing the 55 amino acid SH3 region of Abl and isolated two clones that produced proteins capable of specifically binding the Abl SH3 domain. Analysis of one of the clones uncovered the region of the encoded protein responsible for binding to the SH3 domain. This region, as part of a glutathione S-transferase fusion protein, bound the SH3 domain from Abl very strongly, the SH3 domain from Src less well, and the SH3 domains from Crk and neural Src very weakly.

Pleckstrin is the major substrate for Protein Kinase C in platelets. Two domains of about 100 amino acids in Pleckstrin have been found to have counterparts in a number of signal transduction and cytoskeletal proteins. These domains are known as Pleckstrin homology, or PH, domains (Haslam et al., 1993, Nature 363:309–310; Mayer et al., 1993, Cell 73:629–630). Although the sequence homology between PH domains from various proteins is low, structural studies have shown that PH domains fold into a similar conformation containing two antiparallel β sheets and a long C-terminal α helix (Gibson et al., 1994, Trends Biochem. Sci. 19:349–353). Among the proteins that have been found to have PH domains are a number of proteins with important roles in signal transduction or cytoskeletal architecture, e.g., Spectrin, Dynamin, Phospholipase C-γ, Btk, RasGAP, mSOS-1, Rac, Akt.

Leucine zippers consist of alpha helical regions of proteins in which a leucine residue appears at every seventh position along the helix. The leucines interdigitate with leucines from the leucine zipper of a different protein or another molecule of the same protein, leading to dimerization of the proteins containing the leucine zippers. Leucine zippers have been found in a number of proteins that are believed to function as transcription factors, e.g., C/EBP, Myc, Fos, Jun, GCN4. In many of these proteins, dimerization through leucine zippers has been shown to be necessary for the DNA binding activity of the transcription factor.

The binding of leucine zippers exhibits specificity in that some leucine zippers preferably bind to certain other leucine zippers. For example, the Jun-Fos heterodimer formed by the binding of the leucine zippers of Fos and Jun forms in preference to a Jun-Jun homodimer formed by the binding of the leucine zippers of two Jun proteins. Fas/APO-1(CD95) is a member of a class of transmembrane receptors that have been shown to be involved in the phenomenon of programmed cell death or apoptosis (Itoh et al., 1991, Cell 66:233–243). The tumor necrosis factor receptor 1 (TNFR-1) is also a member of this class (Baglioni, C., 1992, "The Molecules and Their Emerging Roles in Medicine," in *Tumor Necrosis Factors*, B. Beutler, ed. (New York: Raven Press). Itoh, N. and Nagata, S., 1993, J. Biol. Chem. 268:10932–10937 have shown that certain amino acid sequences in the cytoplasmic domain of Fas/APO-1(CD95) are required for the programmed cell death response mediated by this receptor. Tartaglia et al., 1993, Cell 74:845–853 proposed that a similar region in TNFR-1 also is responsible for programmed cell death. This region of similarity between Fas/APO-1(CD95) and TNFR-1 has come to be called the cell death domain.

Three groups have used the yeast two-hybrid system to clone genes whose products specifically bind to the cell death domains of Fas/APO-1(CD95) and TNFR-1 (Hsu et al., 1995, Cell 81:495–504; Chinnaiyan, et al., 1995, Cell 81:505–512; Stanger et al., 1995, Cell 81:513–523). These genes were shown to induce apoptosis when overexpressed in certain cell types, a result which argues that they are intracellular transducers of death signals from Fas/APO-1 (CD95) and TNFR-1.

2.1.1. WW Domains

The WW domain is a small functional domain found in a large number of proteins from a variety of species including humans, nematodes, and yeast. Its name is derived from the observation that two tryptophan residues, one in the amino terminal portion of the WW domain and one in the carboxyl terminal portion, are almost invariably conserved. At about 30 to 40 amino acids in length, it is quite small for a functional domain, most of which tend to be from 50 to 150 residues long. Often a WW domain will be flanked by stretches of amino acids rich in histidine or cysteine; these stretches might be metal-binding sites. The center of WW domains is quite hydrophobic; however, sprinkled throughout the rest of the domain are a high number of charged residues. These features are characteristic of functional domains involved in protein-protein interactions (Bork and Sudol, 1994, Trends in Biochem. Sci. 19:531–533).

Based upon their study of various WW domains, André and Springael, 1994, Biochem. Biophys. Res. Comm. 205: 1201–1205 ("André and Springael") proposed the following consensus sequence for WW domains:

$WX_7G(K/R)X_1(Y/F)(Y/F)X_1(N/D)X_2(T/S)(K/R)X_1(T/S)(T/Q/S)WX_2P$ (SEQ ID NO:2)

where X represents any amino acid and bold letters represent highly conserved amino acids. André and Springael's analysis of WW domains led them to conclude that WW domains lack α-helical content, instead possessing a central β-strand region flanked by unstructured regions. Other studies predict a structure of β-strands containing charged residues flanking a hydrophobic core composed of four aromatic residues (Chen and Sudol, 1995, Proc. Natl. Acad. Sci. USA 92:7819–7823, and references cited therein).

The WW domain has been found in a wide variety of proteins of varying function. Despite this diversity of function, it appears that most proteins containing WW domains for which a function is known have something to do with either cell signalling and growth regulation or the organization of the cytoskeleton.

For example, the WW domain-containing protein dystrophin belongs to a family of cytoskeletal proteins that includes α-actinin and β-spectrin. Mutations in dystrophin are responsible for Duchenne and Becker muscular dystrophies. The dystrophin gene gives rise to a family of alternatively spliced transcripts. The longest of these encodes a protein having four domains: (1) a globular, actin-binding region; (2) 24 spectrin-like repeats; (3) a cysteine-rich $Ca^{2+}$ binding region; and (4) a carboxyl terminal globular region. A short stretch of the dystrophin protein, after the spectrin-like repeats and before the $Ca^{2+}$ binding region, contains a WW domain. This WW domain is in an area that has been shown to bind β-dystroglycan. This suggests that WW domains may be involved in protein-protein interactions (Bork and Sudol, 1994, Trends in Biochem. Sci. 19:531–533).

Utrophin, a protein having 70% sequence homology to dystrophin, and, like dystrophin, capable of forming tetramers via its spectrin-like repeats, also possesses a WW domain. Utrophin and dystrophin are believed to be involved in membrane stability and the transmission of contractile forces to the extracellular environment (Bork and Sudol, 1994, Trends in Biochem. Sci. 19:531–533).

YAP is a protein that was discovered by virtue of its binding to the SH3 domain of the proto-oncogene Yes (Sudol, 1994, Oncogene 9:2145–2152). Murine YAP was found to have two WW domains; interestingly, chicken and human YAP each have only a single WW domain (Sudol, et al., 1995, J. Biol. Chem. 270:14733–14741). Chen and Sudol, 1995, Proc. Natl. Acad. Sci. USA 92:7819–7823 screened a cDNA expression library with bacterially produced glutathione S-transferase fusion proteins of the WW domain from YAP. They identified and isolated two proteins from the library (WBP-1 and WBP-2) that specifically bound the YAP WW domain. Comparison of the amino acid sequences of WBP-1 and WBP-2 revealed a homologous proline-rich region in each protein. The proline-rich regions contained the shared motif PPPPY (SEQ ID NO:3). Chen and Sudol then showed that as few as ten residues containing this motif conferred upon a fusion protein the ability to specifically bind the YAP WW domain. This binding was highly specific; the motif bound to the YAP WW domain but not to the WW domain from dystrophin or to a panel of SH3 domains.

Nedd-4 is a protein which possesses three WW domains. In mouse, Nedd-4 seems to play a role in embryonic development and the differentiation of the central nervous system (Kumar et al., 1992, Biochem. Biophys. Res. Comm. 185:115–1161).

RSP5 is a protein of yeast that is involved in the phenomenon of nitrogen catabolite inactivation whereby a number of permeases that import nitrogenous compounds into the cell are inactivated when yeast are exposed to a good nitrogen source such as $NH_4^+$. RSP5 probably interacts with the transcription factor SPT3 since certain alleles of RSP5 can complement mutations in SPT3 (Eisenmann et al., 1992, Genes Dev. 6:1319–1331).

RSP5 contains three WW domains in its amino terminus. RSP5 appears to be a homolog of the vertebrate protein Nedd-4. The 6 total WW domains of RSP5 and Nedd-4 share 30% amino acid sequence identity and 50% similarity. The carboxyl terminal domains of both RSP5 and Nedd-4 are homologous to the carboxyl terminal domain of E6-AP, a human ubiquitin-protein ligase (André and Springael). A region of RSP5 known as HECT can form a high energy thioester bond with ubiquitin, arguing that RSP5 is a ubiquitin-protein ligase (Scheffner et al., 1995, Cell 75:495–505; Huibregste et al., 1995, Proc. Natl. Acad. Sci. USA 92:2563–2567).

Another yeast protein, ess1, contains a WW domain and is thought to be involved in cytokinesis and/or cell separation (Hanes et al., 1989, Yeast 5:55–72).

A search of protein databases, using the WW domains of Nedd-4 and RSP5, identified two proteins of unknown function, YKLO12W from *Saccharomyces cerevesiae* and Z22176 from *Caenorhabditis elegans*, each containing two WW domains at their amino terminus (André and Springael).

Among other proteins having WW domains, the rat transcription factor FE65 possesses an amino terminal activation region that includes a WW domain (Bork and Sudol, 1994, Trends in Biochem. Sci. 19:531–533). The human protein kiaa93 has 4 WW domains and shares other regions of sequence similarity with RSP5, and may be the human version of mouse Nedd-4 (Hoffman and Bucher, 1995, FEBS Lett. 358:153–157). The human protein HUMORF1, although of unknown function, has a roughly 350 amino acid region which is homologous to GTPase-activating proteins (André and Springael).

Citation of a reference hereinabove shall not be construed as an admission that such is prior art to the present invention.

3. SUMMARY OF THE INVENTION

In general, the present invention is directed to a method of identifying an exhaustive set of compounds binding operationally defined ligands that are involved in binding interactions with WW domains.

More specifically, the present invention is directed to a method of identifying a polypeptide or family of polypeptides having a WW domain. The basic steps of the method comprise: (a) choosing a recognition unit or set of recognition units having a selective affinity for a WW domain in a target molecule of interest; (b) contacting the recognition unit with a plurality of polypeptides; and (c) identifying one or more polypeptides having a selective affinity for the WW domain of interest, which polypeptides include the WW domain of interest or a functional equivalent thereof.

In one particular embodiment of the invention, exhaustive screening of proteins having a desired WW domain involves an iterative process by which recognition units for WW domains identified in a first round of screening are used to detect WW domain-containing proteins in successive expression library screens.

More particularly, the method of the present invention includes choosing a recognition unit having a selective affinity for a WW domain of interest. With this recognition unit, it has been discovered that a plurality of polypeptides from various sources can be examined such that certain polypeptides having a selective affinity for the recognition unit can be identified. The polypeptides so identified have been shown to include a WW domain; that is, the WW domains found are working versions that are capable of displaying the same binding specificity (binding to the same recognition unit, particularly under the multivalent recognition unit screening conditions taught by the present invention) as the WW domain of interest. Hence, the polypeptides identified by the present method also possess those attributes of the WW domain of interest which allow these related polypeptides to exhibit the same, similar, or analogous (but functionally equivalent) selective binding affinity characteristics as the WW domain of interest of the initial target molecule.

In specific embodiments of the present invention, the plurality of polypeptides is obtained from the proteins produced by a cDNA expression library. The binding specificity of the polypeptides which bear a WW domain or a functional equivalent thereof for various peptides or recognition units can subsequently be examined, allowing for a greater understanding of the physiological role of particular polypeptide/recognition unit interactions. Indeed, the present invention provides a method of targeted drug discovery based on the observed effects of a given drug candidate on the interaction between a recognition unit-polypeptide pair or a recognition unit and a "panel" of related polypeptides each with a copy or a functional equivalent of (e.g., capable of displaying the same binding specificity as) a WW domain.

The present invention also provides polypeptides comprising certain amino acid sequences. Moreover, the present invention also provides nucleic acids, including certain DNA constructs comprising certain coding sequences. Other compositions are likewise contemplated which are products of the methods of the present invention.

The present inventors have found, unexpectedly, that the valency (i.e., whether it is a monomer, dimer, tetramer, etc.) of the recognition unit that is used to screen an expression library or other source of polypeptides appears to have a marked effect upon the specificity of the recognition unit-WW domain interaction. The present inventors have discovered that recognition units in the form of small peptides, in multivalent form, have a specificity that is eased but not forfeited. In particular, biotinylated peptides bound to a multivalent (believed to be tetravalent) streptavidin-alkaline phosphatase complex have an unexpected generic specificity. This allows such peptides to be used to screen libraries to identify classes of polypeptides containing WW domains that are similar but not identical in sequence to the peptides' target WW domains.

The present invention also provides methods for identifying potential new drug candidates (and potential lead compounds) and determining the specificities thereof. For example, knowing that a polypeptide with a WW domain and a recognition unit, e.g., a binding peptide, exhibit a selective affinity for each other, one may attempt to identify a drug that can exert an effect on the polypeptide-recognition unit interaction, e.g., either as an agonist or as an antagonist (inhibitor) of the interaction. With this assay, then, one can screen a collection of candidate "drugs" for the one exhibiting the most desired characteristic, e.g., the most efficacious in disrupting the interaction or in competing with the recognition unit for binding to the polypeptide.

In addition, the present invention also provides certain assay kits and methods of using these assay kits for screening drug candidates. In a particular aspect of the present invention, the assay kit comprises: (a) a polypeptide containing a WW domain; and (b) a recognition unit having a selective affinity for the polypeptide. Yet another assay kit may comprise a plurality of polypeptides, each polypeptide containing a WW domain, preferably of a different sequence, and at least one recognition unit having a selective affinity for each of the plurality of polypeptides.

4. DESCRIPTION OF THE FIGURES

FIG. 1 is a schematic representation of the general aspects of a method of identifying recognition units exhibiting a selective affinity for a target molecule containing a WW domain. In this illustration, the target molecule is a polypeptide having a WW domain, and the recognition units are peptides having a selective affinity for the WW domain that are expressed in a phage display library.

FIG. 2 illustrates a strategy for exhaustively screening an expression library for WW domain-containing proteins. A peptide recognition unit is generated by screening a combinatorial peptide library for binders to a WW domain expressed bacterially as a GST fusion protein. This peptide is then used to select a subset of the WW domain-containing proteins represented in a cDNA expression library. A combinatorial library is once again used to identify recognition units of WW domains identified in the first expression library screen; these recognition units identify overlapping sets of proteins from the expression library. With multiple iterations of this process, it should be possible to clone systematically all WW domains represented in a given cDNA expression library.

FIG. 3 is a schematic representation of the general method of identifying polypeptides containing a WW domain by screening a plurality of polypeptides using a suitable recognition unit. In the illustration, the plurality of polypeptides is obtained from a cDNA expression library, and the recognition units are WW domain-binding peptides.

FIG. 4 illustrates how a WW domain-binding peptide can be used to identify other WW domain-containing proteins. Shown is a schematic representation of the progression from initial selection of a target molecule containing a WW domain, choice of peptide recognition unit, and identification of polypeptides that have a selective affinity for the recognition unit and include the WW domain of the initial target molecule or a functional equivalent thereof.

FIG. 5 shows an alignment of the twelve novel WW domains from the novel proteins WWP1, WWP2, WWP3, and WWP4 as well as WW domains from a variety of known proteins. This alignment illustrates the minimal primary sequence homology among various known WW domains. "pos" indicates, where known, the position of the first amino acid of the displayed sequence in the indicated proteins. "acc. no." indicates GenBank accession numbers. Residues FIG. 10 is a schematic depiction of three clones of novel WW domain-containing genes isolated by screening human bone marrow and brain cDNA expression libraries with the peptides WBP-1, WBP-2A, and WBP-2B, and a fourth clone of a novel WW domain-containing gene isolated by screening a human prostate cDNA expression library with ENaCβ and ENaCγ. Black boxes indicate WW domains; boxes with cross hatching indicate HECT domains; the empty box indicates a guanylate kinase-like domain. The box with dots indicates a C2 domain. Arrows denote incomplete N and C-terminal coding sequences. See Sections 6.1 and 6.1.1 for details.

```
TCCTCGAGTATCGACATGCCTTAGACTGCTAGCACTATGTACAACATGCTTCATCGCAACGA          SEQ ID NO:4

GCCAGGTGGGAGGAAGTTGAGCCCGCCCGCCAACGACATGCCGCCCGCCCTCCTGAAGAGGTCTAGA is.

TASTMYNMLHRNEPGGRKLSPPANDMPPALLKRSR is.                                SEQ ID NO:5

SSIDMP is.                                                             SEQ ID NO:51
``` in boldface are those that are conserved in greater than 75% of the sequences. A single amino acid gap has been introduced in the amino acid sequence of the third WW domain of WWP2 (WWP2–3) between positions 12 and 13 in order to maximize homology with the other WW domains. In the consensus sequence (SEQ ID NO: 39):

X represents any amino acid;
h represents a hydrophobic amino acid; and
t represents a polar amino acid.

Figure 6A:
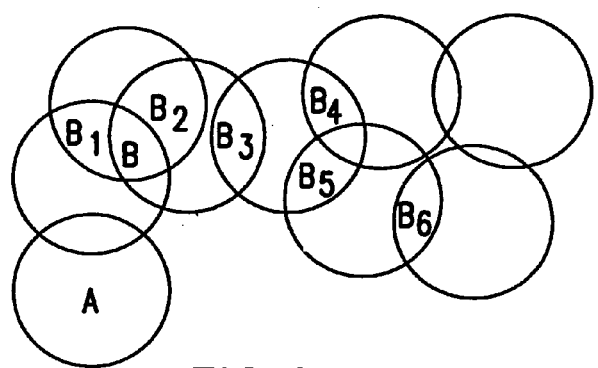

FIG. 6A is a schematic representation of a population of WW domains represented by the circles. "A" is a recognition unit specific to one circle only. B, on the other and, recognizes three WW domains, while B1 and B2 recognize only two each.

Figure 6B:
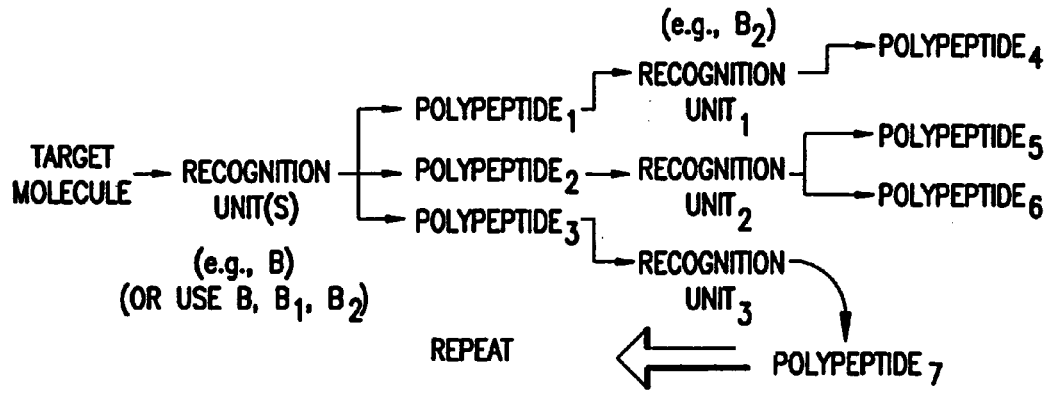

FIG. 6B illustrates an iterative method whereby new recognition units are chosen based on polypeptides uncovered with the first recognition unit(s). These new recognition units lead to the identification of other related polypeptides, etc., expanding the scope of the study to increasingly diverse members of the related population.

FIG. 7 depicts the results of experiments in which peptide sequences from the indicated genes were synthesized and tested for their ability to bind to the novel WW domains described in Sections 6.1 and 6.1.1. Purified phage clones were applied to a bacterial lawn, grown for an appropriate time, and filter lifts were processed as in Section 6.1. A minus indicates no binding; a plus indicates binding, with the number of pluses indicating the strength of binding. For further details, see Section 6.3.

Figure 8:
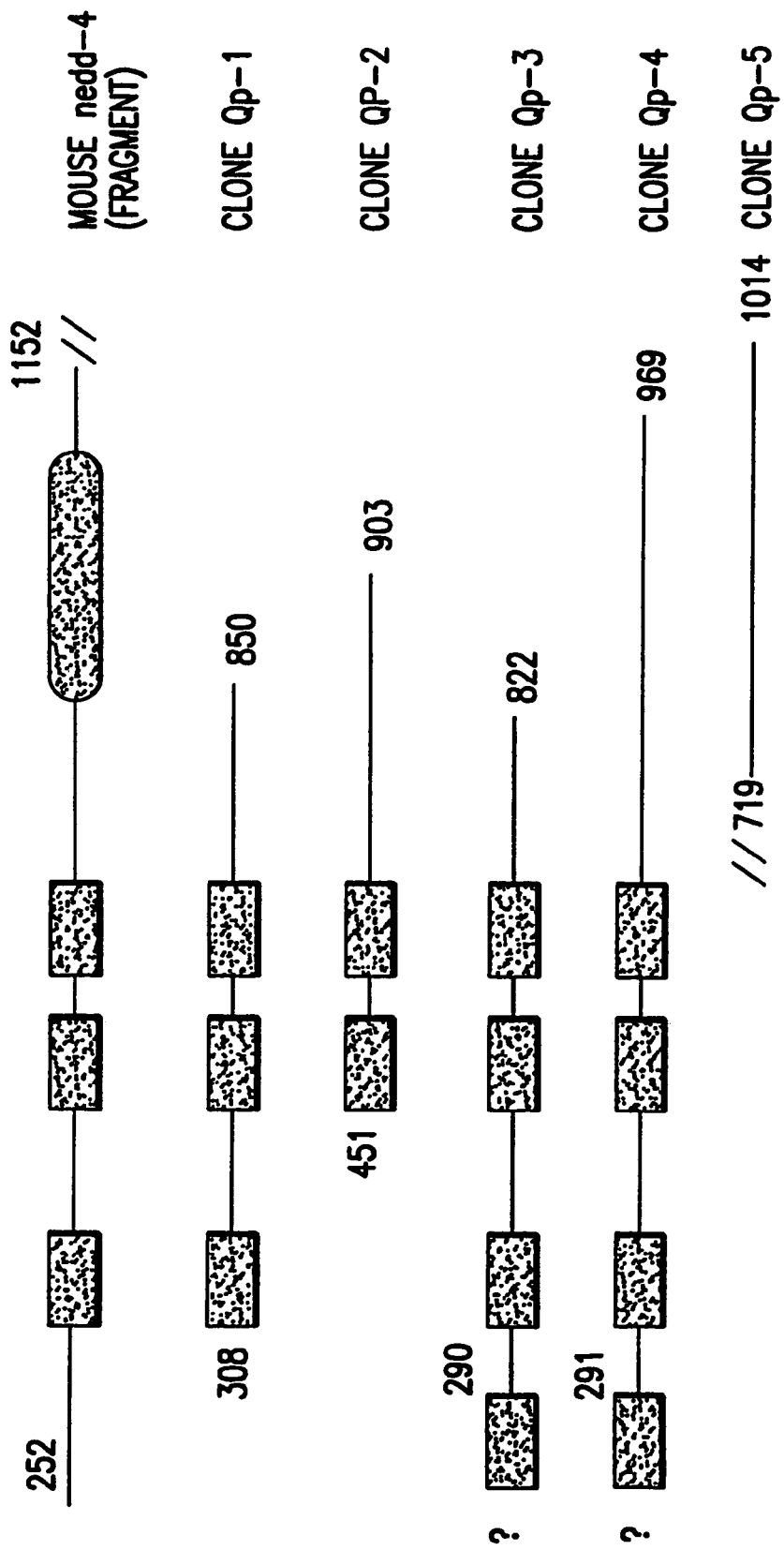

FIG. 8 is a schematic depiction of 5 clones of the Nedd-4 gene isolated by screening a 16 day mouse embryo cDNA library with the QP peptide (SEQ ID NO:8). Black boxes indicate WW domains. See Section 6.1 for details.

Figure 9:
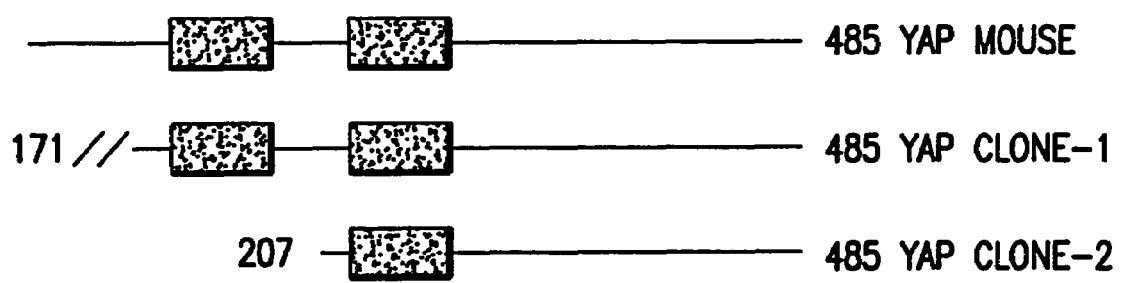

FIG. 9 is a schematic depiction of 2 clones of the YAP gene isolated by screening a 16 day mouse embryo cDNA library with a 1:1:1 mixture of the peptides TP, YP, and QP (SEQ ID NOs:6, 7, and 8). Black boxes indicate WW domains; // indicates regions still to be sequenced. See Section 6.1 for details.

Figure 13:
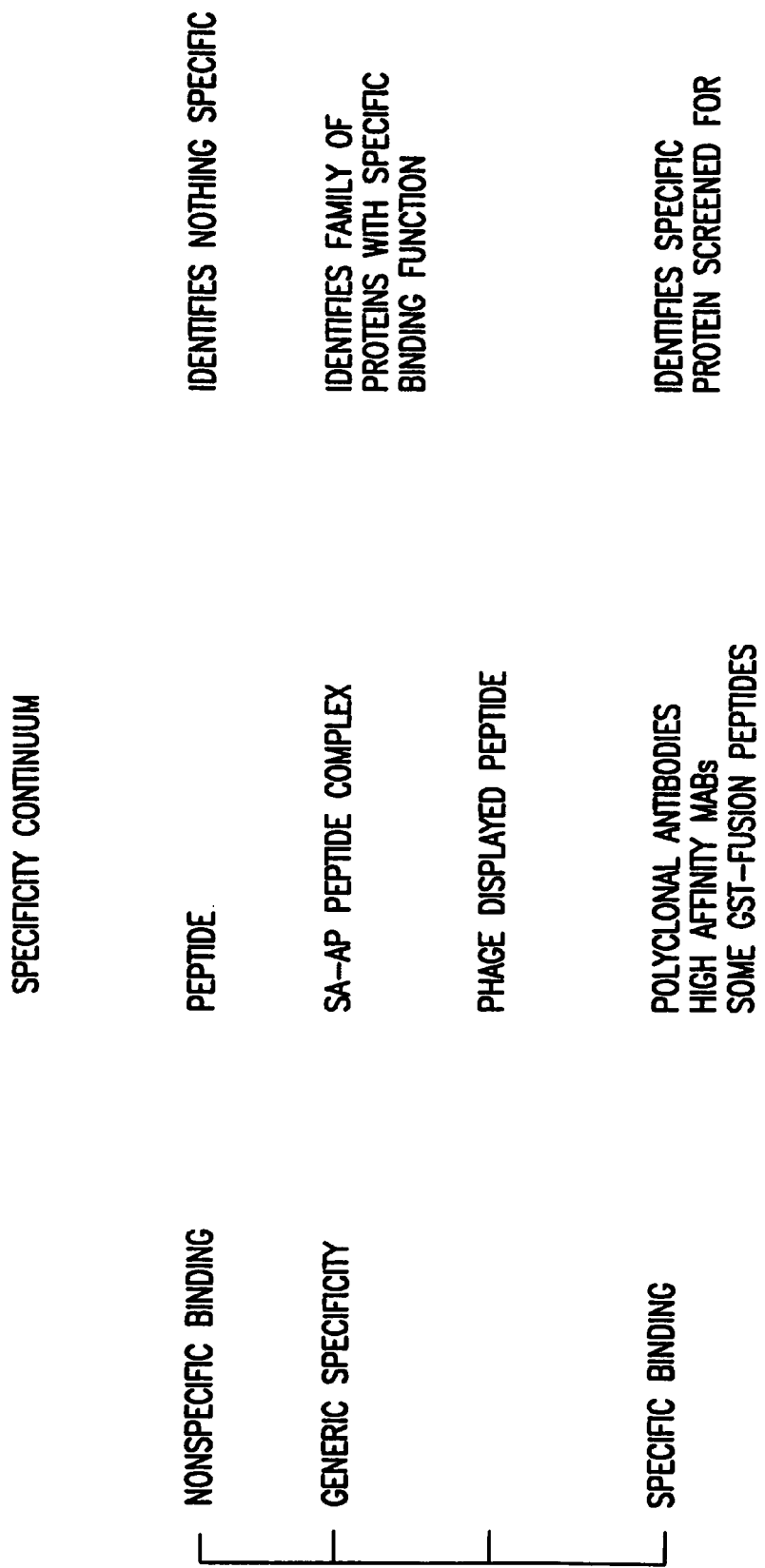

FIG. 13 depicts the specificity continuum described in Section 5.2.1. "SA-AP peptide complex" represents the tetravalent complex of streptavidin-alkaline phosphatase and biotinylated peptide described in that section.

FIG. 14 shows a comparison of the HECT domain sequences from WWP1 and WWP2 and the HECT domains of various proteins. See Section 6.1.1.

FIGS. 15A, B, C and D show the results of a cross affinity mapping experiment wherein biotinylated peptides were tested for their relative binding to individual WW domains expressed as GST fusion proteins. PPPPY and PPPPY-like motifs within the peptide sequences are underlined and specific alanine substitution variants of the WBP-1 and WBP-2A peptides are indicated in bold. Relative binding was assessed from three independent determinations. All PPPPY motif peptides displayed no detectable binding to GST control protein or to BSA. See Section 6.3 for details.

FIG. 16 depicts the nucleotide sequence of WWP1, a novel human gene (SEQ ID NO:45).

FIG. 17 depicts the amino acid sequence of WWP1, a novel human gene (SEQ ID NO:46).

FIG. 18A depicts the nucleotide sequence from position 1–1800 of WWP2, a novel human gene (a portion of SEQ ID NO:47).

FIG. 18B depicts the nucleotide sequence from position 1800–3476 of WWP2, a novel human gene (a portion of SEQ ID NO:47).

FIG. 19 depicts the amino acid sequence of WWP2, a novel human gene (SEQ ID NO:48).

FIG. 20 depicts the nucleotide sequence of WWP3, a novel human gene (SEQ ID NO:49).

FIG. 21 depicts the amino acid sequence of WWP3, a novel human gene (SEQ ID NO:50).

FIG. 22 depicts the nucleotide sequence of WWP4, a novel human gene (SEQ ID NO:125).

FIG. 23 depicts the amino acid sequence of WWP4, a novel human gene (SEQ ID NO:126). The three WW domains are underlined (these domains are identified as SEQ ID NOs:127–129, which identification corresponds to the respective order from the amino terminus). The HECT domain (SEQ ID NO:130) is contained in the last 300 amino acids of WWP4.

FIGS. 24A and B show the results of a cross affinity mapping experiment wherein PPPPY motif-containing peptides derived from the α, β, and γ wild-type subunits of human ENaC and several variants were tested for their relative binding to WW-GST fusion proteins. ENaCβP616L and ENaCβ-Y618H denote peptides containing specific missense substitutions found in Liddle Syndrome patients. Amino acid substitutions are indicated in bold.

FIG. 25 shows a cross affinity mapping experiment wherein Biotinylated peptides (corresponding to the PPPPY-like motif of WWP2 (Peptide bWW061) (SEQ ID NO:3) and WWP4 (Peptide bWW059) were tested for their relative binding to individual WW domains expressed as GST fusion proteins (following methods as set forth in Section 6.1). PPPPY (SEQ ID NO:3) and PPPPY (SEQ ID NO:3)-like motifs are underlined and specific alanine substitution peptide variants of the PPPPY-like motif in the HECT domain of WWP2 and WWP4 (the variants are identified as peptide bWW061 and bWW060, respectively) are indicated in bold.

Figure 26A:
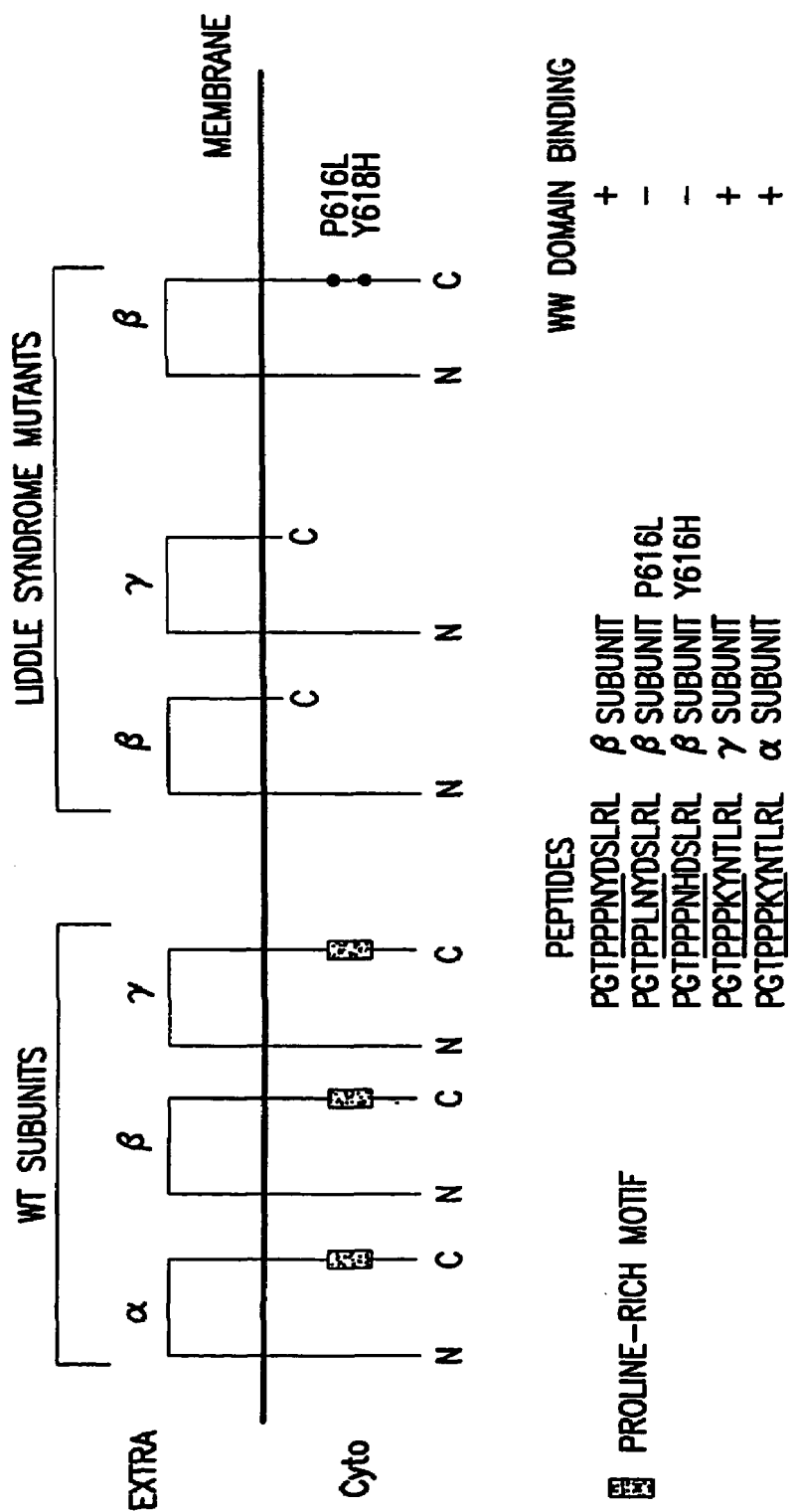

FIG. 26A depicts the Epithelial Na⁺ Channel and Liddle syndrome associated mutations. The wild type epithelial Na⁺ Channel protein consists of α, β, and γ subunits. Each subunit contains a proline rich motif, i.e. a WW domain binding sequence. In Liddle syndrome the Epithelial Na⁺ channel protein is mutated: either the β or γ subunits are truncated such that they lack the proline-rich motif or point mutations have been found in the β subunit that change the PPPNY motif to PPLNY (labeled P616L) or to PPPNH (Y618H).

Figure 26B:
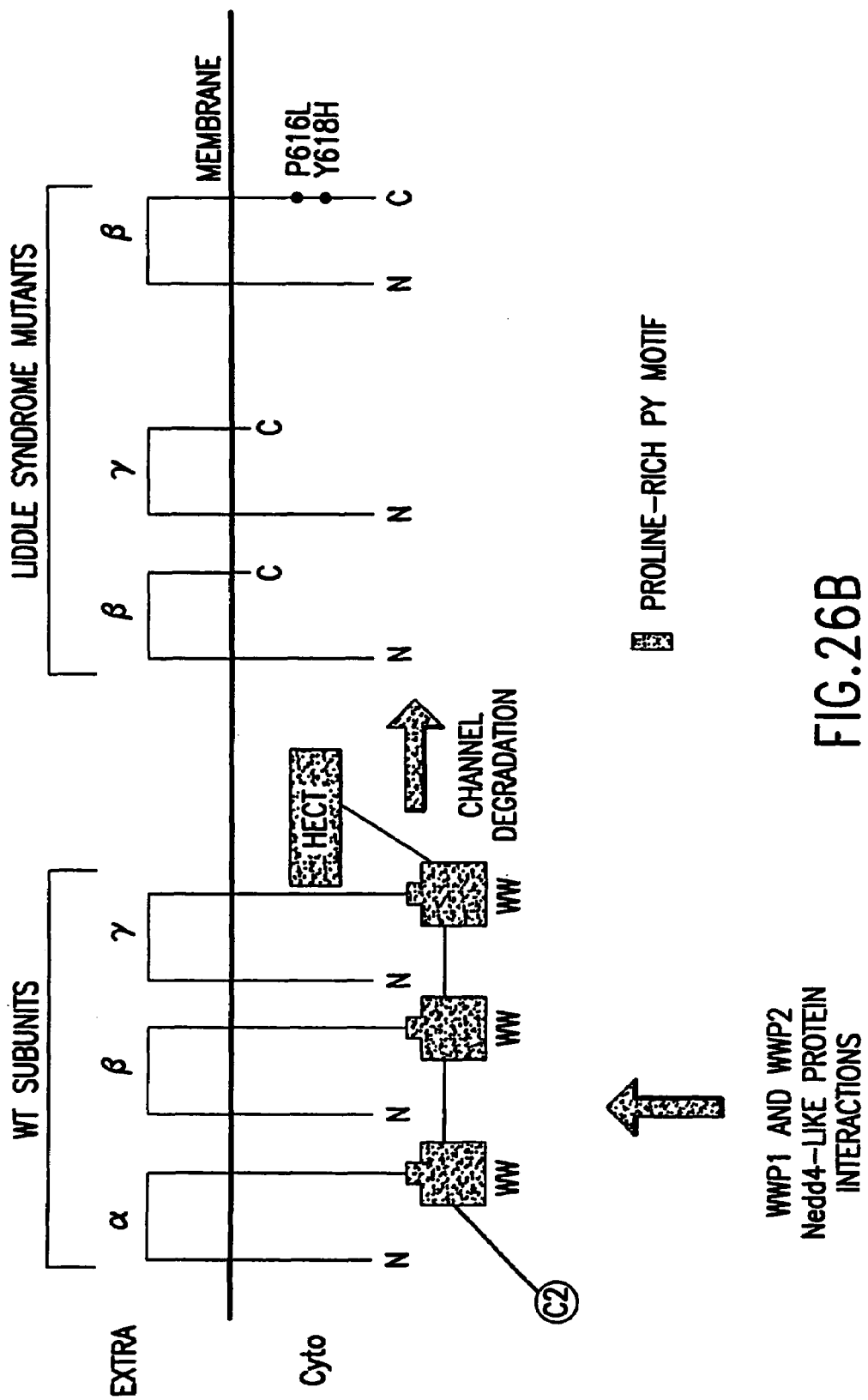

FIG. 26B depicts Nedd-4-like proteins containing WW domains binding to the wild type epithelial Na⁺ channel protein, thereby bringing the HECT domain into the vicinity of the protein where it can mediate ubiquitin tagging of the protein. The ubiquitin tag signals that the protein is to be degraded. This allows for the natural turn-over of the channel protein. However, in Liddle syndrome, the WW Nedd-4 like protein cannot bind to the channel protein due to the missing or mutated proline-rich regions of the channel protein. The protein does not get tagged by ubiquitin and is not degraded. The results in an overexpression of the channel protein in Liddle syndrome patients.

FIG. 27 shows the sequences of WW domain binding clones obtained by screening random or biased libraries with WWP1.1, WWP1.4 or WWP3 domains to obtain peptide recognition units ("ligands") for analyzing specificities of the WW domains.

5. DETAILED DESCRIPTION OF THE INVENTION

The present invention relates to polypeptides having a WW domain, methods of identifying and using these polypeptides and derivatives thereof, and nucleic acids encoding the foregoing. The detailed description that follows is provided to elucidate the invention further and to assist further those of ordinary skill who may be interested in practicing particular aspects of the invention.

First, certain definitions are in order. Accordingly, the term "polypeptide" refers to a molecule comprised of amino acid residues joined by peptide (i.e., amide) bonds and includes proteins and peptides. Hence, the polypeptides of the present invention may have single or multiple chains of covalently linked amino acids and may further contain intrachain or interchain linkages comprised of disulfide bonds. Some polypeptides may also form a subunit of a multiunit macromolecular complex. Naturally, the polypeptides can be expected to possess conformational preferences and to exhibit a three-dimensional structure. Both the conformational preferences and the three-dimensional structure will usually be defined by the polypeptide's primary (i.e., amino acid) sequence and/or the presence (or absence) of disulfide bonds or other covalent or non-covalent intrachain or interchain interactions.

The polypeptides of the present invention can be any size. As can be expected, the polypeptides can exhibit a wide variety of molecular weights, some exceeding 150 to 200 kilodaltons (kD). Typically, the polypeptides may have a molecular weight ranging from about 5,000 to about 100,000 daltons. Still others may fall in a narrower range, for example, about 10,000 to about 75,000 daltons, or about 20,000 to about 50,000 daltons.

WW domains tend to be modular in that such domains may occur one or more times in a given polypeptide (or target molecule) or may be found in a family of different polypeptides. When found more than once in a given polypeptide or in different polypeptides, the modular WW domain may possess substantially the same structure, in terms of primary sequence and/or three-dimensional conformation, or may contain slight or great variations or modifications among the different versions of the WW domain of interest.

What is important, however, is that these related WW domains retain at least one of the functional aspects of the WW domain of interest present in the target molecule. It is stressed that, indeed, it is this functional relationship among two or more possible versions of a WW domain which may be identified, defined, and exploited by the methods of the present invention. In a preferred aspect, the function of interest is the ability to bind to a molecule (e.g., a peptide) of interest.

The present invention provides a general strategy by which recognition units that bind to a WW domain-containing protein can be used to screen expression libraries of genes (e.g., cDNA, genomic libraries) systematically for novel WW domain-containing proteins. In specific embodiments, the recognition units are prior isolated from a random peptide library, or are known peptide recognition units, or are recognition units that are identified by database searches for sequences having homology to a peptide recognition unit having the binding specificity of interest.

In the prior art, novel genes (and thus their encoded protein products) are most commonly identified from cDNA libraries. Generally, an appropriate cDNA library is screened with a probe that is either an oligonucleotide or an antibody. In either case, the probe must be specific enough for the gene that is to be identified to pick that gene out from a vast background of non-relevant genes in the library. It is this need for a specific probe that is the highest hurdle that must be overcome in the prior art identification of novel genes. Another method of identifying genes from cDNA libraries is through use of the polymerase chain reaction (PCR) to amplify a segment of a desired gene from the library. PCR requires that oligonucleotides having sequence similarity to the desired gene be available.

If the probe used in prior art methods is a nucleic acid, the cDNA library may be screened without the need for expressing any protein products that might be encoded by the cDNA clones. If the probe used in prior art methods is an antibody, then it is necessary to build the cDNA library into a suitable expression vector. For a comprehensive discussion of the art of identifying genes from cDNA libraries, see Sambrook, Fritsch, and Maniatis, "Construction and Analysis of cDNA Libraries," Chapter 8 in Cloning, A Laboratory Manual, 2d ed., Cold Spring Harbor Laboratory Press, 1989. See also Sambrook, Fritsch, and Maniatis, "Screening Expression Libraries with Antibodies and Oligonucleotides," Chapter 12 in Cloning, A Laboratory Manual, 2d ed., Cold Spring Harbor Laboratory Press, 1989.

As an alternative to cDNA libraries, genomic libraries may be used. When genomic libraries are used in prior art methods, the probe is virtually always a nucleic acid probe. See Sambrook, Fritsch, and Maniatis, "Analysis and Cloning of Eukaryotic Genomic DNA," Chapter 9 in Cloning, A Laboratory Manual, 2d ed., Cold Spring Harbor Laboratory Press, 1989.

In the prior art, nucleic acid probes used in screening libraries are often based upon the sequence of a known gene that is thought to be homologous to a gene that it is desired to isolate. The success of the procedure depends upon the degree of homology between the probe and the target gene being sufficiently high. Probes based upon the sequences of known WW domains had limited value because, while the sequences of the WW domains were similar enough to allow for their recognition as shared domains, the similarity was not so high that probes could be designed that could be used to screen cDNA or genomic libraries for genes containing the WW domains with a reasonable expectation of success. See FIG. 5 for an illustration of the level of primary sequence homology among WW domains.

PCR may also be used to identify genes from genomic libraries. However, as in the case of using PCR to identify genes from cDNA libraries, this requires that oligonucleotides having sequence similarity to the desired gene be available.

Using the screening methods provided by the present invention, DNA encoding proteins having a desired WW domain can be identified by functional binding specificity to recognition units. By virtue of an ease in specificity of binding requirements conferred by the screening methods of the present invention, many novel, functionally homologous, WW domain-containing proteins can be identified. Although not intending to be bound by any mechanistic explanation, this ease in binding specificity is believed to be the result of the use of a multivalent recognition unit used to screen the gene library, preferably of a valency greater than bivalent, more preferably tetravalent or greater, and most preferably the streptavidin-biotinylated peptide recognition unit complex.

Figure 1:
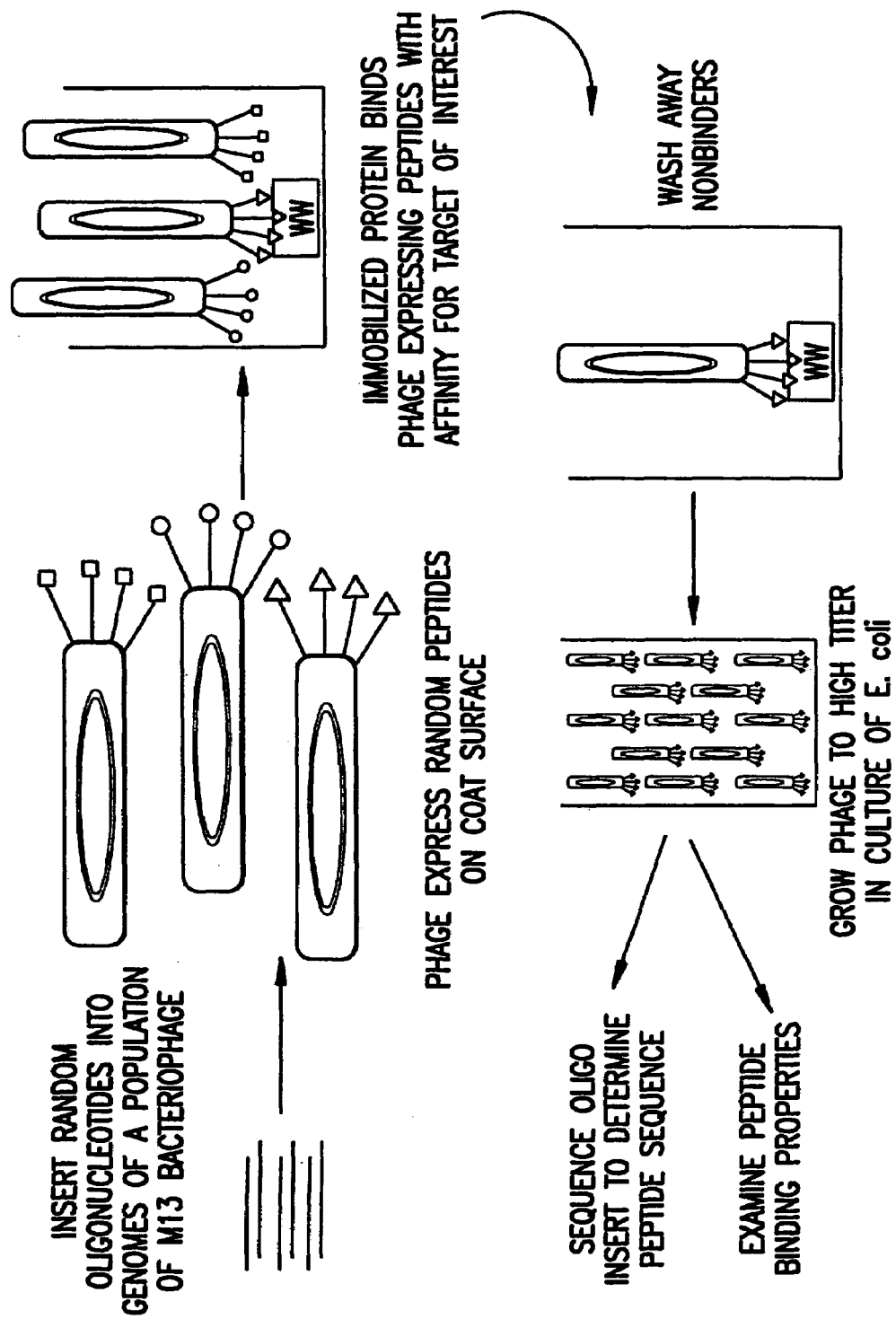
Figure 2:
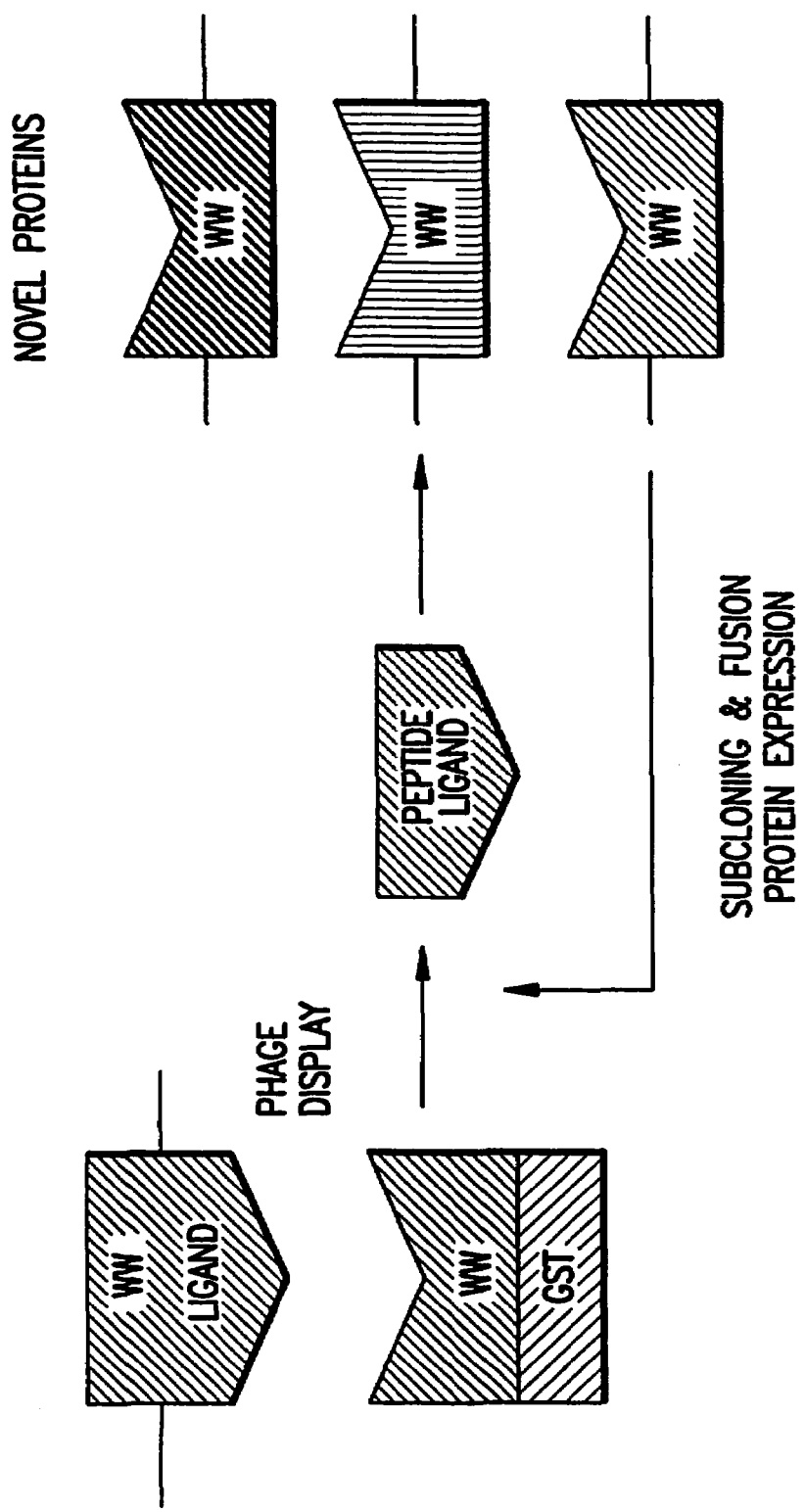
Figure 3:
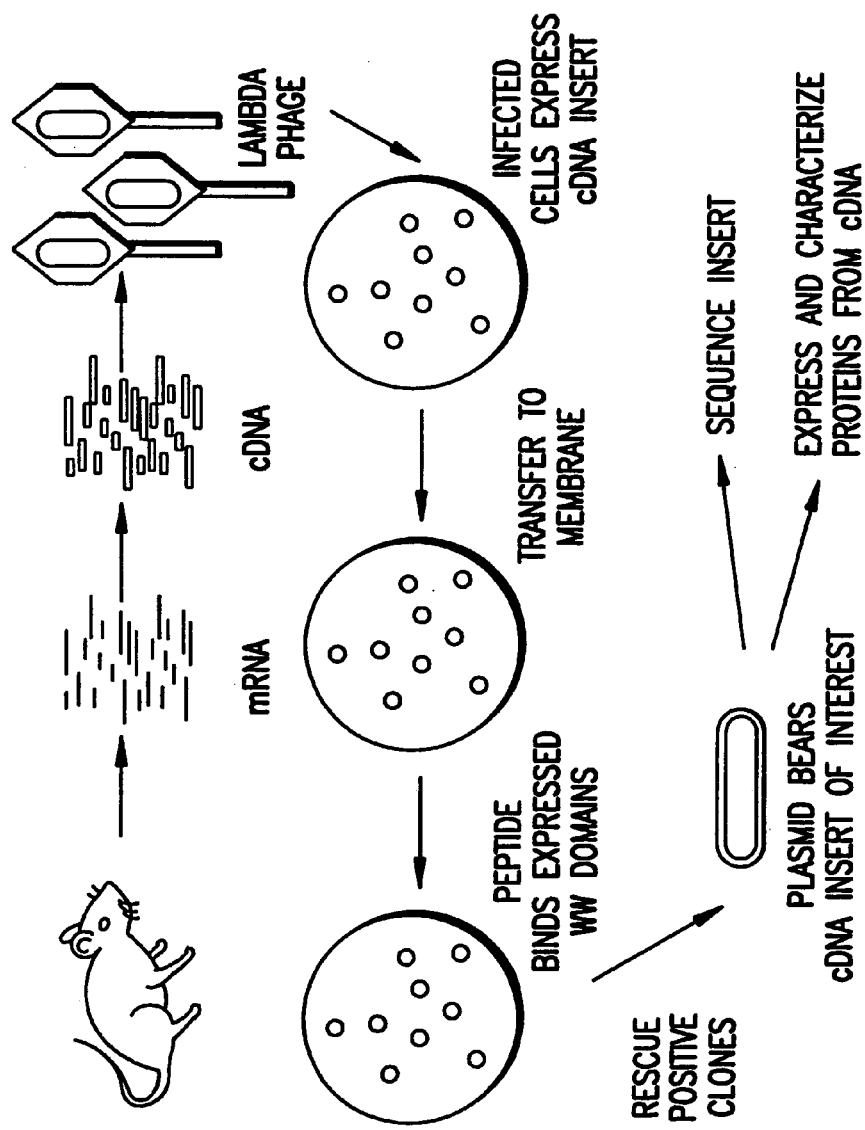
Figure 4:
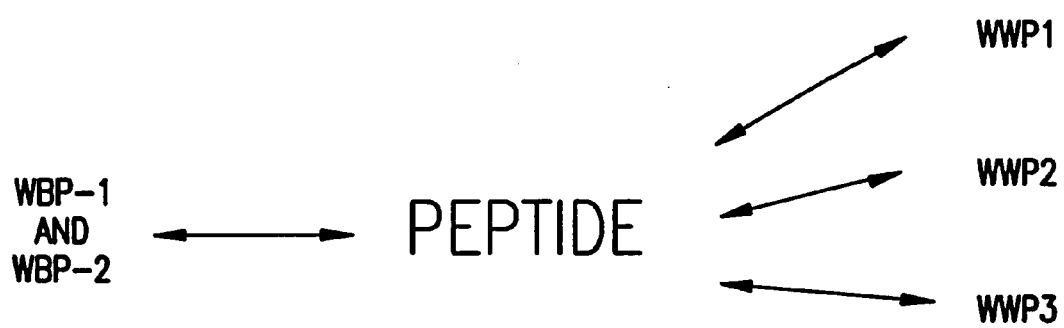

In one particular embodiment of the invention, exhaustive screening of proteins having a WW domain involves an iterative process by which recognition units for WW domains identified in the first round of screening are used to detect WW domain-containing proteins in successive expression library screens (see FIGS. 2 and 6B). This strategy enables one to search "sequence space" in what might be thought of as ever-widening circles with each successive cycle. This iterative strategy can be initiated even when only one WW domain-containing protein and recognition unit are available.

The present invention provides polypeptides comprising novel HECT domains and nucleic acids encoding those polypeptides. In particular, the present invention provides a novel HECT domain having an amino acid sequence selected from the group consisting of SEQ ID NOs:115, 116, 124, and 130. Also provided are nucleic acids encoding those novel HECT domains. The novel HECT domains of the present invention can be used to identify and isolate recognition units that can be used to identify and isolate additional HECT domain containing polypeptides.

5.1. Discovery of Novel Genes and Polypeptides Containing WW Domains

The present invention makes possible the dentification of one or more polypeptides (in particular, a "family" of polypeptides, including the target molecule) that contain a WW domain that either corresponds to or is the functional equivalent of a WW domain present in a predetermined target molecule.

The present invention provides a mechanism for the rapid identification of genes (e.g., cDNAs) encoding virtually any WW domain. By screening cDNA libraries or other sources of polypeptides for recognition unit binding rather than sequence similarity, the present invention circumvents the limitations of conventional DNA-based screening methods and allows for the identification of highly disparate protein sequences possessing equivalent functional activities. The ability to isolate entire repertoires of proteins containing particular modular WW domains will prove invaluable both in molecular biological investigations of the genome and in bringing new targets into drug discovery programs.

It should likewise be apparent that a wide range of polypeptides having a WW domain can be identified by the process of the invention, which process comprises:

(a) contacting a multivalent recognition unit complex with a plurality of polypeptides; and (b) identifying a polypeptide having a selective binding affinity for said recognition unit complex, in which the recognition unit selectively binds a WW domain.

In a specific embodiment, the process comprises:

(a) contacting a multivalent recognition unit complex with a plurality of polypeptides from which it is desired to identify a polypeptide having selective binding affinity for the recognition unit, in which the valency of the recognition unit in the complex is at least two, or at least four, in which the recognition unit selectively binds a WW domain; and (b) identifying, and preferably recovering, a polypeptide having a selective binding affinity for the recognition unit complex.

In another specific embodiment, the process comprises a method of identifying a polypeptide having a WW domain comprising:

(a) contacting a multivalent recognition unit complex, which complex comprises (i) avidin or streptavidin, and (ii) biotinylated recognition units, with a plurality of polypeptides from a cDNA expression library, in which the recognition unit is a peptide having in the range of 6 to 60 amino acid residues and which selectively binds a WW domain; and (b) identifying a polypeptide having a selective binding affinity for said recognition unit complex.

In another embodiment, the present invention includes a method of identifying one or more novel polypeptides having a WW domain, said method comprising:

(a) identifying a recognition unit having a selective affinity for the WW domain by screening a peptide library with the WW domain;

(b) producing said recognition unit;

(c) contacting said recognition unit with a source of polypeptides; and (d) identifying one or more novel polypeptides having a selective affinity for said recognition unit, which polypeptides comprise a WW domain.

In another specific embodiment, the process comprises a method of identifying a polypeptide having a WW domain of interest or a functional equivalent thereof comprising:

(a) screening a random peptide library to identify a peptide that selectively binds a WW domain of interest; and (b) screening a cDNA or genomic expression library with said peptide or a binding portion thereof to identify a polypeptide that selectively binds said peptide.

In a specific embodiment of the above method, the screening step (b) is carried out by use of said peptide in the form of multiple antigen peptides (MAP) or by use of said peptide cross-linked to bovine serum albumin or keyhole limpet hemocyanin.

In another specific embodiment, the process comprises a method of identifying a polypeptide having a WW domain of interest or a functional equivalent thereof comprising:

(a) screening a random peptide library to identify a plurality of peptides that selectively bind a WW domain of interest;

(b) determining at least part of the amino acid sequences of said peptides;

(c) determining a consensus sequence based upon the determined amino acid sequences of said peptides; and (d) screening a cDNA or genomic expression library with a peptide comprising the consensus sequence to identify a polypeptide that selectively binds said peptide.

In another specific embodiment, the process comprises a method of identifying a polypeptide having a WW domain, which can be the WW domain of interest or a functional equivalent thereof, comprising:

(a) screening a random peptide library to identify a first peptide that selectively binds a WW domain of interest;

(b) determining at least part of the amino acid sequence of said first peptide;

(c) searching a database containing the amino acid sequences of a plurality of expressed natural proteins to identify a protein containing an amino acid sequence homologous to the amino acid sequence of said first peptide; and (d) screening a cDNA or genomic expression library with a second peptide comprising the sequence of said protein that is homologous to the amino acid sequence of said first peptide.

The polypeptide identified by the above-described methods thus should contain the WW domain of interest or a functional equivalent thereof (that is, have a WW domain that is identical, or have a WW domain that differs in sequence but is capable of binding to the same recognition unit). In a particular embodiment, the polypeptide identified is a novel polypeptide. In a preferred embodiment, the recognition unit that is used to form the multivalent recognition unit complex is isolated or identified from a random peptide library.

The present invention provides amino acid sequences of any DNA sequences encoding novel proteins containing WW domains. The WW domains vary in sequence but retain binding specificity to a WW domain recognition unit. Also provided are fragments and derivatives of the novel proteins containing WW domains as well as DNA sequences encoding the same. It will be apparent to one of ordinary skill in the art that also provided are proteins that vary slightly in sequence from the novel proteins by virtue of conservative amino acid substitutions. It will also be apparent to one of ordinary skill in the art that the novel proteins may be expressed recombinantly by standard methods. The novel proteins may also be expressed as fusion proteins with a variety of other proteins, e.g., glutathione S-transferase.

The present invention provides a purified polypeptide comprising a WW domain, said WW domain having an amino acid sequence selected from the group consisting of: SEQ ID NOs: 30–38, and 127–129. Also provided is a purified DNA encoding the polypeptide.

Also provided is a purified polypeptide comprising a WW domain, said polypeptide having an amino acid sequence selected from the group consisting of SEQ ID NOs: 46, 48, 50, and 126. Also provided is a purified DNA encoding the polypeptide.

Also provided is a purified DNA encoding a WW domain, said DNA having a sequence selected from the group consisting of SEQ ID NOs: 45, 47, 49, and 125. Also provided is a nucleic acid vector comprising this purified DNA. Also provided is a recombinant cell containing this nucleic acid vector.

Also provided is a purified DNA encoding a polypeptide having an amino acid sequence selected from the group consisting of: SEQ ID NOs: 46, 48, 50, and 126. Also provided is a nucleic acid vector comprising this purified DNA. Also provided is a recombinant cell containing this nucleic acid vector.

Also provided is a purified DNA encoding a polypeptide comprising an amino acid sequence selected from the group consisting of: SEQ ID NOs: 30–38 and 127–129. Also provided is a nucleic acid vector comprising this purified DNA. Also provided is a recombinant cell containing this nucleic acid vector.

Also provided is a purified molecule comprising a WW domain of a polypeptide having an amino acid sequence selected from the group consisting of: SEQ ID NO: 46, 48, 50, and 126.

Also provided is a fusion protein comprising (a) an amino acid sequence comprising a WW domain of a polypeptide having the amino acid sequence of SEQ ID NO: 46, 48, 50, 126, 30–38, and 127–129, joined via a peptide bond to (b) an amino acid sequence of at least six, or ten, or twenty, amino acids from a different polypeptide. Also provided is a purified DNA encoding the fusion protein. Also provided is a nucleic acid vector comprising the purified DNA encoding the fusion protein. Also provided is a recombinant cell containing this nucleic acid vector. Also provided is a method of producing this fusion protein comprising culturing a recombinant cell containing a nucleic acid vector encoding said fusion protein such that said fusion protein is expressed, and recovering the expressed fusion protein.

The present invention also provides a purified nucleic acid hybridizable to a nucleic acid having a sequence selected from the group consisting of: SEQ ID NOs: 45, 47, 49, and 125.

The present invention also provides antibodies to a polypeptide having an amino acid sequence selected from the group consisting of: SEQ ID NOs: 30–38, and 127–129.

The present invention also provides antibodies to a polypeptide having an amino acid sequence selected from the group consisting of SEQ ID NOs: 46, 48, 50, and 126.

It has been demonstrated by way of example herein that recognition units that comprise WW domain ligands derived from combinatorial peptide libraries may be used in the methods of the present invention as probes for the rapid discovery of novel proteins containing WW functional domains. The methods of the present invention require no prior knowledge of the characteristics of a WW domain's natural cellular ligand to initiate the process of discovery. One needs only enough purified WW domain-containing protein (by way of example, 1–5 μg) to select peptides from a random peptide library. In addition, because the methods of the present invention identify novel proteins from cDNA expression libraries based only on their binding properties, low primary sequence identity between the target WW domain and the WW domains of the novel proteins discovered need not be a limitation, provided some functional similarity between these WW domains is conserved. Also, the methods of the present invention are rapid, require inexpensive reagents, and employ simple and well established laboratory techniques.

Using these methods, six different WW domain-containing proteins have been identified, of which four have not been previously described. These novel proteins are described more fully in Sections 6.1 and 6.1.1. The high incidence of novel proteins identified by the methods of the present invention indicates that a large number of WW domain-containing proteins remain to be discovered.

One of ordinary skill in the art would recognize that the above-described novel proteins need not be used in their entirety in the various applications of those proteins described herein. In many cases it will be sufficient to employ that portion of the novel protein that contains the WW domain. Such exemplary portions of WW domain-containing proteins are shown in FIG. 5. Accordingly, the present invention provides derivatives (e.g., fragments and molecules comprising these fragments) of novel proteins that contain WW domains, e.g., as shown in FIG. 5. Nucleic acids encoding these fragments or other derivatives are also provided.

5.1.1. WW Domains

WW domains of interest in the practice of the present invention can take many forms and may perform a variety of functions. For example, such WW domains may be involved in a number of cellular, biochemical, or physiological processes, such as cellular signal transduction, transcriptional regulation, protein ubiquitination, cell adhesion, cytoskeletal organization, and the like. In particular embodiments of the present invention, the WW domains of interest may be found in such proteins as YAP, Nedd-4, RSP5, dystrophin, utrophin, ess1, FE65, HUMORF1, and many others.

In one embodiment of the invention, a suitable target molecule containing the chosen WW domain of interest is selected. A number of proteins may be selected as the target molecule, including but not limited to: YAP, Nedd-4, RSP5, dystrophin, utrophin, ess1, FE65, and HUMORF1. Alternatively, a portion of the above-mentioned proteins comprising the WW domain may be chosen as the target molecule.

5.1.2. Recognition Units

By the phrase "recognition unit," is meant any molecule having a selective affinity for the WW domain of the target molecule and, preferably, having a molecular weight of up to about 20,000 daltons. In a particular embodiment of the invention, the recognition unit has a molecular weight that ranges from about 100 to about 10,000 daltons.

Accordingly, preferred recognition units of the present invention possess a molecular weight of about 100 to about 5,000 daltons, preferably from about 100 to about 2,000 daltons, and most preferably from about 500 to about 1,500 daltons. As described further below, a recognition unit of the present invention can be a peptide, a carbohydrate, a nucleoside, an oligonucleotide, any small synthetic molecule, or a natural product. When the recognition unit is a peptide, the peptide preferably contains about 6 to about 50 amino acid residues.

When the recognition unit is a peptide, the peptide can have less than about 140 amino acid residues; preferably, the peptide has less than about 100 amino acid residues; preferably, the peptide has less than about 70 amino acid residues; preferably the peptide has 20 to 50 amino acid residues; most preferably, the peptide has about 6 to 60 amino acid residues.

The peptide recognition units are preferably in the form of a multivalent peptide complex comprising avidin or streptavidin (optionally conjugated to a label such as alkaline phosphatase or horseradish peroxidase) and biotinylated peptides.

According to the present invention, a recognition unit (preferably in the form of a multivalent recognition unit complex) is used to screen a plurality of expression products of gene sequences containing nucleic acid sequences that are present in native RNA or DNA (e.g., cDNA library, genomic library).

The step of choosing a recognition unit can be accomplished in a number of ways that are known to those of ordinary skill, including but not limited to screening cDNA libraries or random peptide libraries for a peptide that binds to the WW domain of interest. Essentially, screening cDNA libraries or random peptide libraries for a peptide that binds to a WW domain can be accomplished in the same manner as for screening cDNA libraries or random peptide libraries for a peptide that binds to an SH3 domain. See, e.g., Yu et al., 1994, Cell 76, 933–945; Sparks et al., 1994, J. Biol. Chem. 269, 23853–23856; Sparks et al., 1996, Proc. Natl. Acad. Sci. USA 93:1540–1544 for screening of peptide libraries to discover peptides that bind to SH3 domains. Alternatively, a small molecule or drug may be known to those of ordinary skill to bind to a certain target molecule containing a WW domain. The recognition unit can even be synthesized from a lead compound, which again may be a peptide, carbohydrate, oligonucleotide, small drug molecule, or the like. The recognition unit can also be identified for use by doing searches (preferably via database) for molecules having homology for other, known recognition unit(s) having the ability to selectively bind to a WW domain.

In a specific embodiment, the step of selecting a recognition unit for use can be effected by, e.g., the use of diversity libraries, such as random or combinatorial peptide or nonpeptide libraries which can be screened for molecules that specifically bind to WW domains. Many libraries are known in the art that can be used, e.g., chemically synthesized libraries, recombinant (e.g., phage display libraries), and in vitro translation-based libraries.

Examples of chemically synthesized libraries are described in Fodor et al., 1991, Science 251:767–773; Houghten et al., 1991, Nature 354:84–86; Lam et al., 1991, Nature 354:82–84; Medynski, 1994, Bio/Technology 12:709–710; Gallop et al., 1994, J. Medicinal Chemistry 37(9):1233–1251; Ohlmeyer et al., 1993, Proc. Natl. Acad. Sci. USA 90:10922–10926; Erb et al., 1994, Proc. Natl. Acad. Sci. USA 91:11422–11426; Houghten et al., 1992, Biotechniques 13:412; Jayawickreme et al., 1994, Proc. Natl. Acad. Sci. USA 91:1614–1618; Salmon et al., 1993, Proc. Natl. Acad. Sci. USA 90:11708–11712; PCT Publication No. WO 93/20242; and Brenner and Lerner, 1992, Proc. Natl. Acad. Sci. USA 89:5381–5383.

Examples of phage display libraries are described in Scott and Smith, 1990, Science 249:386–390; Devlin et al., 1990, Science, 249:404–406; Christian, R. B., et al., 1992, J. Mol. Biol. 227:711–718); Lenstra, 1992, J. Immunol. Meth. 152: 149–157; Kay et al., 1993, Gene 128:59–65; and PCT Publication No. WO 94/18318 dated Aug. 18, 1994.

In vitro translation-based libraries include but are not limited to those described in PCT Publication No. WO 91/05058 dated Apr. 18, 1991; and Mattheakis et al., 1994, Proc. Natl. Acad. Sci. USA 91:9022–9026.

By way of examples of nonpeptide libraries, a benzodiazepine library (see e.g., Bunin et al., 1994, Proc. Natl.

Acad. Sci. USA 91:4708–4712) can be adapted for use. Peptoid libraries (Simon et al., 1992, Proc. Natl. Acad. Sci. USA 89:9367–9371) can also be used. Another example of a library that can be used, in which the amide functionalities in peptides have been permethylated to generate a chemically transformed combinatorial library, is described by Ostresh et al. (1994, Proc. Natl. Acad. Sci. USA 91:11138–11142).

The variety of non-peptide libraries that are useful in the present invention is great. For example, Ecker and Crooke, 1995, Bio/Technology 13:351–360 list benzodiazepines, hydantoins, piperazinediones, biphenyls, sugar analogs, β-mercaptoketones, arylacetic acids, acylpiperidines, benzopyrans, cubanes, xanthines, aminimides, and oxazolones as among the chemical species that form the basis of various libraries.

Non-peptide libraries can be classified broadly into two types: decorated monomers and oligomers. Decorated monomer libraries employ a relatively simple scaffold structure upon which a variety functional groups is added. Often the scaffold will be a molecule with a known useful pharmacological activity. For example, the scaffold might be the benzodiazepine structure.

Non-peptide oligomer libraries utilize a large number of monomers that are assembled together in a ways that create new shapes that depend on the order of the monomers. Among the monomer units that have been used are carbamates, pyrrolinones, and morpholinos. Peptoids, peptide-like oligomers in which the side chain is attached to the a amino group rather than the a carbon, form the basis of another version of non-peptide oligomer libraries. The first non-peptide oligomer libraries utilized a single type of monomer and thus contained a repeating backbone. Recent libraries have utilized more than one monomer, giving the libraries added flexibility.

Screening the libraries can be accomplished by any of a variety of commonly known methods. See, e.g., the following references, which disclose screening of peptide libraries: Parmley and Smith, 1989, Adv. Exp. Med. Biol. 251: 215–218; Scott and Smith, 1990, Science 249:386–390; Fowlkes et al., 1992; BioTechniques 13:422–427; Oldenburg et al., 1992, Proc. Natl. Acad. Sci. USA 89:5393–5397; Yu et al., 1994, Cell 76:933–945; Staudt et al., 1988, Science 241:577–580; Bock et al., 1992, Nature 355:564–566; Tuerk et al., 1992, Proc. Natl. Acad. Sci. USA 89:6988–6992; Ellington et al., 1992, Nature 355:850–852; U.S. Pat. No. 5,096,815, U.S. Pat. No. 5,223,409, and U.S. Pat. No. 5,198,346, all to Ladner et al.; Rebar and Pabo, 1993, Science 263:671–673; and PCT Publication No. WO 94/18318.

In a specific embodiment, screening to identify a recognition unit can be carried out by contacting the library members with a WW domain immobilized on a solid phase and harvesting those library members that bind to the WW domain. Examples of such screening methods, termed "panning" techniques are described by way of example in Parmley and Smith, 1988, Gene 73:305–318; Fowlkes et al., 1992, BioTechniques 13:422–427; PCT Publication No. WO 94/18318; and in references cited hereinabove.

In another embodiment, the two-hybrid system for selecting interacting proteins in yeast (Fields and Song, 1989, Nature 340:245–246; Chien et al., 1991, Proc. Natl. Acad. Sci. USA 88:9578–9582) can be used to identify recognition units that specifically bind to WW domains. Where the recognition unit is a peptide, the peptide can be conveniently selected from any peptide library, including random peptide libraries, combinatorial peptide libraries, or biased peptide libraries. The term "biased" is used herein to mean that the method of generating the library is manipulated so as to restrict one or more parameters that govern the diversity of the resulting collection of molecules, in this case peptides.

Thus, a truly random peptide library would generate a collection of peptides in which the probability of finding a particular amino acid at a given position of the peptide is the same for all 20 amino acids. A bias can be introduced into the library, however, by specifying, for example, that a lysine occur every fifth amino acid or that positions 4, 8, and 9 of a decapeptide library be fixed to include only arginine. Clearly, many types of biases can be contemplated, and the present invention is not restricted to any particular bias. Furthermore, the present invention contemplates specific types of peptide libraries, such as phage displayed peptide libraries and those that utilize a DNA construct comprising a lambda phage vector with a DNA insert.

As mentioned above, in the case of a recognition unit that is a peptide, the peptide may have about 6 to less than about 60 amino acid residues, preferably about 6 to about 25 amino acid residues, and most preferably, about 6 to about 15 amino acids. In another embodiment, a peptide recognition unit has in the range of 20–100 amino acids, or 20–50 amino acids.

The selected recognition unit can be obtained by chemical synthesis or recombinant expression. Chemical synthesis may be accomplished using techniques known in the art.

By example, and not by way of limitation, peptides may be synthesized using a variation of standard solid phase Fmoc peptide chemistry (Knorr et al., 1989, Tetrahedron Lett. 30:1927–1930) on standard support resins, including but not limited to, polystyrene or TentaGel® (Tubingen, Germany). Product yield can be increased by varying DMSO (dimethylsulfoxide) solvent mixtures used in the synthesis. Specifically proline rich regions require the use of 50% DMSO as a co-solvent with DMF (N,N-dimethylformamide) or NMP (N-methylpyrralidone) in order to obtain reasonable yields. Additionally, with respect to biotinylation, biotin is only marginally soluble in neat DMF or NMP, so this reagent was dissolved in DMSO and then diluted to 50% in NMP or DMF before coupling. Further, depending on the particular ligand, biotin sometimes requires a spacer moiety between it and the ligand. Although many spacers are commonly used in the synthesis of biotinyl peptides, it was found necessary to incorporate lysine in the spacer region in order to improve solubility in aqueous solvent systems. Specifically, in a typical 15–20 mer proline rich peptide, it was found that solubility was best when the peptide contained three or more basic moieties, although two acidic moieties could substitute for any given basic moiety and preserve solubility.

The selected recognition units, whether obtained by chemical synthesis or recombinant expression, are preferably purified prior to use in screening a plurality of gene sequences.

5.1.3. Screening a Source of Polypeptides

After the recognition unit is chosen, the recognition unit is then contacted with a plurality of polypeptides, preferable containing a WW domain. In a particular embodiment of the invention, the plurality of polypeptides is obtained from a polypeptide expression library. The polypeptide expression library may be obtained, in turn, from cDNA, fragmented genomic DNA, and the like. In a specific embodiment, the library that is screened is a cDNA library of total poly A+ RNA of an organism, in general, or of a particular cell or tissue type or developmental stage or disease condition or stage. The expression library may utilize a number of expression vehicles known to those of ordinary skill, including but not limited to, recombinant bacteriophage, lambda phage, M13, a recombinant plasmid or cosmid, and the like.

The plurality of polypeptides or the DNA sequences encoding the same may be obtained from a variety of natural or unnatural sources, such as a procaryotic or a eucaryotic cell, either a wild type, recombinant, or mutant. In particular, the plurality of polypeptides may be endogenous to microorganisms, such as bacteria, yeast, or fungi, to a virus, to an animal (including mammals, invertebrates, reptiles, birds, and insects) or to a plant cell.

In addition, the plurality of polypeptides may be obtained from more specific sources, such as the surface coat of a virion particle, a particular cell lysate, a tissue extract, or they may be restricted to those polypeptides that are expressed on the surface of a cell membrane.

Moreover, the plurality of polypeptides may be obtained from a biological fluid, particularly from humans, including but not limited to blood, plasma, serum, urine, feces, mucus, semen, vaginal fluid, amniotic fluid, or cerebrospinal fluid. The plurality of polypeptides may even be obtained from a fermentation broth or a conditioned medium, including all the polypeptide products secreted or produced by the cells previously in the broth or medium.

The step of contacting the recognition unit with the plurality of polypeptides may be effected in a number of ways. For example, one may contemplate immobilizing the recognition unit on a solid support and bringing a solution of the plurality of polypeptides in contact with the immobilized recognition unit. Such a procedure would be akin to an affinity chromatographic process, with the affinity matrix being comprised of the immobilized recognition unit. The polypeptides having a selective affinity for the recognition unit can then be purified by affinity selection. The nature of the solid support, process for attachment of the recognition unit to the solid support, solvent, and conditions of the affinity isolation or selection procedure would depend on the type of recognition unit in use but would be largely conventional and well known to those of ordinary skill in the art. Moreover, the valency of the recognition unit in the recognition unit complex used to screen the polypeptides is believed to affect the specificity of the screening step, and thus the valency can be chosen as appropriate in view of the desired specificity (see Sections 5.2 and 5.2.1).

Alternatively, one may also separate the plurality of polypeptides into substantially separate fractions comprising individual polypeptides. For instance, one can separate the plurality of polypeptides by gel electrophoresis, column chromatography, or like method known to those of ordinary skill for the separation of polypeptides. The individual polypeptides can also be produced by a transformed host cell in such a way as to be expressed on or about its outer surface. Individual isolates can then be "probed" by the recognition unit, optionally in the presence of an inducer should one be required for expression, to determine if any selective affinity interaction takes place between the recognition unit and the individual clone. Prior to contacting the recognition unit with each fraction comprising individual polypeptides, the polypeptides could first be transferred to a solid support for additional convenience. Such a solid support may simply be a piece of filter membrane, such as one made of nitrocellulose or nylon.

In this manner, positive clones could be identified from a collection of transformed host cells of an expression library, which harbor a DNA construct encoding a polypeptide having a selective affinity for the recognition unit. The polypeptide produced by the positive clone includes the WW domain of interest or a functional equivalent thereof. Furthermore, the amino acid sequence of the polypeptide having a selective affinity for the recognition unit can be determined directly by conventional means or the coding sequence of the DNA encoding the polypeptide can frequently be determined more conveniently. The primary sequence can then be deduced from the corresponding DNA sequence.

If the amino acid sequence is to be determined from the polypeptide itself, one may use microsequencing techniques. The sequencing technique may include mass spectroscopy.

In certain situations, it may be desirable to wash away any unbound recognition unit from a mixture of the recognition unit and the plurality of polypeptides prior to attempting to determine or to detect the presence of a selective affinity interaction (i.e., the presence of a recognition unit that remains bound after the washing step). Such a wash step may be particularly desirable when the plurality of polypeptides is bound to a solid support.

As can be anticipated, the degree of selective affinities observed varies widely, generally falling in the range of about 1 nm to about 1 mM. In preferred embodiments of the present invention, the selective affinity falls on the order of about 10 nM to about 100 µM, more preferably on the order of about 100 nM to about 10 µM, and most preferably on the order of about 100 nM to about 1 µM.

5.2. Specificity of Recognition Units

A particular recognition unit may have fairly generic selectivity for several members (e.g., three or four or more) of a "panel" of polypeptides having a WW domain (the same WW domain or different versions of a WW domain or functional equivalents of a WW domain of interest) or a fairly specific selectivity for only one or two, or possibly three, of the polypeptides among a "panel" of same. Furthermore, multiple recognition units, each exhibiting a range of selectivities among a "panel" of polypeptides can be used to identify an increasingly comprehensive set of additional polypeptides that include a WW domain.

Hence, in a population of related polypeptides, the WW domains of each member may be schematically represented by a circle. See, by way of example, FIG. 6A. The circle of one polypeptide may overlap with that of another polypeptide. Such overlaps may be few or numerous for each polypeptide. A particular recognition unit, A, may recognize or interact with a portion of the circle of a given polypeptide which does not overlap with any other circle. Such a recognition unit would be fairly specific to that polypeptide. On the other hand, a second recognition unit, B, may recognize a region of overlap between two or more polypeptides. Such a recognition unit would consequently be less specific than the recognition unit A and may be characterized as having a more generic specificity depending on the number of polypeptides that it recognizes or interacts with.

It should also be apparent to those of ordinary skill that any number of B-type recognition units ($B_1$, $B_2$, $B_3$, etc.) can be present, each recognizing different "panels" of polypeptides. Hence, the use of multiple recognition units provides an increasingly more exhaustive population of polypeptides, each of which exhibits a variation or evolution in the WW domain present in the initial target molecule. It should also be apparent to one that the present method can be applied in an iterative fashion, such that the identification of a particular polypeptide can lead to the choice of another recognition unit. See, e.g., FIG. 6B. Use of this new recognition unit will lead, in turn, to the identification of other polypeptides that contain WW domains that enhance the phenotypic and/or genotypic diversity of the population of "related" polypeptides.

Hence, with a given recognition unit, one may observe interaction with only one or two different polypeptides. With other recognition units, one may find three, four, or more selective interactions. In the situation in which only a single interaction is observed, it is likely, though not mandatory, that the selective affinity interaction is between the recognition unit and a replica of the initial target molecule (or a molecule very similar structurally and "functionally" to the initial target molecule).

5.2.1. Effect of the Presentation of the Recognition Unit on the Specificity of the Recognition Unit-WW Domain Interaction The present inventors have found, unexpectedly, that the valency (i.e., whether-it is a monomer, dimer, tetramer, etc.) of the recognition unit that is used to screen an expression library or other source of polypeptides apparently has a marked effect upon which genes or polypeptides are identified from the expression library or source of polypeptides. In particular, the specificity of the recognition unit-WW domain interaction appears to be affected by the valency of the recognition unit in the screening process. By this specificity is meant the selectivity in the WW domains to which the recognition unit will bind in the screening step.

As discussed above, in one embodiment, recognition units are obtained by screening a source of recognition units, e.g., a phage display library, for recognition units that bind to a particular target WW domain. Alternatively, database searches for recognition units with sequence homology to known recognition units can be employed. Of course, if a recognition unit for a particular target WW domain is already known, there is no need to screen a library or other source of recognition units; one can merely synthesize that particular recognition unit. The recognition unit, however obtained, is then used to screen an expression library or other source of polypeptides to identify polypeptides that the recognition unit binds to. A recognition unit that identifies only its target WW domain is a recognition unit that is completely specific. A recognition unit that identifies one or two other polypeptides that do not contain identically the target WW domain, from among a plurality of polypeptides (e.g., of greater than $10^4$, $10^6$, or $10^8$ complexity), in addition to identifying a molecule comprising its target WW domain, is very or highly specific. A recognition unit that identifies most other polypeptides present that do not contain its target WW domain, in addition to identifying its target WW domain, is a non-specific recognition unit. In between very specific recognition units and non-specific recognition units, the present inventors have discovered that there are recognition units that recognize a small number of molecules having WW domains other than their target WW domains. These recognition units are said to have generic specificity.

Thus, there is a "specificity continuum", from completely and very specific through generic to non-specific, that a recognition unit may evince. See FIG. 13 for a depiction of this specificity continuum. The Applicants have discovered that a major factor influencing the specificity exhibited by a recognition unit appears to be the valency of the recognition unit in the complex used to screen the expression library.

Usually, high specificity is considered to be desirable when screening a library. High specificity is exhibited, e.g., by affinity purified polyclonal antisera which, in general, are very specific. Monoclonal antibodies are also very specific. Small peptides in monovalent form, on the other hand, generally give very weak, non-specific signals when used to screen a library; thus, they are considered to be non-specific.

The present inventors have discovered that recognition units in the form of small peptides, in multivalent form, have a specificity midway between the high specificity of antibodies and the low/non-specificity of monovalent peptides. Multivalency of the recognition unit of at least two, in a recognition unit complex used to screen the gene library, is preferred, with a multivalency of at least four more preferred, to obtain a screening wherein specificity is eased but not forfeited. In particular, a multivalent (believed to be tetravalent) recognition unit complex comprising streptavidin or avidin (preferably conjugated to a label, e.g., an enzyme such as alkaline phosphatase or horseradish peroxidase or a fluorogen such as green fluorescent protein) and biotinylated peptide recognition units have an unexpected generic specificity. This allows such peptides to be used to screen libraries to identify classes of polypeptides containing WW domains that are similar but not identical to the peptides' target WW domains. These classes of polypeptides are identified despite the low level of homology at the amino acid level of the WW domains of the members of the classes.

In another specific embodiment, multivalent peptide recognition units may be in the form of multiple antigen peptides (MAP) (Tam, 1989, J. Imm. Meth. 124:53–61; Tam, 1988, Proc. Natl. Acad. Sci. USA 85:5409–5413). In this form, the peptide recognition unit is synthesized on a branching lysyl matrix using solid-phase peptide synthesis methods. Recognition units in the form of MAP may be prepared by methods known in the art (Tam, 1989, J. 1 mm. Meth. 124:53–61; Tam, 1988, Proc. Natl. Acad. Sci. USA 85:5409–5413), or, for example, by a stepwise solid-phase procedure on MAP resins (Applied Biosystems), utilizing methodology established by the manufacturer. MAP peptides may be synthesized comprising (recognition unit peptide)$_2$Lys$_1$, (recognition unit peptide)$_4$Lys$_3$, (recognition unit peptide)$_8$Lys$_6$ or more levels of branching.

The multivalent peptide recognition unit complexes may also be prepared by cross-linking the peptide to a carrier protein, e.g., bovine serum albumin (BSA), keyhole limpet hemocyanin (KLH) by use of known cross-linking reagents. Such cross-linked peptide recognition units may be detected by, e.g., an antibody to the carrier protein or detection of the enzymatic activity of the carrier protein.

Furthermore, the present inventors have discovered what specificity is exhibited by various types of recognition units and their complexes, i.e., where these recognition units and their complexes fall in the specificity continuum. The present inventors have discovered a range of formats for presenting recognition units used to screen libraries. Monovalent peptides, for example, synthesized peptides themselves, are non-specific. A peptide in the form of a bivalent fusion protein with alkaline phosphatase is very specific. The same peptide in the form of a fusion protein with the pIII protein of an M13 derived bacteriophage, expressed on the phage surface, has somewhat less, though still high, specificity. That same peptide when biotinylated in the form of a tetravalent streptavidin-alkaline phosphatase complex has generic specificity. Use of such a generically specific peptide permits the identification of a wide range of proteins from expression libraries or other sources of polypeptides, each protein containing an example of a particular WW domain.

Accordingly, the present invention provides a method of modulating the specificity of a peptide such that the peptide can be used as a recognition unit to screen a plurality of polypeptides, thus identifying polypeptides that have a WW domain. In a specific embodiment, specificity is generic so as to provide for the identification of polypeptides having a WW domain that varies in sequence from that of the target WW domain known to bind the recognition unit under conditions of high specificity. In a particular embodiment, the method comprises forming a tetravalent complex of the biotinylated peptide and streptavidin-alkaline phosphatase prior to use for screening an expression library.

5.3. Kits

The present invention is also directed to an assay kit which can be useful in the screening of drug candidates. In a particular embodiment of the present invention, an assay kit is contemplated which comprises in one or more containers (a) a polypeptide containing a WW domain; and (b) a recognition unit having a selective affinity for the polypeptide. The kit optionally further comprises a detection means for determining the presence of a polypeptide-recognition unit interaction or the absence thereof.

In a specific embodiment, either the polypeptide containing the WW domain or the recognition unit is labeled. wide range of labels can be used to advantage in-the present invention, including but not limited to conjugating the recognition unit to biotin by conventional means. Alternatively, the label may comprise, e.g., a fluorogen, an enzyme, an epitope, a chromogen, or a radionuclide. Preferably, the biotin is conjugated by covalent attachment to either the polypeptide or the recognition unit. The polypeptide or, preferably, the-recognition unit is immobilized on a solid support. The detection means employed to detect the label will depend on the nature of the label and can be any known in the art, e.g., film to detect a radionuclide; an enzyme substrate that gives rise to a detectable signal to detect the presence of an enzyme; antibody to detect the presence of an epitope, etc.

A further embodiment of the assay kit of the present invention includes the use of a plurality of polypeptides, each polypeptide containing a WW domain. The assay kit further comprises at least one recognition unit having a selective affinity for each of the plurality of polypeptides and a detection means for determining the presence of a polypeptide-recognition unit interaction or the absence thereof.

A kit is provided that comprises, in one or more containers, a first molecule comprising a WW domain and a second molecule that binds to the WW domain, i.e., a recognition unit, where the WW domain is a novel WW domain identified by the methods of the present invention.

In the above assay kit, the polypeptide may comprise an amino acid sequence selected from the group consisting of SEQ ID NOs: 12–28 and 29. The polypeptide also may comprise an amino acid sequence selected from the group consisting of SEQ ID NOs: 46, 48, 50, 126, 30–38, and 127–129.

In other embodiments of the above-described assay kit, the recognition unit may be a peptide. The recognition unit may be labeled with e.g., an enzyme, an epitope, a chromogen, or biotin.

The present invention also provides an assay kit comprising in one or more containers:

(a) a plurality of purified different polypeptides, each polypeptide in a separate container and each polypeptide containing a WW domain; and (b) at least one peptide having a selective affinity for the WW domain in each of said plurality of polypeptides, which optionally, if present as more than one peptide, each peptide can also be in a separate container.

The present invention also provides a kit comprising a plurality of purified polypeptides comprising a WW domain, each polypeptide in a separate container, and each polypeptide having a WW domain of a different sequence but capable of displaying the same binding specificity (binding to the same molecule under appropriate conditions).

In the above-described kits, the polypeptides may have an amino acid sequence selected from the group consisting of: SEQ ID NOs: 12–28 and 29. The polypeptides also may have an amino acid sequence selected from the group consisting of: SEQ ID NOs: 46, 48, 50, 126, 30–38, and 127–129.

The molecular components of the kits are preferably purified.

The kits of the present invention may be used in the methods for identifying new drug candidates and determining the specificities thereof that are described in Section 5.4.

5.4. Assays for the Discovery of Potential Drug Candidates and Determining the Specificity Thereof The present invention also provides methods for identifying potential drug candidates (and lead compounds) and determining the specificities thereof. For example, knowing that a polypeptide containing a WW domain and a recognition unit, e.g., a binding peptide, exhibit a selective affinity for each other, one may attempt to identify a drug that can exert an effect on the polypeptide-recognition unit interaction, e.g., either as an agonist or as an antagonist (inhibitor) of the interaction. With this assay, then, one can screen a collection of candidate "drugs" for the one exhibiting the most desired characteristic, e.g., the most efficacious in disrupting the interaction or in competing with the recognition unit for binding to the polypeptide.

Alternatively, one may utilize the different selectivities that a particular recognition unit may exhibit for different polypeptides bearing the same, similar, or functionally equivalent WW domains. Thus, one may tailor the screen to identify drug candidates that exhibit more selective activities directed to specific polypeptide-recognition unit interactions, among the "panel" of possibilities. Thus, for example, a drug candidate may be screened to identify the presence or absence of an effect on particular binding interactions, potentially leading to undesirable side effects.

In one embodiment, the effect of the drug candidate upon multiple, different interacting polypeptide-recognition unit pairs is determined in which at least some of said polypeptides have a WW domain that differs in sequence but is capable of displaying the same binding specificity as the WW domain in another of said polypeptides.

In another embodiment, at least one of said at least one polypeptide or recognition unit contains a consensus WW domain and consensus recognition unit, respectively.

In another embodiment, the drug candidate is an inhibitor of the polypeptide-recognition unit interaction that is identified by detecting a decrease in the binding of polypeptide to recognition unit in the presence of such inhibitor.

In another embodiment, said polypeptide is a polypeptide containing a WW domain produced by a method comprising:

(i) screening a peptide library with a WW domain to obtain one or more peptides that bind the WW domain;

(ii) using one of the peptides from step (i) to screen a source of polypeptides to identify one or more polypeptides containing a WW domain;

(iii) determining the amino acid sequence of the polypeptides identified in step (ii); and (iv) producing the one or more novel polypeptides containing a WW domain.

In another embodiment, said polypeptide is a polypeptide containing a WW domain produced by a method comprising:

(i) screening a peptide library with a WW domain to obtain a plurality of peptides that bind the WW domain;

(ii) determining a consensus sequence for the peptides obtained in step (i);

(iii) producing a peptide comprising the consensus sequence;

(iv) using the peptide comprising the consensus sequence to screen a source of polypeptides to identify one or more polypeptides containing a WW domain;

(v) determining the amino acid sequence of the polypeptides identified in step (iv); and (vi) producing the one or more polypeptides containing a WW domain.

In a preferred embodiment, the effect of the drug candidate upon multiple, different interacting polypeptide-recognition unit pairs is determined in which preferably at least some (e.g., at least 2, 3, 4, 5, 7, or 10) of said polypeptides have WW domains that vary in sequence yet are capable of displaying the same binding specificity, i.e., binding to the same recognition unit. In another specific embodiment, at least one of said polypeptides and/or recognition units contains a consensus WW domain and recognition unit, respectively (and thus are not known to be naturally expressed proteins). In another embodiment, the polypeptide is a novel polypeptide identified by the methods of the present invention. In a specific embodiment, an inhibitor of the polypeptide-recognition unit interaction is identified by detecting a decrease in the binding of polypeptide to recognition unit in the presence of such inhibitor.

A common problem in the development of new drugs is that of identifying a single, or a small number, of compounds that possess a desirable characteristic from among a background of a large number of compounds that lack that desired characteristic. This problem arises both in the testing of compounds that are natural products from plant, animal, or microbial sources and in the testing of man-made compounds. Typically, hundreds, or even thousands, of compounds are randomly screened by the use of in vitro assays such as those that monitor the compound's effect on some enzymatic activity, its ability to bind to a reference substance such as a receptor or other protein, or its ability to disrupt the binding between a receptor and its ligand.

The compounds which pass this original screening test are known as "lead" compounds. These lead compounds are then put through further testing, including, eventually, in vivo testing in animals and humans, from which the promise shown by the lead compounds in the original in vitro tests is either confirmed or refuted. See *Remington's Pharmaceutical Sciences*, 1990, A. R. Gennaro, ed., Chapter 8, pages 60–62, Mack Publishing Co., Easton, Pa.; Ecker and Crooke, 1995, Bio/Technology 13:351–360.

There is a continual need for new compounds to be tested in the in vitro assays that make up the first testing step described above. There is also a continual need for new assays by which the pharmacological activities of these compounds may be tested. It is an object of the present invention to provide such new assays to determine whether a candidate compound is capable of affecting the binding between a polypeptide containing a WW domain and a recognition unit that binds to that WW domain. In particular, it is an object of the present invention to provide polypeptides, particularly novel ones, containing WW domains and their corresponding recognition units for use in the above-described assays. The use of these polypeptides greatly expands the-number of assays that may be used to screen potential drug candidates for useful pharmacological activities (as well as to identify potential drug candidates that display adverse or undesirable pharmacological activities).

In one embodiment of the present invention, such polypeptides are identified by a method comprising: using a recognition unit that is capable of binding to a predetermined WW domain to screen a source of polypeptides, thus identifying novel polypeptides containing the WW domain or a similar WW domain.

In a particular embodiment of the above-described method, the novel polypeptide containing a WW domain is obtained by:

(i) screening a peptide library with the WW domain to obtain one or more peptides that bind the WW domain;

(ii) using one of the peptides from step (i), preferably in the form of a multivalent complex, to screen a source of polypeptides to identify one or more novel polypeptides containing WW domains;

(iii) determining the amino acid sequence of the polypeptides identified in step (ii); and (iv) producing the one or more novel polypeptides containing WW domains.

In another embodiment of the above-described method, the novel polypeptide containing a WW domain is obtained by:

(i) screening a peptide library with the WW domain to obtain peptides that bind the WW domain;

(ii) determining a consensus sequence for the peptides obtained in step (i);

(iii) producing a peptide comprising the consensus sequence;

(iv) using the peptide comprising the consensus sequence to screen a source of polypeptides to identify one or more novel polypeptides containing WW domains;

(v) determining the amino acid sequence of the novel polypeptides identified in step (iv); and (vi) producing the one or more novel polypeptides containing WW domains.

One of ordinary skill in the art will recognize that it will not always be necessary to utilize the entire novel polypeptide containing the WW domain in the assays described herein. Often, a portion of the polypeptide that contains the WW domain will be sufficient, e.g., a glutathione S-transferase (GST)-WW domain fusion protein. See FIG. 5 for a depiction of the portions of the exemplary novel polypeptides that contain WW domains.

A typical assay of the present invention consists of at least the following components: (1) a molecule (e.g., protein or polypeptide) comprising a WW domain; (2) a recognition unit that selectively binds to the WW domain; (3) a candidate compound, suspected of having the capacity to affect the binding between the protein containing the WW domain and the recognition unit. The assay components may further comprise (4) a means of detecting the binding of the protein comprising the WW domain and the recognition unit. Such means can be e.g., a detectable label affixed to the protein comprising the WW domain, the recognition unit, or the candidate compound. In a specific embodiment, the protein comprising the WW domain is a novel protein discovered by the methods of the present invention.

In another specific embodiment, the invention provides a method of identifying a compound that affects the binding of a molecule comprising a WW domain and a recognition unit that selectively binds to the WW domain comprising:

(a) contacting the molecule comprising the WW domain and the recognition unit under conditions conducive to binding in the presence of a candidate compound and measuring the amount of binding between the molecule and the recognition unit;

(b) comparing the amount of binding in step (a) with the amount of binding known or determined to occur between the molecule and the recognition unit in the absence of the candidate compound, where a difference in the amount of binding between step (a) and the amount of binding known or determined to occur between the molecule and the recognition unit in the absence of the candidate compound indicates that the candidate compound is a compound that affects the binding of the molecule comprising a WW domain and the recognition unit. In a specific embodiment, the compound is not a peptide.

In another specific embodiment, the invention provides a method of identifying a compound that affects the binding of a molecule comprising a WW domain and a recognition unit that selectively binds to the WW domain comprising:

(a) contacting the molecule comprising the WW domain and the recognition unit under conditions conducive to binding in the presence of a candidate compound and measuring the amount of binding between the molecule and the recognition unit in which the WW domain has an amino acid sequence selected from the group consisting of SEQ ID NOs:30–37 and 38;

(b) comparing the amount of binding in step (a) with the amount of binding known or determined to occur between the molecule and the recognition unit in the absence of the candidate compound, where a difference in the amount of binding between step (a) and the amount of binding known or determined to occur between the molecule and the recognition unit in the absence of the candidate compound indicates that the candidate compound is a compound that affects the binding of the molecule comprising a WW domain and the recognition unit.

In one embodiment, the assay comprises allowing the polypeptide containing a WW domain to contact a recognition unit that selectively binds to the WW domain in the presence and in the absence of the candidate compound under conditions such that binding of the recognition unit to the polypeptide containing a WW domain will occur unless that binding is disrupted or prevented by the candidate compound. By detecting the amount of binding of the recognition unit to the polypeptide containing a WW domain in the presence of the candidate compound and comparing that amount of binding to the amount of binding of the recognition unit to the polypeptide containing a WW domain in the absence of the candidate compound, it is possible to determine whether the candidate compound affects the binding and thus is a useful lead compound for the modulation of the activity of polypeptides containing the WW domain. The effect of the candidate compound may be to either increase or decrease the binding.

One version of an assay suitable for use in the present invention comprises binding the polypeptide containing a WW domain to a solid support such as the wells of a microtiter plate. The wells contain a suitable buffer and other substances to ensure that conditions in the wells permit the binding of the polypeptide containing a WW domain to its recognition unit. The recognition unit and a candidate compound are then added to the wells. The recognition unit is preferably labeled, e.g., it might be biotinylated or labeled with a radioactive moiety, or it might be linked to an enzyme, e.g., alkaline phosphatase. After a suitable period of incubation, the wells are washed to remove any unbound recognition unit and compound. If the candidate compound does not interfere with the binding of the polypeptide containing a WW domain to the labeled recognition unit, the labeled recognition unit will bind to the polypeptide containing a WW domain in the well. This binding can then be detected. If the candidate compound interferes with the binding of the polypeptide containing a WW domain and the labeled recognition unit, label will not be present in the wells, or will be present to a lesser degree than is the case when compared to control wells that contain the polypeptide containing a WW domain and the labeled recognition unit but to which no candidate compound is added. Of course, it is possible that the presence of the candidate compound will increase the binding between the polypeptide containing a WW domain and the labeled recognition unit. Alternatively, the recognition unit can be affixed to a solid substrate during the assay.

In a specific embodiment of the above-described method, the polypeptide containing a WW domain is a novel polypeptide containing a WW domain that has been identified by the methods of the present invention.

5.5. Use of Polypeptides Containing WW Domains to Discover Polypeptides Involved in Pharmacological Activities Using the methods of the present invention, it is possible to identify and isolate large numbers of polypeptides containing WW domains. Using these polypeptides, one can construct a matrix relating the polypeptides to an array of candidate drug compounds. For example, Table 1 shows such a matrix.

TABLE 1

|    | A | B | C | D | E | F | G | H | I | J |
|----|---|---|---|---|---|---|---|---|---|---|
| 1  |   |   |   |   |   |   |   |   |   |   |
| 2  |   | X |   | X |   |   |   | X |   |   |
| 3  |   |   |   |   |   |   |   |   |   |   |
| 4  |   |   |   |   |   |   |   |   |   |   |
| 5  |   |   |   |   |   | X |   |   |   |   |
| 6  |   |   |   |   |   |   |   |   |   |   |
| 7  |   |   | X |   |   |   |   | X |   |   |
| 8  |   |   |   |   |   |   |   |   |   |   |
| 9  | X |   |   |   |   |   |   |   |   |   |
| 10 |   |   |   |   |   |   |   |   |   |   |

In Table 1, the columns headed by letters at the top of the table represent different polypeptides containing WW domains (preferably novel polypeptides identified by the methods of the invention). The rows numbered along the left side of the table represent recognition units with various specificity to WW domains. For each candidate drug compound, a table such as Table 1 is generated from the results of binding assays. An X placed at the intersection of a particular numbered row and lettered column represents a positive assay for binding, i.e., the candidate drug compound affected the binding of the recognition unit of that particular row to the WW domain of that particular column.

Such data as that illustrated above is used to determine whether novel polypeptides or other molecules display or are at risk of displaying desirable or undesirable physiological or pharmacological activities. For example, in Table 1, the drug compound inhibits the binding of recognition unit 2 to the WW domains of polypeptides B, D, and H; the compound inhibits the binding of recognition unit 5 to the WW domain of polypeptide F; the compound inhibits the binding of recognition unit 7 to the WW domains of polypeptides C and H; and the compound inhibits the binding of recognition unit 9 to the WW domain of polypeptide A.

If interaction with polypeptide H leads to the desirable physiological or pharmacological activity, then this drug candidate might be a good lead. However, interaction with polypeptides A, B, C, D, and F would need to be evaluated for potential side effects.

As the maps are generated and pharmacological effects observed, the maps will allow strategic assessment of the specificity necessary to obtain the desired pharmacological effect. For example, if compounds 2 and 7 are able to affect some pharmacological activity, while compounds 5 and 9 do not affect that activity, then polypeptide H is likely to be involved in that pharmacological activity. For example, if compounds 2 and 7 were both able to inhibit mast cell degranulation, while compounds 5 and 9 did not, it is likely that polypeptide H is involved in mast cell degranulation.

Accordingly, the present invention provides a method of utilizing the polypeptides comprising WW domains of the present invention in an assay to determine the participation of those polypeptides in pharmacological activities.

In one embodiment, the method comprises:

(a) contacting a drug candidate with a molecule comprising a WW domain under conditions conducive to binding, and detecting or measuring any specific binding that occurs; and (b) repeating step (a) with a plurality of different molecules, each comprising a different WW domain but capable of binding to a single predetermined recognition unit under appropriate conditions.

Preferably, at least one of said molecules is a novel polypeptide identified by the methods of the present invention.

The present invention also provides a method of determining the potential pharmacological activities of a molecule comprising:

(a) contacting the molecule with a compound comprising a domain under conditions conducive to binding;

(b) detecting or measuring any specific binding that occurs; and (c) repeating steps (a) and (b) with a plurality of different compounds, each compound comprising a WW domain of different sequence but capable of displaying the same binding specificity.

5.6. Use of More Than One Recognition Unit Simultaneously

When screening a source of polypeptides with a recognition unit, it is possible to use more than one recognition unit at the same time. In a particular aspect, as many as five different recognition units may be used simultaneously to screen a source of polypeptides.

In particular, when the recognition units are biotinylated peptides and the source of polypeptides is a cDNA expression library, the steps of preconjugation of the biotinylated peptides to streptavidin-alkaline phosphatase as well as the steps involved in screening the cDNA expression library may be carried out in essentially the same manner as is done when a single biotinylated peptide is used as a recognition unit. See Section 6.1 for details. The key difference when using more than one biotinylated peptide at a time is that the peptides are combined either before or at the step where they are placed in contact with the polypeptides from which selection occurs.

In an embodiment employing a bacteriophage expression library to express the polypeptides, when the positive clones are worked up to the level of isolated plaques, the clonal bacteriophage from the isolated plaques may be tested against each of the biotinylated peptides individually, in order to determine to which of the several peptides that were used as recognition units in the primary screen the phage are actually binding.

5.7. Use of Recognition Units from known Amino Acid Sequences

In many cases it may not be necessary to screen a collection of substances, e.g., a peptide library, in order to obtain a recognition unit for a given WW domain. In the case of peptide recognition units, for example, it is sometimes possible to identify a recognition unit by inspection of known amino acid sequences. Stretches of these amino acid sequences that resemble known binding sequences for the WW domain can be synthesized and screened against a source of polypeptides in order to obtain a plurality of polypeptides comprising the given WW domain. In one embodiment of the present invention, peptides from the proteins WBP-1 and WBP-2 (known to bind to the WW domain-containing protein YAP (Chen and Sudol, 1995, Proc. Natl. Acad. Sci. USA 92:7819–7823)) were used as recognition units.

Prior to the disclosure of the present invention of methods of preparing recognition units having generic specificity, it would have been thought fruitless to pursue this approach. The expectation would have been that a recognition unit, chosen from published amino acid sequences as described above, would have been useful, at best, to identify a single protein containing a WW domain and would likely not have provided enough signal strength to differentiate positive binding from background.

5.8. Isolation and Expression of Nucleic Acids Encoding Polypeptides Comprising a WW Domain In particular aspects, the invention provides amino acid sequences of polypeptides comprising WW domains, preferably human polypeptides, and fragments and derivatives thereof which comprise an antigenic determinant (i.e., can be recognized by an antibody) or which are functionally active, as well as nucleic acid sequences encoding the foregoing. "Functionally active" material as used herein refers to that material displaying one or more functional activities, e.g., a biological activity, antigenicity (capable of binding to an antibody) immunogenicity, or comprising a WW domain that is capable of specific binding to a recognition unit. In specific embodiments, the invention provides fragments of polypeptides comprising a WW domain consisting of at least 40 amino acids, or of at least 75 amino acids. Nucleic acids encoding the foregoing are provided.

In other specific embodiments, the invention provides nucleotide sequences and subsequences encoding polypeptides comprising a WW domain, preferably human polypeptides, consisting of at least 25 nucleotides, at least 50 nucleotides, or at least 150 nucleotides. Nucleic acids encoding fragments of the polypeptides comprising a WW domain are provided, as well as nucleic acids complementary to and capable of hybridizing to such nucleic acids. In one embodiment, such a complementary sequence may be complementary to a cDNA sequence encoding a polypeptide comprising a WW domain of at least 25 nucleotides, or of at least 100 nucleotides. In a preferred aspect, the invention utilizes cDNA sequences encoding human polypeptides comprising a WW domain or a portion thereof.

Any eukaryotic cell can potentially serve as the nucleic acid source for the molecular cloning of polypeptides comprising a WW domain. The DNA may be obtained by standard procedures known in the art (e.g., a DNA "library") by cDNA cloning, or by the cloning of genomic DNA, or fragments thereof, purified from the desired cell (see, for example Sambrook et al., 1989, Molecular Cloning, A Laboratory Manual, Cold Spring Harbor Laboratory, 2d. Ed., Cold Spring Harbor, N.Y.; Glover, D. M. (ed.), 1985, DNA Cloning: A Practical Approach, MRL Press, Ltd., Oxford, U. K. Vol. I, II.) Clones derived from genomic DNA may contain regulatory and intron DNA regions in addition to coding regions; clones derived from cDNA will contain only exon sequences. Whatever the source, the gene encoding a polypeptide comprising a WW domain should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once a gene encoding a particular polypeptide comprising a WW domain has been isolated from a first species, it is a routine matter to isolate the corresponding gene from another species. Identification of the specific DNA fragment from another species containing the desired gene may be accomplished in a number of ways. For example, if an amount of a portion of a gene or its specific RNA from the first species, or a fragment thereof e.g., the WW domain, is available and can be purified and labeled, the generated DNA fragments from another species may be screened by nucleic acid hybridization to the labeled probe (Benton, W. and Davis, R., 1977, Science 196, 180; Grunstein, M. And Hogness, D., 1975, Proc. Natl. Acad. Sci. U.S.A. 72, 3961). Those DNA fragments with substantial homology to the probe will hybridize. In a preferred embodiment, PCR using primers that hybridize to a known sequence of a gene of one species can be used to amplify the homolog of such gene in a different species. The amplified fragment can then be isolated and inserted into an expression or cloning vector. It is also possible to identify the appropriate fragment by restriction enzyme digestion(s) and comparison of fragment sizes with those expected according to a known restriction map if such is available. Further selection can be carried out on the basis of the properties of the gene. Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, in vitro aggregation activity ("adhesiveness") or antigenic properties as known for the particular polypeptide comprising a WW domain from the first species. If an antibody to that particular polypeptide is available, the corresponding polypeptide from another species may be identified by binding of labeled antibody to the putative polypeptide synthesizing clones in an ELISA (enzyme-linked immunosorbent assay)-type procedure.

Genes encoding polypeptides comprising a WW domain can also be identified by mRNA selection by nucleic acid hybridization followed by in vitro translation. In this procedure, fragments are used to isolate complementary mRNAs by hybridization. Such DNA fragments may represent available, purified DNA of genes encoding polypeptides comprising a WW domain of a first species. Immunoprecipitation analysis or functional assays (e.g., ability to bind to a recognition unit) of the in vitro translation products of the isolated mRNAs identifies the mRNA and, therefore, the complementary DNA fragments that contain the desired sequences. In addition, specific mRNAs may be selected by adsorption of polysomes isolated from cells to immobilized antibodies specifically directed against polypeptides comprising a WW domain. A radiolabelled cDNA of a gene encoding a polypeptide comprising a WW domain can be synthesized using the selected mRNA (from the adsorbed polysomes) as a template. The radiolabelled mRNA or cDNA may then be used as a probe to identify the DNA fragments that represent the gene encoding the polypeptide comprising a WW domain of another species from among other genomic DNA fragments. In a specific embodiment, human homologs of mouse genes are obtained by methods described above. In various embodiments, the human homolog is hybridizable to the mouse homolog under conditions of low, moderate, or high stringency. By way of example and not limitation, procedures using such conditions of low stringency are as follows (see also Shilo and Weinberg, 1981, Proc. Natl. Acad. Sci. USA 78:6789–6792): Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5–20×10$^6$ cpm $^{32}$P-labeled probe is used. Filters are incubated in hybridization mixture for 18–20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65–68° C. and reexposed to film. Other conditions of low stringency which may be used are well known in the art (e.g., as employed for cross-species hybridizations).

By way of example and not limitation, procedures using conditions of high stringency are as follows:

Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA and 5–20×10$^6$ cpm of $^{32}$P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency which may be used are well known in the art.

The identified and isolated gene encoding a polypeptide comprising a WW domain can then be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as PBR322 or pUC plasmid derivatives. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and gene may be modified by homopolymeric tailing. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment for the desired gene, for example, by size fractionization, can be done before insertion into the cloning vector.

In specific embodiments, transformation of host cells with recombinant DNA molecules that incorporate the isolated gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

The nucleic acid coding for a polypeptide comprising a WW domain of the invention can be inserted into an appropriate expression vector, i.e., a vector which contains the necessary elements for the transcription and translation of the inserted protein-coding sequence. The necessary transcriptional and translational signals can also be supplied by the native gene encoding the polypeptide and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

Any of the methods previously described for the insertion of DNA fragments into a vector may be used to construct expression vectors containing a chimeric gene consisting of appropriate transcriptional/translational control signals operably linked to the protein coding sequences. These methods may include in vitro recombinant DNA and synthetic techniques and in vivo recombinants (genetic recombination). Expression of nucleic acid sequence encoding a protein or peptide fragment may be regulated by a second nucleic acid sequence so that the protein or peptide is expressed in a host transformed with the recombinant DNA molecule. For example, expression of a protein may be controlled by any promoter/enhancer element known in the art. Promoters which may be used to control gene expression include, but are not limited to, the SV40 early promoter region (Benoist and Chambon, 1981, Nature 290, 304–310), the promoter contained in the 3' long terminal repeat of Rous sarcoma virus (Yamamoto, et al., 1980, Cell 22, 787–797), the herpes thymidine kinase promoter (Wagner et al., 1981, Proc. Natl. Acad. Sci. U.S.A. 78, 1441–1445), the regulatory sequences of the metallothionein gene (Brinster et al., 1982, Nature 296, 39–42); prokaryotic expression vectors such as the β-lactamase promoter (Villa-Kamaroff, et al., 1978, Proc. Natl. Acad. Sci. U.S.A. 75, 3727–3731), or the tac promoter (DeBoer, et al., 1983, Proc. Natl. Acad. Sci. U.S.A. 80, 21–25); see also "Useful proteins from recombinant bacteria" in Scientific American, 1980, 242, 74–94; plant expression vectors comprising the nopaline synthetase promoter region (Herrera-Estrella et al., Nature 303, 209–213) or the cauliflower mosaic virus 35S RNA promoter (Gardner, et al., 1981, Nucl. Acids Res. 9, 2871), and the promoter of the photosynthetic enzyme ribulose biphosphate carboxylase (Herrera-Estrella et al., 1984, Nature 310, 115–120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38, 639–646; Ornitz et al., 1986, Cold Spring Harbor Symp. Quant. Biol. 50, 399–409; MacDonald, 1987, Hepatology 7, 425–515); insulin gene control region which is active in pancreatic beta cells (Hanahan, 1985, Nature 315, 115–122), immunoglobulin gene control region which is active in lymphoid cells (Grosschedl et al., 1984, Cell 38, 647–658; Adames et al., 1985, Nature 318, 533–538; Alexander et al., 1987, Mol. Cell. Biol. 7, 1436–1444), mouse mammary tumor virus control region which is active in testicular, breast, lymphoid and mast cells (Leder et al., 1986, Cell 45, 485–495), albumin gene control region which is active in liver (Pinkert et al., 1987, Genes and Devel. 1, 268–276), alpha-fetoprotein gene control region which is active in liver (Krumlauf et al., 1985, Mol. Cell. Biol. 5, 1639–1648; Hammer et al., 1987, Science 235, 53–58; alpha 1-antitrypsin gene control region which is active in the liver (Kelsey et al., 1987, Genes and Devel. 1, 161–171), beta-globin gene control region which is active in myeloid cells (Mogram et al., 1985, Nature 315, 338–340; Kollias et al., 1986, Cell 46, 89–94; myelin basic protein gene control region which is active in oligodendrocyte cells in the brain (Readhead et al., 1987, Cell 48, 703–712); myosin light chain-2 gene control region which is active in skeletal muscle (Sani, 1985, Nature 314, 283–286), and gonadotropic releasing hormone gene control region which is active in the hypothalamus (Mason et al., 1986, Science 234, 1372–1378).

Expression vectors containing inserts of genes encoding polypeptides comprising a WW domain can be identified by three general approaches: (a) nucleic acid hybridization, (b) presence or absence of "marker" gene functions, and (c) expression of inserted sequences. In the first approach, the presence of a foreign gene inserted in an expression vector can be detected by nucleic acid hybridization using probes comprising sequences that are homologous to the inserted gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if the gene encoding a polypeptide comprising a WW domain is inserted within the marker gene sequence of the vector, recombinants containing the gene can be identified by the absence of the marker gene function. In the third approach, recombinant expression vectors can be identified by assaying the foreign gene product expressed by the recombinant. Such assays can be based, for example, on the physical or functional properties of the gene product in vitro assay systems, e.g., ability to bind to recognition units.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the protein may be controlled. Furthermore, different host cells have characteristic and specific mechanisms for the translational and post-translational processing and modification (e.g., glycosylation, cleavage) of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of a heterologous protein. Furthermore, different vector/host expression systems may effect processing reactions such as proteolytic cleavages to different extents.

In other specific embodiments, polypeptides comprising a WW domain, or fragments, analogs, or derivatives thereof may be expressed as a fusion, or chimeric protein product (comprising the polypeptide, fragment, analog, or derivative joined via a peptide bond to a heterologous protein sequence (of a different protein)). Such a chimeric product can be made by ligating the appropriate nucleic acid sequences encoding the desired amino acid sequences to each other by methods known in the art, in the proper reading frame, and expressing the chimeric product by methods commonly known in the art. Alternatively, such a chimeric product may be made by protein synthetic techniques, e.g., by use of a peptide synthesizer.

5.8.1. Identification and Purification of the Expressed Gene Products

Once a recombinant which expresses the gene sequence encoding a polypeptide comprising a WW domain is identified, the gene product may be analyzed. This can be achieved by assays based on the physical or functional properties of the product, including radioactive labelling of the product followed by analysis by gel electrophoresis.

Once the polypeptide comprising a WW domain is identified, it may be isolated and purified by standard methods including chromatography (e.g., ion exchange affinity, and sizing column chromatography), centrifugation, differential solubility, or by any other standard technique for the purification of proteins. The functional properties may be evaluated using any suitable assay, including, but not limited to, binding to a recognition unit.

5.9. Derivatives and Analogs of Polypeptides Comprising a WW Domain

The invention further provides derivatives (including but not limited to fragments) and analogs of polypeptides comprising a WW domain. In a specific embodiment, the derivative or analog is functionally active, i.e., capable of exhibiting one or more functional activities associated with a full-length, wild-type polypeptide, e.g., binding to a recognition unit. As one example, such derivatives or analogs may have the antigenicity of the full-length polypeptide.

In particular, derivatives can be made by altering gene sequences encoding polypeptides comprising a WW domain by substitutions, additions, or deletions that provide for functionally equivalent molecules. Due to the degeneracy of nucleotide coding sequences, other DNA sequences which encode substantially the same amino acid sequence as a gene encoding a polypeptide comprising a WW domain may be used in the practice of the present invention. These include but are not limited to nucleotide sequences comprising all or portions of such genes which are altered by the substitution of different codons that encode a functionally equivalent amino acid residue within the sequence, thus producing a silent change. Likewise, the derivatives of the invention include, but are not limited to, those containing, as a primary amino acid sequence, all or part of the amino acid sequence of a polypeptide comprising a WW domain including altered sequences in which functionally equivalent amino acid residues are substituted for residues within the sequence, resulting in a silent change. For example, one or more amino acid residues within the sequence can be substituted by another-amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Derivatives or analogs of genes encoding polypeptides comprising a WW domain include but are not limited to those polypeptides which are substantially homologous to the genes or fragments thereof, or whose encoding nucleic acid is capable of hybridizing to-a nucleic acid sequence of the genes.

The derivatives and analogs of the invention can be produced by various methods known in the art. The manipulations which result in their production can occur at the gene or protein level. For example, the cloned gene sequence can be modified by any of numerous strategies known in the art (Maniatis, T., 1989, Molecular Cloning, A Laboratory Manual, 2d ed., Cold Spring Harbor Laboratory, Cold Spring Harbor, N.Y.). The sequence can be cleaved at appropriate sites with restriction endonuclease(s), followed by further enzymatic modification if desired, isolated, and ligated in vitro. PCR primers can be constructed so as to introduce desired sequence changes during PCR amplification of a nucleic acid encoding the desired polypeptide. In the production of the gene encoding a derivative or analog, care should be taken to ensure that the modified gene remains within the same translational reading frame, uninterrupted by translational stop signals, in the gene region where the desired activity is encoded.

Additionally, the sequence of the genes encoding polypeptides comprising a WW domain can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C., et al., 1978, J. Biol. Chem 253:6551), use of TAB® linkers (Pharmacia, Piscataway, N.J.), etc.

Manipulations of the sequence may also be made at the protein level. Included within the scope of the invention are protein fragments or other derivatives or analogs which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, NaBH$_4$; acetylation, formylation, oxidation, reduction; metabolic synthesis in the presence of tunicamycin; etc.

In addition, analogs and derivatives can be chemically synthesized. For example, a peptide corresponding to a portion of a polypeptide comprising a WW domain can be synthesized by use of a peptide synthesizer. Furthermore, if desired, nonclassical amino acids or chemical amino acid analogs can be introduced as a substitution or addition into the sequence. Non-classical amino acids include but are not limited to the D-isomers of the common amino acids, α-amino isobutyric acid, 4-aminobutyric acid, hydroxyproline, sarcosine, citrulline, cysteic acid, t-butylglycine, t-butylalanine, phenylglycine, cyclohexylalanine, β-alanine, designer amino acids such as β-methyl amino acids, Cα-methyl amino acids, and Nα-methyl amino acids.

5.10. Antibodies to Polypeptides Comprising a WW Domain

According to one embodiment, the invention provides antibodies and fragments containing the binding domain thereof, directed against polypeptides comprising a WW domain. Accordingly, polypeptides comprising a WW domain, fragments, analogs, or derivatives thereof, in particular, may be used as immunogens to generate antibodies against such polypeptides, fragments, analogs, or derivatives. Such antibodies can be polyclonal, monoclonal, chimeric, single chain, Fab fragments, or from an Fab expression library. In a specific embodiment, antibodies specific to the WW domain of a polypeptide comprising a WW domain may be prepared.

Various procedures known in the art may be used for the production of polyclonal antibodies. In a particular embodiment, rabbit polyclonal antibodies to an epitope of a polypeptide comprising a WW domain, or a subsequence thereof, can be obtained. For the production of antibody, various host animals can be immunized by injection with the native polypeptide comprising a WW domain, or a synthetic version, or fragment thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*.

For preparation of monoclonal antibodies, any technique which provides for the production of antibody molecules by continuous cell lines in culture may be used. For example, the hybridoma technique originally developed by Kohler and Milstein (1975, Nature 256, 495–497), as well as the trioma technique, the human B-cell hybridoma technique (Kozbor et al., 1983, Immunology Today 4, 72), and the EBV-hybridoma technique to produce human monoclonal antibodies (Cole et al., 1985, in Monoclonal Antibodies and Cancer Therapy, Alan R. Liss, Inc., pp. 77–96) may be used.

Antibody fragments which contain the idiotype (binding domain) of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g. ELISA (enzyme-linked immunosorbent assay).

6. EXAMPLES 6.1. Identification of Genes from cDNA Expression Libraries Using Recognition Units Derived from WBP-1, WBP-2, ENaCβ, and ENaCγ

A study was initiated to determine whether peptide recognition units could recognize WW domains that are the same as or similar to their target WW domain but that are contained in proteins other than the protein containing their target WW domain. Such "functional" screens, using recognition units of relatively small size, were not previously known and are difficult to develop because of the low degree of sequence homology among WW domain-containing proteins. Thus, for example, an oligonucleotide probe could not be designed with any degree of confidence based on the low degree of homology of primary sequences of WW domains.

A 16 day mouse embryo cDNA expression library from Novagen (Madison, Wis.) was screened using as a recognition unit synthetic peptides based upon the sequences of the YAP WW domain binding proteins WBP-1 and WBP-2 (Chen and Sudol, 1995, Proc. Natl. Acad. Sci. USA 92:7819–7823). The YAP peptides were chosen as a result of a search of the Swiss-Protein database for sequences that resembled the PPPPY (SEQ ID NO:3) consensus motif for WW binding peptides. The 16 day mouse embryo cDNA expression library was screened with these recognition units and clones were isolated that expressed mouse Nedd-4 and mouse YAP.

The peptide recognition units that were used were:

```
TP=biotin-HPGTPPPPYTVGP        (SEQ ID NO:6)

YP=biotin-PGYPYPPPPPEFY        (SEQ ID NO:7)

QP=biotin-YVQPPPPPYPGPM        (SEQ ID NO:8)
```

Screening of the library, including biotinylation of the peptide recognition units and their complexation with streptavidin-alkaline phosphatase, was as follows.

The 16 day mouse embryo cDNA expression library was diluted 1:1000 in SM solution (100 mM NaCl, 8 mM MgSOv$_4$, 50 mM Tris HCl pH 7.5, 0.01% gelatin). To a sterile test tube, 2 μl of diluted mouse embryo library, 100 μl of 10 mM CaCl$_2$, 100 μl of 10 mM MgCl$_2$ and 100 μl of BL21(DE3)pLysE bacterial cells (grown overnight) were added and incubated for 30 minutes at 37° C. The contents of the tube were mixed with 3 ml of 0.6% top agarose, containing 25 mg/ml chloramphenicol, and poured onto a 2xYT plate (90 mm diameter). For a large primary screen, 10–20 plates were prepared with 3×10$^4$ pfu per plate. After 6 hours incubation at 37° C., a nitrocellulose filter soaked in 10 mM isopropyl-β-D-thiogalactopyranoside (IPTG) was overlaid on each plate and incubated 3–6 hours at 37° C. Before the filters were removed from the plates, they were marked asymmetrically with India ink in a 18 gauge syringe needle. The plates were stored at 4° C. until ready for the secondary screen. The filters were washed with PBS (137 mM NaCl, 2.7 mM KCl, 4.3 mM Na$_2$HPO$_4$, 1.4 mM KH$_2$PO$_4$)-0.05% Triton X-100 three times at room temperature, 15 minutes each wash, and then placed in a plastic bag containing non-specific blocking solution (PBS-2% BSA) for one hour. In the meantime, 1 ml of 1 mM biotinylated peptide in PBS-0.1% Tween 20 was added to 20 ml of 1 mg/ml streptavidin-alkaline phosphatase (SA-AP) in PBS-0.1% Tween 20 and incubated at 4° C. for 30 minutes. As an alternative method of forming multivalent complexes, 50 pmol biotinylated peptide could have been incubated with 2 μg SA-AP (for a biotin:biotin-binding site ratio of 1:1). Excess biotin-binding sites would then be blocked by addition of 500 pmol biotin. As a further alternative, 31.2 μl of 1 mg/ml SA-AP could have been incubated with 15 μl of 0.1 mM biotinylated peptide for 30 min at 4° C. Ten μl of 0.1 mM biotin would then be added, and the solution incubated for an additional 15 min.

The preconjugated peptide recognition unit was introduced into the plastic bag containing the nitrocellulose filters and incubated overnight at room temperature. After three washes with PBS-0.1% Tween 20, the filters were incubated in 50 ml of 50 mg/ml 5-bromo-4-chloro-3-indolyl phosphate (BCIP), 100 ml of 50 mg/ml of dimethylformamide (DMF), and 15 ml of alkaline phosphatase buffer (0.1 M Tris-HCl, pH 9.4, 0.1 M NaCl, 50 mM MgCl$_2$). Strong positive signals were evident in 5–10 minutes.

Positive plaques were cored with a Pasteur pipet from the petri plates that had been spread with the full cDNA library and left in 500 μl of SM for 1 hour at room temperature or overnight at 4° C. with a drop of chloroform present. Five microliters of a 1:100 dilution of the eluted phage were plated out for rescreening, with the intention of reducing the number of plaque forming units (pfu) by a factor of 10 (i.e. $3 \times 10^4$ in the primary screen, $3 \times 10^3$ in the secondary, etc.), until all the plaques were positive when screened.

After three rounds of screening, isolated positive plaques were obtained. The pEXlox plasmid was recovered from the recombinant lambda genomes of the isolated phage by cre-mediated excision in BM25.8 *E. coli* cells. For each lambda clone, 5 μl of diluted phage (1:100 in SM) were added to a sterile test tube containing 100 μl SM and 100 μl of an overnight culture of BM25.8 cells. After 30 minutes incubation at 37° C., this mixture was spread on an 2xYT petri plate containing 100 mg/ml ampicillin and incubated overnight at 37° C. A single colony was picked from the plate, inoculated into 3 ml of 2xYT broth containing 100 mg/ml ampicillin and incubated overnight at 37° C. Plasmid DNA was isolated using a miniprep kit (Qiagen, Chatsworth, Calif.) and transformed into chemically competent DH5αF' cells. At least two colonies were selected from each transformation, and grown in 3 ml of 2xYT broth containing 100 mg/ml ampicillin overnight. DNA was prepared as described above. To evaluate the size of the cDNA inserts in each plasmid, approximately 1/20 of each purified DNA sample was digested with EcoRI and HindIII to release the insert and resolved by agarose gel electrophoresis. DNA was sequenced by the dideoxy method with the T7 gene 10 oligonucleotide primer.

Five clones were identified and isolated when the cDNA library was screened with the peptide QP. The cDNA inserts of these clones were sequenced in order to identify them. A schematic diagram of these clones in shown in FIG. 8. As can be seen in FIG. 8, the screen with the QP peptide identified 5 clones containing portions of the mouse Nedd-4 gene.

The cDNA library was also screened with a 1:1:1 mixture of the peptides TP, YP, and QP (SEQ ID NOs:6–8). FIG. 9 shows that this screen identified 2 clones containing portions of the mouse YAP gene.

The method described above was also carried out using as recognition units the following synthetic peptides based upon sequences of the YAP WW domain-binding proteins WBP-1 and WBP-2:

```
WBP-1    biotin-SGSGPGTPPPPYTVGPGY    (SEQ ID NO:9)

WBP-2A   biotin-SGSGYVQPPPPYPGPM     (SEQ ID NO:10)

WBP-2B   biotin-SGSGPGTPYPPPPEFY     (SEQ ID NO:11)
```

The three peptides were biotinylated and complexed with streptavidin-alkaline phosphatase as described above except for the WBP-1 peptide which was complexed with streptavidin-horseradish peroxidase. Detection of the bound peptides was as described above except for WBP-1, which was detected with the IBI enzygraphic™ Web (Kodak, New Haven, Conn.) as described by the manufacturer. See Section 6.5. Alternatively, the TSA tyramide signal amplification system (DuPont, Wilmington, Del.) could be used.

Figure 10:
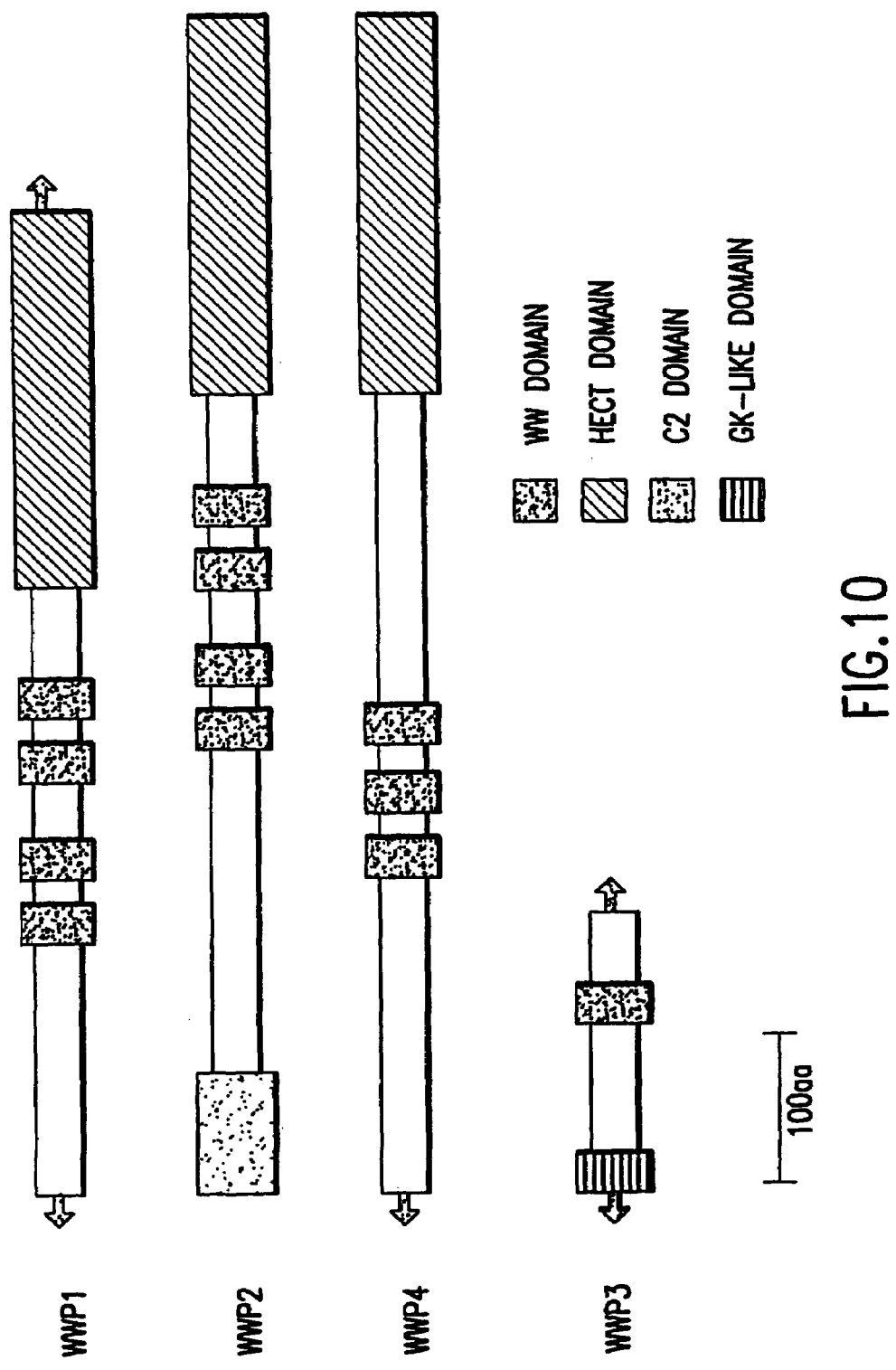

These three peptides were used as a mix to screen human bone marrow and brain cDNA libraries (Clontech, Palo Alto, Calif.). Thirteen cDNA clones were identified and isolated. These clones represented three novel human genes, called WWP1, WWP2, and WWP3. WWP1 and WWP2 were isolated from both the brain and the bone marrow library; WWP3 was isolated from the brain library. Altogether, these three novel genes possessed nine novel WW domains. FIG. 10 shows a schematic diagram of these three novel WW domain-containing genes. The nucleotide and corresponding amino acid sequences of the inserts of the cDNA clones containing these novel genes were obtained. DNA was sequenced on both strands using PRISM DyeDeoxy Terminator Cycle chemistry (Perkin/Elmer, Foster City, Calif.). These DNA sequences, as well as the corresponding amino acid sequences, are shown in FIGS. 16–21.

The method described above was also applied to screen a cDNA expression library generated from the LNCap Prostate Cancer Cell line using ENaCβ and ENaCγ as recognition units. These recognition units are synthetic peptides that are based upon sequences of WW binding domains of the α and γ subunits of Epithelial Na$^+$ Channel Protein.

```
ENaCβ  biotin - PGTPPPNYDSLRL    (SEQ ID NO:59)

ENaCγ  biotin - PGTPPPKYNTLRL    (SEQ ID NO:60)
```

The two peptides were biotinylated and complexed with streptavidin-alkaline phosphatase as described above. Detection of the band peptides was also as described above.

These two peptides were used as a mix to screen the human prostate library. This screen identified WWP1, described above, and a novel gene called WWP4, possessing three novel WW domains. FIG. 10 shows a schematic diagram of this novel WW domain containing gene. The nucleotide and corresponding amino acid sequences of cDNA clones containing this novel gene were obtained. DNA was sequenced on both strands using PRISM DyeDeoxy Terminator Cycle chemistry (Perkin/Elmer, foster City, Calif.). These DNA sequences, as well as the corresponding amino acid sequences, are shown in FIGS. 22 and 23, respectively.

From the cross affinity mapping data shown in FIGS. 15A and 15B, it can be seen that two or more WW domains in each of the proteins WWP1, WWP2, and WWP4 specifically bind to recognition units WBP-1, WBP-2A and WBP-2C but that none of the WW domains of these proteins specifically bind to WBP-2B. WWP3 specifically binds to recognition unit WBP-2A but not to WBP-1 or WBP-2B.

Based upon their possession of a HECT domain (See FIG. 10 and FIG. 14), three of the new genes (WWP1, WWP2, and WWP4) appear to be members of a family of proteins, including RSP5 and Nedd-4, that have ubiquitin-ligase activity. Two of the three genes, WWP1 and WWP2, possess four WW domains each. The third gene, WWP4, possesses three WW domains. The remaining novel gene, WWP3, possesses a single WW domain and the N-terminal portion of a second, truncated WW domain. WWP3 also possesses a guanylate kinase-like region.

6.1.1. Nucleotide and Corresponding Amino Acid Sequences of Novel Genes Identified from cDNA Expression Libraries The nucleotide sequences of WWP1, WWP2, WWP3, and WWP4 are shown in FIGS. 16, 18A and 18B, and 20 and 22, respectively. The amino acid sequences of WWP1, WWP2, WWP3, and WWP4 are shown in FIGS. 17, 19, 21, and 23, respectively.

FIG. 5 shows a comparison of the amino acid sequences of the four WW domains from WWP1, the four WW domains from WWP2, the three WW domains from WWP4 and the WW domain from WWP3, with the amino acid sequences of WW domains from a variety of known proteins. Alignment of the twelve novel WW domain sequences with several previously identified WW domains reveals two significant blocks of homology flanking the core of the domain. These blocks include an N-terminal tryptophan and a C-terminal proline residue that are absolutely conserved in all WW domains known to date. Also depicted is a consensus sequence based upon the various WW domain sequences shown. A single amino acid gap has been introduced in the amino acid sequence of the third WW domain of WWP2 (WWP2-3 in FIG. 5) between positions 12 and 13 in order to maximize homology with the other WW domains.

In addition to the WW domains, primary sequence analysis of the novel clones revealed several other interesting structural features. Clones WWP2 and WWP4, contain a complete C-terminal HECT domain, and WWP1 contains a partial HECT domain at the carboxy terminus (FIG. 10, FIG. 14, and FIG. 23). This domain has been shown to have in vitro E3 ubiquitin-protein ligase activity in the yeast Rsp5 and human papilloma virus E6-AP proteins and encodes a conserved cysteine residue within the last 40 amino acids that is the likely site for ubiquitin thioester formation (Huibregste et al., 1995, Proc. Natl. Acad. Sci. USA 92: 2563–2567). This is noteworthy since structurally and functionally related E3 ubiquitin-protein ligases are thought to serve a major role in defining the substrate specificity of the ubiquitin degradation system (Ciechanover, 1994, Cell 79:13–21). In fact, Rsp5 was recently shown to be involved in the induced degradation of several nitrogen permeases in yeast (Hein et al, 1995, Mol. Microbiol. 18:77–87). WWP2 also encodes an N-terminal C2-like domain characteristic of a large family of proteins including protein kinase C (Kaibuchi et al., 1989, J. Biol. Chem. 264:13489–13496) and synaptotagmins (Sutton et al., 1995, Cell 80:929–938). The C2 domain has been shown to bind membrane phospholipids in a calcium-dependent manner, and is thought to function in the intracellular compartmentalization of proteins (Davletov and Sudhof, 1993, J.Biol. Chem. 268:26386–26390). Although the various domains present within WWP1, WWP2, and WWP4 are highly homologous to those found in Nedd-4 and Rsp5, there is no significant homology among these proteins in regions flanking these domains, indicating they may have related but specific functions. Also of interest is the presence in clone WWP3 of an N-terminal guanylate kinase-like domain similar to those involved in GMP binding in several membrane-associated proteins including human erythrocyte membrane protein p55 (Ruff et al., 1991, Proc. Natl. Acad. Sci. USA 88:6595–6599) and rat presynatic density protein (PSD-95)(Cho et al., 1992, Neuron 9:929–942).

6.2. Identification of Recognition Units that Bind the WW Domain of Dystrophin and Screening of cDNA Library The WW domain of dystrophin was chosen as a target WW domain. Using this WW domain as a probe, a random peptide phage display library was screened in order to identify and isolate peptides that functioned as recognition units of the dystrophin WW domain. These recognition unit peptides were synthesized, biotinylated and used to screen a λEXlox mouse 16 day embryo cDNA expression library (obtained from Novagen, Madison, Wis.).

The WW domain is located at the end of the central rod region of dystrophin, close to the cysteine-rich domain. A glutathione S-transferase (GST)-fusion protein containing this WW domain was prepared as follows. Two oligonucleotide primers were designed to flank the dystrophin WW domain:

```
                                          (SEQ ID NO:40)
    5'-CTGTGCGGATCCAAGACCTGAACACCAGATGGA-3'  and (SEQ ID NO:41)
    5'-CTGTGCGAATTCCAAAGTCTCGAACAT-3'.
```

Bam HI and Eco RI sites are underlined. The dystrophin WW domain was amplified through 24 cycles of the polymerase chain reaction (PCR). The 220 bp amplified fragment was purified with GeneClean (Bio 101, San Diego, Calif.) after agarose gel electrophoresis, digested with Bam HI and Eco RI, phenol-chloroform extracted, ethanol precipitated, and ligated into Bam HI and Eco RI digested pGEX-2T vector DNA (Pharmacia, Piscataway, N.J.). *E. coli* (DH5αF') cells were transformed with the ligated DNA and ampicillin resistant transformants were selected. Recombinants were verified by DNA sequencing.

Colonies of *E. coli* carrying the GST-dystrophin WW domain fusion protein were used to inoculate 50 ml of 2xYT medium containing 2% glucose and 100 mg/ml ampicillin. After growth overnight at 37° C., a 500 ml culture flask was inoculated with the cells; the cells were grown with vigorous aeration until the optical absorbance (590 nm) reached 0.6 to 0.8 optical units. To induce expression of the fusion protein, isopropyl-β-D-thiogalactopyranoside (IPTG) was added to the culture to a final concentration of 0.1 mM. After 4–6 hours, the cells were transferred to centrifuge bottles, centrifuged at 7,700xg for 10 minutes at 4° C., and the pellet was resuspended in 25 ml of ice-cold PBS (137 mM NaCl, 2.7 mM KCl, 4.3 mM $Na_2HPO_4$, 1.4 mM $KH_2PO_4$). The cell suspension was then disrupted with sonication. Sonication was accomplished with short bursts, as over sonication leads to poorer yields. Triton X-100 detergent was added to a final concentration of 1%, the lysate was mixed gently for 30 minutes at 4° C. and then centrifuged at 12,000×g for 10 minutes. Two ml of glutathione Sepharose 4B (Pharmacia, Piscataway, N.J.), 50% slurry with PBS, was added to each 100 ml of the supernatant of the sonicated cell lysate. The mixture was incubated with gentle agitation at room temperature for 30 minutes. The mixture was then centrifuged at 500×g for 5 minutes to sediment the matrix and the supernatant was discarded. The pellet was washed with 10 volumes of PBS three times, centrifuged, and the bound GST-dystrophin WW domain fusion protein eluted with 1 ml of glutathione elution buffer (3.07 mg/ml glutathione, 100 mM NaCl, 50 mM Tris, pH 8.0) per ml volume of Sepharose. The fusion protein was partitioned from the beads by centrifugation at 500×g for 5 minutes. The amount of fusion protein recovered was estimated by the Bradford protein assay, and its purity was evaluated by 10% SDS-polyacrylamide gel electrophoresis and Coomassie Blue staining.

Figure 11:
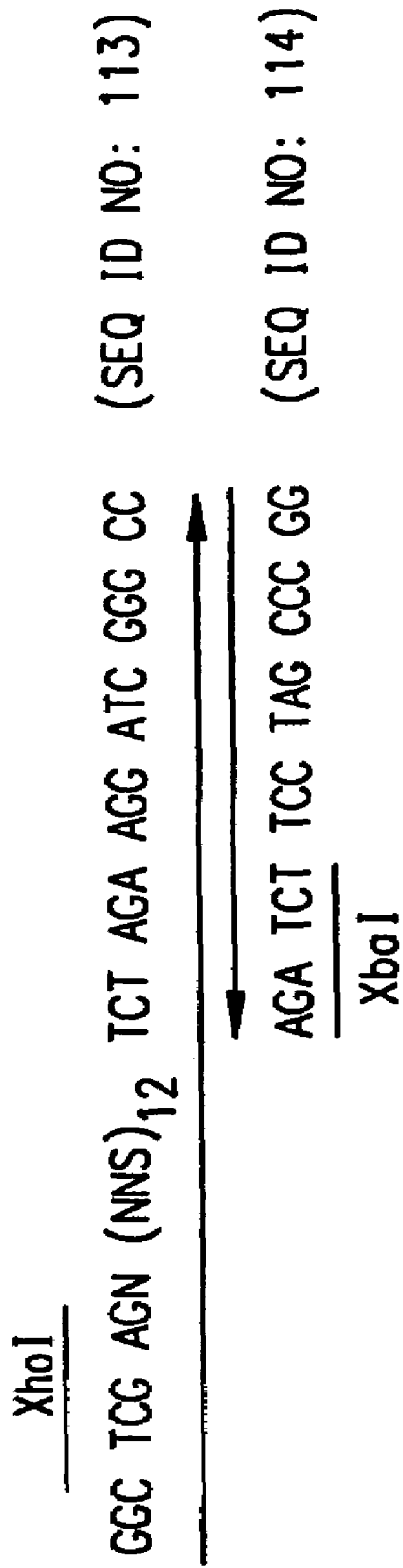
FIG. 11 shows the sequences of the oligonucleotides used to construct the CW1 random peptide library. See Section 6.2 for details.

The purified GST-dystrophin WW domain fusion protein was used to screen a random peptide phage display library. The library, termed CW1, was prepared as follows. Two oligonucleotides (see FIG. 11) were synthesized, annealed, and converted into double-stranded DNA with Sequenase (US Biochemical Corp., Cleveland, Ohio) and deoxynucleotides according to published protocols (Kay et al., 1993, Gene 128:59–65). The oligonucleotides encoded random peptides with the codons NNS; N represents an equimolar mixture of A, C, G, and T; S corresponds to an equimolar mixture of C and G. The NNS coding scheme utilizes 32 codons to encode 20 amino acids; the number of codons for the amino acids is either one (C, D, E, F, H, I, K, L, M, N, Q, W, Y), two (A, G, P, V, T), or three (L, R, S). The assembled oligonucleotides were cleaved with the restriction enzymes XhoI and XbaI and ligated into a bacteriophage M13 vector, mBAX. The ligated DNA was introduced into E. coli JS5 by electroporation to generate a library of approximately $10^9$ recombinants. The random peptides were displayed at the N terminus of mature pIII, in 3–5 copies per phage particle. Each phage particle of the CW1 library displays the sequence S(S/R)X$_{12}$SRPT (SEQ ID NO:42) at the N-terminus of mature pIII, where X represents any of the 20 amino acids.

Figure 12:
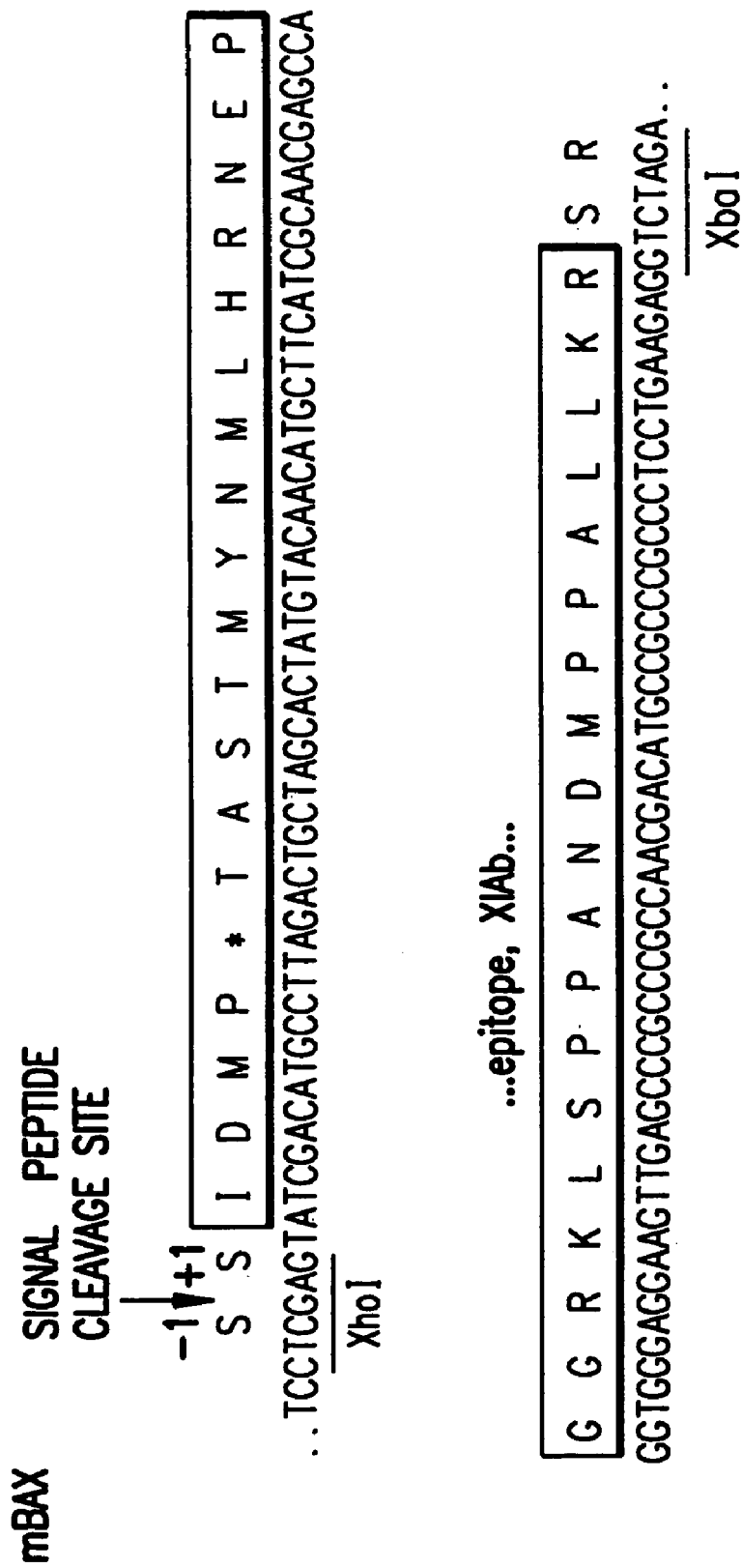
FIG. 12 illustrates the peptide sequence encoded in the mBAX vector situated at the N-terminus of mature pIII protein.

The mBAX vector was created by generating cloning sites in gene III of the M13 mp18 vector (Messing, J., 1991, Gene 100:3–12) in the manner of Fowlkes et al., 1992, Biotechniques 13:422–427. The mBAX vector displays a peptide sequence at the N-terminus of the mature pIII protein that encodes the epitope for the mouse monoclonal antibody 7E11 (see FIG. 12); it includes the stop codon TAG in the coding region, which is suppressed in E. coli carrying suppressor tRNA gene mutations known as supE or supF. There are no other stop codons in the mBAX genome. The mBAX vector also carries a segment of the alpha fragment of β-galactosidase; bacterial cells expressing the omega fragment of β-galactosidase that are infected by a bacteriophage that expresses the alpha fragment convert the clear X-Gal substrate into an insoluble blue precipitate. Thus, plaques of such bacteriophage on such cells appear blue.

Recombinant mBAX molecules can be distinguished easily from non-recombinant molecules due to the TAG codon in the XhoI-XbaI segment in gene III of mBAX. When recombinants are generated by replacing the XhoI-XbaI fragment with oligonucleotides encoding random peptides, the recombinants can be grown in bacteria with (e.g., DH5αF') or without (e.g., JS5) suppressor tRNA mutant genes. On the other hand, the non-recombinant mBAX molecules fail to produce plaques on bacterial lawns where the bacteria (e.g., JS5) lack such suppressor genes. This is because in JS5, the TAG codon serves as a stop codon to yield a truncated pIII molecule during translation; since pIII is an essential protein component of viable M13 viral particles, no plaques will form.

The GST-dystrophin WW domain fusion protein (3–10 μg) was immobilized on the surface of a microtiter dish with 100 ml of 100 mM NaHCO$_3$ (pH 8.5) for 1–3 hours at 25° C. or overnight at 4° C. To minimize evaporation, the wells were sealed with Scotch tape. Next, the non-specific binding sites on the well surfaces were blocked with the addition of 150 μl of 1.0% bovine serum albumin (BSA) in 100 mM NaHCO$_3$ for 1–3 hours at 25° C. or overnight at 4° C. The solution was discarded by inverting the plate and shaking out its contents; the residual liquid was removed by slapping the inverted plate on a mat of paper towels several times. The wells were washed several times with PBS-0.1% Tween 20 to remove unbound protein. Approximately $10^{12}$ pfu of CW1 phage particles were added to 150 μl PBS-0.1% Tween 20 in each well and incubated at 25° C. for 1–3 hours. The non-binding phage were washed away with excess PBS-0.1% Tween 20. Bound phage were eluted by adding 50 μl of 50 mM glycine-HCl (pH 2.0) to each well and incubating 5 minutes at 65° C. The solution was transferred to a new well containing 50 μl of 200 mM NaPO$_4$ buffer (pH 7.5) to neutralize the pH. This protocol represents one round of affinity selection, also termed "panning".

Before the next rounds of affinity selection, the phage recovered in the first round were amplified. To amplify the recovered phage, they were added to 200 μl of an overnight culture of F' E. coli (e.g. DH5αF'), and the mixture transferred to 5 ml of 2xYT. After incubation 6–8 hours at 37° C., the tubes were centrifuged and the supernatant transferred to a new tube. This supernatant was used in succeeding rounds of selection. To minimize proteolytic degradation of displayed peptides, the cultures were not incubated longer than 8 hours.

For rounds two and three, the target GST-dystrophin WW domain fusion protein was immobilized on microtiter wells as described above for the first round and 100 μl of culture supernatant (i.e., $10^{11-1012}$ pfu) was added to each well. The plate was incubated for 1–3 hours at 25° C. The non-binding phage were washed away and the bound phage were eluted and pH neutralized as described above. The recovered phage were used directly for a third round of screening.

To obtain individual plaques from the affinity selection experiments, the final solution containing recovered phage was serially diluted across a microtiter plate and pronged onto a bacterial lawn. The wells of a sterile microtiter plate were individually filled with 80 μl of PBS using a 12-channel multipipetter. Twenty microliters of recovered phage were added to the wells in column #1, mixed, and 20 μl transferred to the adjacent wells in column #2. The serial dilutions were repeated five additional times. In this way, one may perform 6 separate 10-fold dilution series. A petri plate was repared by adding 3 ml liquefied 1.2% top agar and 200 μl of DH5αF' cells from an overnight culture, 25 μl of 20 mg/ml IPTG and 25 μl of 20 mg/ml X-gal, and pouring over a 2xYT agar plate. After the surface of the plate hardened, a flame-sterilized 48-pronger was placed into the microtiter plate dilution series, and carefully rested onto the petri plate. The plaques were incubated overnight at 37° C. Individual plaques were cored and used to generate clonal phage stocks.

The inserts of the dystrophin WW domain-binding phage were sequenced via standard DNA sequencing techniques and the corresponding amino acid sequences of the inserts determined. Six of these peptides corresponding to the determined sequences were synthesized and biotinylated. The sequences of these peptides are shown below.

| | |
|---|---|
| SLQWMDGVGWYME | (SEQ ID NO:64) |
| RWAWDDGWMFGSV | (SEQ ID NO:65) |
| SGLEGWYWERGWV | (SEQ ID NO:66) |
| SIWEMGXDWWARP | (SEQ ID NO:67) |
| RMSWWEEWEFGLG | (SEQ ID NO:68) |
| SWGLDGWLVDGWS | (SEQ ID NO:69) |

These biotinylated peptides were complexed with streptavidin and used to screen a λEXlox mouse 16 day embryo cDNA expression library (obtained from Novagen, Madison, Wis.) according to the methods of Section 6.1. In this way, cDNA clones expressing proteins capable of binding to these peptides were identified and isolated.

6.3. Cross Affinity Mapping

To determine the ligand preferences of the novel WW omain-containing clones described in Sections 6.1 and 6.1.1, as well as addressing the issue of whether peptides containing PPPPY (SEQ ID NO:3)-like motifs derived from a variety of proteins could also serve as recognition units and bind to these clones, a cross affinity mapping experiment was performed (FIGS. 15A–D). The peptides shown in FIGS. 15A–D were synthesized, biotinylated, complexed with streptavidin-alkaline phosphatase, and tested in an ELISA based assay for their ability to bind to the twelve individual novel WW domains of WWP1, WWP2, WWP3 and WWP4 which were expressed as GST fusion proteins. The ELISA based cross-affinity experiments were performed essentially as described by Sparks et al. (1996, Proc. Natl. Acad. Sci. 93:1540–1544) with the following modifications. Briefly, microtiter wells were coated with 1–5 μg of fusion protein in 100 mM NaHCO$_3$, blocked with Super-Block TBS (Pierce) and washed four times with PBS, 0.05% Tween 20. Specific peptide-streptavidin/alkaline phosphatase complexes were added as above and unbound complexes washed five times with PBS, 0.05% Tween 20. Following addition of PNP substrate (p-nitrophenyl phosphate, Kirkegard & Perry Labs), peptide binding was quantitated after 30 min. at O.D. 405 nm. Relative binding measurements from three independent determinations were assigned to a scale as follows: O.D. units 0–0.5=(−), 0.5–1.0=(+), 1.0–2.0=(++), 2.0–3.0=(+++), >3.0=(++++). Peptide binding to human Fyn and Lyn SH3 and SH2 domains was assessed by a filter binding assay (see Section 6.1 and Sparks et al., 1996, Proc. Natl. Acad. Sci 93:1540–1544). Peptide sequences used in cross-affinity experiments correspond to segments of the following genes: RasGap (Database accession # P20936), AP-2 (P05549), p53BP-2 (U09582), IL-6Rα (P22272), voltage-gated chloride channel CLCN5 (X91906), IL-2Rγ (D111086), RSV (D10652), HTLV-1 (D13784), β-dystroglycan (L19711), Formin (X53599), amiloride-sensitive epithelial Na$^+$ channel ENaCα (P37089), ENaCβ (X87159) and ENaCγ (X87160), muscarinic acetylcholine receptor M4 AChR (P08173), and c-Abl (P00522). Src and Crk SH3 binding peptide sequences were derived from a phage display random peptide library screen (Section 6.1 and Sparks et al., 1996, Proc. Natl. Acad. Sci. 93:1540–1544). Protein sequence homology searches were performed using BLAST (Altschul et al., 1990, J. Mol. Biol. 215:403–410) and PROFILES (Gribskov et al., 1987, Proc. Natl. Acad. Sci. 84:4355–4358) programs.

The results shown in FIGS. 15A and B demonstrate that the WBP-1, WBP-2A, and WBP-2C recognition unit peptides bound to several individual WW domains to varying degrees. However, only the WBP-2A recognition unit peptide bound to the WWP3 WW domain, suggesting that this domain may require additional determinants outside of the core PPPPY (SEQ ID NO:3) motif for peptide ligand binding. In addition, the WBP-2B peptide containing an N-terminal tyrosine residue, relative to the run of prolines, had no binding activity, indicating the necessity for a C-terminal tyrosine in the PPPPY (SEQ ID NO:3) motif. The relative importance of individual proline residues within the PPPPY (SEQ ID NO:3) motif for WW domain binding was assessed by alanine substitution variants for both the WBP-1 an WBP-2A peptides. All of the variants with the exception of the substitution at the third proline position (WBP-1-Pro3) in the PPPPY (SEQ ID NO:3) motif-retained binding activity to the WW domains present in clones WWP1 and WWP2, suggesting a critical role for the third proline residue. Additionally, substitution of the second proline residue of WBP-1 (WBP-1-Pro2) resulted in a loss of binding activity to the WW domains present in clone WWP4. Interestingly, substitution of the second proline residue (WBP-1-Pro2) did not abolish binding to WW domains WWP1.2 and WWP2.3. This was unanticipated in light of the results obtained for the binding of WBP-1 to the YAP WW domain in which both the second and third proline residues are crucial for binding (Chen and Sudol, 1995, Proc. Natl. Acad. Sci. USA 92:7819–7823). This finding suggests that WW domains WWP1.1 and WWP2.3 possess a more promiscuous binding specificity than the WW domains of WWP4 and the YAP WW domain.

Proline substitutions of the WBP-2A peptide indicate that the third proline residue (WBP-2A-Pro4) is absolutely essential for binding to WW domains in WWP1, WWP2, WWP3 and WWP4, whereas substitution of the second proline (WBP-2A-Pro3) is not.

FIGS. 15A–D and FIGS. 24A and B show that peptides containing PPPPY (SEQ ID NO:3) and PPPPY (SEQ ID NO:3)-like motifs found in a variety of regulatory proteins, including RasGap; AP-2 transcription factor; p53 binding protein-2 (p53BP-2); the renal chloride channel CLCN5; the interleukin receptors IL-2R, IL-6R, and IL-7R; dystrophin interacting molecule β-dystroglycan β-dystroglycan-1 and β dystroglycan-2); the retroviral Gag proteins from HTLV-1 and RSV-1; EGR2; FIBNECT; MEL.AG; and Inscuteable; bound to WW domains from one or more of the four novel clones. A peptide from the α, β, and γ subunits of the ENaC amiloride-sensitive Epithelial Na$^+$ channel also bound to WW domains from the novel clones (see FIGS. 24A and 24B). For descriptions of the proteins RasGap, AP-2, pS3BP-2, IL-6Rα, and the CLCN5 chloride channel, see Williams et al., 1988, Genes Dev. 2:1557–1569; Cho et al., 1992, Neuron 9:929–942; Iwabuchi et al., 1994, Proc. Natl. Acad. Sci. USA 91:6098–6102; Sugita et al., 1990, J. Exp. Med. 171:2001–2009; Trahey et al., 1988, Science 242: 1697–1700; Helps, et al., 1995, FEBS Lett. 377:295–300; Lloyd et al., 1996, Nature 379:445–449. Interestingly, although all of these peptides displayed an ability to bind WW domains in general, differences in the specificity and relative binding were evident. In particular, of all the peptides tested, only the CLCN5 peptide showed appreciable binding to the WWP1.4 and WWP2.4 domains. The observation that PPPPY (SEQ ID NO:3) motif-containing peptides from several other proteins did not bind to any WW domain indicates that these interactions are specific and potentially biologically relevant.

Given the small size and high degree of sequence conservation of the WW domain, it is extraordinary that exquisite ligand selectivity is observed. The crystal structure of the human YAP WW domain and its peptide ligand reveals that the hydrophobic residues Y188, L190 and W199 (see FIG. 5) form a binding site in contact with the ligand (Macias et al., 1991, Nature: 382:646–649). In light of this data it is interesting to note that domains WWP1.4 and WWP2.4 which contain a C-terminal phenylalanine residue instead of a tryptophan display a more restrictive ligand binding preference. In addition, the presence of valine or isoleucine residues instead of L190 may also play a role in determining the distinct ligand specificity of the novel WW domains. The presence of multiple WW domains with distinct-ligand specificities in WWP1, WWP2, and WWP4 suggests these proteins may bind to a broad range of cellular targets. Alternatively, multiple WW domains may confer additive binding affinity with target molecules that contain multiple PPPPY ligand motifs.

Of particular note is the demonstration that the HTLV-1 and RSV-1 peptides derived from Gag protein proline-rich "L domain" bind to several WW domains. L domain regions are highly conserved in retroviruses and have been shown to function in a positionally independent manner essential for retroviral budding (Parent et al., 1995, J. Virol. 69:5455–5460). Our results, coupled with a recent report demonstrating the interaction of-the YAP WW domain to the L domain of RSV (Garnier et al., 1996, Nature 381:744–745), suggests a direct role for a WW domain(s)-Gag protein interaction in this process. The interaction of a β-dystroglycan peptide with several WW domains is also of interest. β-dystroglycan, which contains a C-terminal PPPPY (SEQ ID NO:3) motif, was previously shown to interact with the single WW domain present in dystrophin (Einbold et al., 1996, FEBS Lett. 384:1–8). Our results suggest that perhaps several different WW domain-containing proteins can interact with the β-dystroglycan C-terminal PPPPY (SEQ ID NO:3) motif. Recently, a 12 amino acid proline-rich region of formin, a protein encoded by the mouse limb deformity locus (Woychik et al., 1985, Nature 318:36–40), was shown to bind to both SH3 and several novel WW domain-containing proteins (Chan et al. 1996, EMBO J. 15:1045–1054). Significantly, a peptide encompassing the same proline-rich region of formin did not bind to any of our novel WW domains (FIGS. 15A, 15B, and 15D). Since this peptide does not contain a PPPPY (SEQ ID NO:3) motif, this suggests that the novel WW domains herein described, unlike those present in the formin-binding proteins, require PPPPY (SEQ ID NO:3) or a PPPPY (SEQ ID NO:3)-like motif for binding.

Taken together, the above observations suggest that interactions between the regulatory proteins discussed above and WW domain-containing proteins may play a role in the former's regulation in vivo. For example, given the likelihood that WWP1, WWP2, and WWP4 function as E3 ubiquitin-protein ligases, one could invoke a simple model whereby initial substrate specific recognition occurs via WW domain-substrate interaction followed by ubiquitin transfer and subsequent proteolysis.

The positive interaction of peptides containing PPPPY (SEQ ID NO:3)-like motifs derived from the β and γ subunits of the Epithelial Na$^+$ channel with WW domains found in clones WWP1, WWP2, WWP3 and WWP4 (See FIGS. 24A and 24B) is of particular medical interest.

Recently, a number of mutations in both the β and γ subunits of the Epithelial Na$^+$ channel (ENaC) have been demonstrated in patients with an autosomal dominant form of hypertension characterized by elevated renal Na$^+$ reabsorption termed Liddle syndrome (Shimkets et al., 1994, Cell 79:407–414). Specifically, several nonsense mutations leading to the truncation of the cytoplasmic domain of both subunits. Additionally, two missense mutations in the β subunit which change the PPPNY motif to PPLNY (labeled P616L) or to PPPNH (Y618H) in codons 616 and 618 of the β subunit contained within a conserved proline-rich segment of the cytoplasmic domain have been identified (Schild et al., 1995, Proc. Natl. Acad. Sci. 92:5699–5703; Hansson et al., 1995, Proc. Natl. Acad. Sci., 92:11495–11499; and Tamura et al., 1996, Clin. Invest. 97:1780–1784). These mutations result in a 3 to 8-fold increase in Na$^+$ channel activity, reflected in an increase in the total number of active channels. These results suggest that cytoplasmic segments of the β and γ subunits are involved in the normal negative regulation of channel activity via interactions with modulatory protein(s). In fact, Nedd-4 was recently identified as a binding partner to the C-terminus of the rat ENaCβ subunit using the two yeast hybrid system (Staub et al., 1996, EMBO J. 15:2371–2380; and Schild et al., 1996, EMBO J. 15:2381–2387). In addition, as discussed infra, using peptides corresponding to ENaCβ and ENaCγ subunits we have isolated WWP1 and WWP4.

Our observation that mutant peptides (ENaCβ-P616L and ENaCβ-Y618H) containing missense substitutions found in Liddle syndrome patients do not bind to the WW domains in clones WWP1, WWP2 and WWP4 (See FIGS. 24A and 24B) is consistent with the above hypothesis. This result also confirms the observation that the third proline residue and the tyrosine within the PPPPY (SEQ ID NO:3) motif is critical for binding to the WW domain. Other substitutions of the β subunit PPPPY (SEQ ID NO:3) motif and flanking-sequences were also shown to diminish binding to specific WW domains. Thus substitution of the second proline residue of the core PPPPY (SEQ ID NO:3) motif completely abrogated WW domain binding. In addition, mutation of specific residues flanking the C-terminus of the PPPPY (SEQ ID NO:3) motif also led to diminished WW domain binding. These results directly correlate with the activity of various EnaCβ mutants measured by a functional assay in Xenopus oocytes (Snyder et al., 1995, Cell 83:969–978). A PPPPY (SEQ ID NO:3) motif containing peptide from the cytoplasmic domain of the a subunit of EnaC (EnaCα-WT) was also shown to bind to several WW domains suggesting that this subunit may also be regulated by a WW domain-mediated interaction(s). Taken together, the above observations suggest a direct mechanism whereby a WW domain-mediated interaction(s) of a Nedd-4 family member(s) leads to the eventual ubiquitin mediated degradation and negative regulation of the Na$^+$ channel and may lead to an understanding of the molecular pathology of Liddle Syndrome.

FIGS. 26A and 26B present a schematic model of the mechanism by which WW domain mediated interactions of a Nedd-4 family member may lead to negative regulation of the Na$^+$ channel and how mutations associated with Liddle's Syndrome result in a loss of this negative regulation, thereby increasing the number of active Na$^+$ channels in the affected individual when compared to normal individuals. According to this model, Nedd-4 like proteins containing WW domains bind to the wild type Epithelial Na$^+$ channel protein, thereby bringing the HECT domain into the vicinity of the protein where it can mediate ubiquitin tagging of the protein. The ubiquitin tag signals that the protein is to be degraded. This allows for the natural turn-over of the channel protein. However, in Liddle syndrome, the WW Nedd-4 like protein cannot bind to the channel protein due to the missing or mutated proline-rich regions of the channel protein. The protein does not get tagged by ubiquitin and is not-degraded. This results in an overexpression of the channel protein in Liddle syndrome patients.

The specificity of individual WW domains for a PPPPY (SEQ ID NO:3)-like motif sequence is demonstrated by the ability to discriminate between peptides containing SH3 domain consensus PXXP (SEQ ID NO:44) ligand sequences (FIG. 15, Src and Crk entries) as well as generally proline-rich peptides control peptides derived from several proteins including the muscarinic acetylcholine receptor (M4 AChR) and c-Abl. In addition, none of the PPPPY (SEQ ID NO:3)-like motif peptides bound to either Fyn or Lyn, which contain both SH3 and SH2 domains. Taken together, these results suggest that the PPPPY (SEQ ID NO:3) motif represents a distinct binding sequence for WW modular protein domains.

To examine the ligand preferences of the PPPPY (SEQ ID NO:3)-like motif contained in the HECT domain of WWP2 and WWP4, methods as set forth in Section 6.1 supra were followed to biotinylate and assay peptides corresponding to these motifs. Peptides corresponding to the wild-type PPPPY-like domain of WWP2 and WWP4 were designated bWW061 and bWW059, respectively. Alanine substitution peptide variants of the tyrosine residue of the PPPPY-like domains of WWP2 and WWP4 were designated bWW062 and bWW060, respectively. The results shown in FIG. 25 demonstrate that the peptides corresponding to the PPPPY-like motif in the HECT domains of both WWP4 and WWP2 bind to individual WW domains in WWP1, WWP2 and WWP4. Noticeably, the peptide corresponding to the PPPPY-like motif in the WWP4 HECT domain binds to the individual WW domains of WWP1.1, WWP1.4, WWP2.1, WWP2.2, WW2.4 (O.D. after 30 minutes at 405 nm was 3.0), WWP4.1, WWP4.2, and WWP4.3. The observation that alanine substitution of the tyrosine in the HECT domain PPPPY-like motifs of both WWP2 and WWP4 abolished binding activity to the WW domains of WWP1, WWP2, and WWP4, suggests that this tyrosine plays a critical role in the binding interaction between the HECT domain PPPPY-like motif and the WW domains.

The presence of a critical tyrosine residue in the PPPPY (SEQ ID NO:3) motif raises the question of whether tyrosine phosphorylation can modulate WW domain binding. Although it is not known whether PPPPY (SEQ ID NO:3) motifs are phosphorylated in vivo, the present inventors have observed that the presence of a phosphotyrosine residue in the pWBP-1 peptide (indicated by a lower case "p" in FIGS. 15A and 15B) abolishes binding to WWP1, WWP2 and WWP4. Moreover, binding of the pWBP-1 peptide could be restored by removal of the phosphate moiety either with prior treatment of the free peptide or peptide bound to a strepavidin-HRP conjugate with alkaline phosphatase. These results demonstrate a potential regulatory role for tyrosine phosphorylation in modulating WW domain-ligand interactions.

The interaction of peptides containing PPPPY (SEQ ID NO:3) and PPPPY (SEQ ID NO:3)-like motifs from several proteins with the WW domains in clones WWP1 and WWP2 suggests a role for ubiquitin-mediated degradation of these proteins. In this respect, it is noteworthy that several cell membrane proteins including the PDGF receptor and yeast α factor receptor Ste2p, are subject to ubiquitination and eventual degradation upon ligand binding (Mori et al., 1992, J. Biol. Chem. 267:6429–6434; Hicke and Riezman, 1996, Cell 84:277–287).

To further define the binding preferences of the WW domains of the newly identified proteins WWP1, WWP2, and WWP3, the present inventors inspected a number of published amino acid sequences and identified proline-rich stretches of amino acids that resembled consensus WW domain binding sequences. See Chen and Sudol, 1995, Proc. Natl. Acad. Sci. USA 92:7819–7823 for a discussion of consensus WW domain binding sequences. Peptides comprising these proline-rich sequences were synthesized and tested by the methods of the present invention for their ability to specifically bind to the novel WW domains described in Sections 6.1 and 6.1.1. The results are shown in FIG. 7. As can be seen, in many cases the synthesized peptides were able to bind to the novel WW domains. This indicates that those synthesized peptides could have been used to identify those novel WW domains from sources of polypeptides.

In further attempts to define the binding preference of the newly identified WW domains, biased phage display libraries (identified in FIG. 27 as cw, pp and xy) were screened to identify peptide sequences that functioned as recognition units of the WW domains; WWP1.1, WWP1.4 and WWP3. These individual domains were expressed as GST fusion proteins and assayed for binding activity according to the methods set forth herein (see, e.g., Sections 6.1, 6.1.1 and 6.2). FIG. 27 presents the recognition unit peptides identified by each of these respective screens and the relative binding affinity of each of these recognition units for the tested WW domain, which was determined using techniques described infra.

6.4. Materials Used in Section 6 and its Subsections

| 2xYT media (1L) | |
| --- | --- |
| Bacto tryptone | 16 g |
| Yeast Extract | 10 g |
| NaCl | 5 g |
| 2xYT agar plates | |
| 2xYT + 15 g agar/L | |
| 2xYT top agarose (8%) | |
| 2xYT + 8 g agarose/L | |
| SDS/DTT loading buffer | |
| (10 mL of 5× solution) | |
| .5 M Tris base | 0.61 g |
| 8.5% SDS | 0.85 g |
| 27.5% sucrose | 2.75 g |
| 100 mM DTT | 0.154 g |
| .03% Bromophenol Blue | 3.0 mg |
| Overnight cell cultures: | |
| Inoculate media with one isolated colony of appropriate cell type and incubate 37° C. O/N with shaking BL21 (DE3) pLysE 2xYT media | |
| maltose | 0.2% |
| MgSO$_4$ | 10 mM |
| Chloramphenicol | 34 µg/ml |
| Kanamycin | 50 µg/ml |

6.5. Biotinylated Peptide Detection Using Tyramide Amplification System

The following protocol is an alternative to the methods described herein that utilize alkaline phosphatase to detect the binding of recognition units and WW domains. It permits the use of recognition units that are phosphopeptides.

Materials:

TSA-Tyramide Signal Amplification System (Dupont NEL-700); Streptavidin-Peroxidase, SA-P, conjugate 1 mg/ml $H_2O$ (Sigma S-5512); Streptavidin-Alkaline Phosphatase, SA-AP, conjugate 1 mg/ml $H_2O$ (Sigma S-2890); Dulbecco's PBS (Sigma D1408); PBS+0.05% Triton-X100, PBS/Tr; PBS/Tr+20% DMSO; SuperBlock™ Blocking Buffer in TBS (Pierce 37535); d-Biotin 0.1 mM; Biotinylated Peptide probe 0.1 mM; Plaque lifts on Nitrocellulose (Schleicher & Schuell BA85, 0.45 um, 85 mm); SIGMA FAST™ BCIP/NBT Buffered Substrate Tablets (Sigma B-5655)

Method:
1. Wash Plaque lifts in PBS/Tr 3×5–10 min at Room Temperature (RT) with agitation.
2. Block filters in 50–75 ml SuperBlock at RT for 60–90 min or store at 4° C. until needed.
3. Prepare SA-P/biotinylated peptide probe complex while filters are in block.
   Mix 93.6 µl SA-P 1 mg/ml and 45 µl 0.1 mM Biotinylated Peptide probe.
   Incubate 30 min at 4° C.
   Add 30 µl 0.1 mM d-Biotin and mix.
   Incubate 15 min at 4° C.
   Add above complex to 60 ml SuperBlock.
4. Add filters to SA-P/biotinylated peptide probe complex and incubate 2 hrs at RT with agitation.
5. Wash Plaque lifts in PBS/Tr 5×10 min at Room Temperature (RT) with agitation.
6. Place each filter in a petri dish and add 5 ml Biotinyl Tyramide reagent prepared as follows;
   Mix equal volumes of 2× amplification diluent and deionized water.
   Add 40 µl Biotinyl Tyramide reagent/5 ml amplification diluent and mix.
7. Incubate Biotinyl Tyramide reagent on filters for 10 min at RT. Exposure time and concentration of Biotinyl Tyramide reagent of filters may have to be determined empirically.
8. Wash filters thoroughly for:
   4×10 min in 15 ml PBS/tr+20% DMSO.
   3×5 min in 15 ml PBS/tr.
   2×3 min in 10 ml SuperBlock.
9. Add filters to SA-AP diluted in SuperBlock (0.33 µl 1 mg/ml stock per 20 ml SuperBlock). Exposure time and concentration of SA-AP to filters may have to be determined empirically. Use about 10 ml per filter.
10. Incubate 30 min at RT.
11. Wash filters thoroughly for:
    4×5 min in 15 ml PBS/tr.
    3×5 min in PBS.
12. Develop filters using SIGMA FAST™BCIP/NBT Buffered Substrate Tablets. Use 60 ml for 10 filters.
    Dissolve 1 tablet in 10 ml deionized water.
    Allow development to proceed for 5–30 min at RT with agitation until desired signal to noise levels are visually obtained.
    Rinse filters in water and air dry.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

---

What is claimed is:

1. A kit comprising a plurality of purified polypeptides, each polypeptide in a separate container, and each polypeptide comprising a WW domain of a different sequence, wherein said polypeptide comprises the amino acid sequence of SEQ ID NO: 39, and wherein the different WW domains have a selective binding affinity for the same peptide recognition unit, and wherein said specific binding affinity is between about 1 nM and about 1 mM.

2. The kit of claim 1 in which the plurality of polypeptides comprises polypeptides that comprise amino acid sequences selected from the group consisting of: SEQ ID NO: 46, 48, 50, and 126.

3. The kit of claim 1 in which the plurality of polypeptides comprises polypeptides that comprise amino acid sequences selected from the group consisting of: SEQ ID NO: 30, 32, 33, 34, 35, 36, 37, 38, 127, 128, 129, and 131.

4. The kit of claim 1 in which the plurality of polypeptides comprises polypeptides that consist of amino acid sequences selected from the group consisting of SEQ ID NO: 46, 48, 50, and 126.

5. The kit of claim 1 in which the plurality of polypeptides comprises polypeptides that consist amino acid sequences selected from the group consisting of: SEQ ID NO: 30, 32, 33, 34, 35, 36, 37, 38, 127, 128, 129, and 131.

6. The kit of claim 1 in which each of the WW domains is a WW domain of a polypeptide selected from the group consisting of: SEQ ID NO: 46, 48, 50, and 126.

7. The kit of claim 1 in which the plurality of polypeptides consists of amino acid sequences selected from the group consisting of: SEQ ID NO: 30, 32, 33, 34, 35, 36, 37, 38, 127, 128, 129, and 131, and amino acid residues 162–197 of SEQ ID NO: 46.

8. A purified polypeptide comprising a WW domain, said WW domain comprising an amino acid sequence selected from the group consisting of: SEQ ID NO: 30, 32, 33, 34, 35, 36, 37, 38, 127, 128, 129, and 131.

9. A purified polypeptide comprising a WW domain, said WW domain consisting of an amino acid sequence selected from the group consisting of: SEQ ID NO: 30, 32, 33, 34, 35, 36, 37, 38, 127, 128, 129, and 131.

10. A purified polypeptide comprising a WW domain, said polypeptide comprising an amino acid sequence selected from the group consisting of SEQ ID NO: 46, 48, 50, and 126.

11. A purified polypeptide comprising a WW domain, said polypeptide consisting of an amino acid sequence selected from the group consisting of SEQ ID NO: 46, 48, 50, and 126.

12. A purified molecule comprising a WW domain of a polypeptide, and further comprising a detectable label, said polypeptide consisting of an amino acid sequence selected from the group consisting of: SEQ ID NO: 46, 48, 50, or 126.

13. A purified molecule comprising a WW domain of a polypeptide, and further comprising a detectable label, said polypeptide comprising an amino acid sequence selected from the group consisting of: SEQ ID NO: 46, 48, 50, or 126.

14. A purified molecule comprising a WW domain of a polypeptide, and further comprising a detectable label, said polypeptide consisting of an amino acid sequence selected from the group consisting of SEQ ID NO: 30, 32, 33, 34, 35, 36, 37, 38, 127, 128, 129, and 131.

15. A purified molecule comprising a WW domain of a polypeptide, and further comprising a detectable label, said polypeptide comprising an amino acid sequence selected from the group consisting of SEQ ID NO: 30, 32, 33, 34, 35, 36, 37, 38, 127, 128, 129, and 131.

16. A purified molecule comprising a WW domain of a polypeptide, and further comprising a detectable label, wherein the WW domain is the WW domain of a polypeptide selected from the group consisting of SEQ ID NO: 46, 48, 50, and 126.

17. A fusion protein comprising (a) an amino acid sequence comprising a WW domain of a polypeptide consisting of the amino acid sequence of SEQ ID NO: 46, 48, 50 or 126, joined via a peptide bond to (b) an amino acid sequence of at least six amino acids from a different polypeptide.

18. A fusion protein comprising (a) an amino acid sequence selected from the group consisting of SEQ ID NO: 46, 48, 50, and 126, joined via a peptide bond to (b) an amino acid sequence of at least six amino acids from a different polypeptide.

19. A purified polypeptide comprising an amino acid sequence selected from the group consisting of SEQ ID NO: 30, 32, 33, 34, 35, 36, 37, 38, 127, 128, 129, and 131.

20. A purified polypeptide consisting of an amino acid sequence selected from the group consisting of SEQ ID NO: 30, 32, 33, 34, 35, 36, 37, 38, 127, 128, 129, and 131.

* * * * *

```
                      SEQUENCE LISTING (1) GENERAL INFORMATION:

(iii) NUMBER OF SEQUENCES: 233

(2) INFORMATION FOR SEQ ID NO: 1:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 1:

Pro Gly Thr Pro Pro Leu Asn Tyr Asp Ser Leu Arg Leu
1               5                   10

(2) INFORMATION FOR SEQ ID NO: 2:

(i) SEQUENCE CHARACTERISTICS:
        (A) LENGTH: 26 amino acids
        (B) TYPE: amino acid
        (C) STRANDEDNESS: <Unknown>
        (D) TOPOLOGY: unknown (ii) MOLECULE TYPE: peptide
```

```
    (ix) FEATURE:
         (A) NAME/KEY: Modified-site
         (B) LOCATION: 10
         (D) OTHER INFORMATION: /note= "Xaa May Be Either Lys or
             Arg."

(ix) FEATURE:
         (A) NAME/KEY: Modified-site
         (B) LOCATION: 12
         (D) OTHER INFORMATION: /note= "Xaa May Be Either Tyr or
             Phe."

(ix) FEATURE:
         (A) NAME/KEY: Modified-site
         (B) LOCATION: 13
         (D) OTHER INFORMATION: /note= "Xaa May Be Either Tyr or
             Phe."

(ix) FEATURE:
         (A) NAME/KEY: Modified-site
         (B) LOCATION: 15
         (D) OTHER INFORMATION: /note= "Xaa May Be Either Asn or
             Asp."

(ix) FEATURE:
         (A) NAME/KEY: Modified-site
         (B) LOCATION: 18
         (D) OTHER INFORMATION: /note= "Xaa May Be Either Thr or
             Ser."

(ix) FEATURE:
         (A) NAME/KEY: Modified-site
         (B) LOCATION: 19
         (D) OTHER INFORMATION: /note= "Xaa May Be Either Lys or
             Arg."

(ix) FEATURE:
         (A) NAME/KEY: Modified-site
         (B) LOCATION: 21
         (D) OTHER INFORMATION: /note= "Xaa May Be Either Thr or
             Ser."

(ix) FEATURE:
         (A) NAME/KEY: Modified-site
         (B) LOCATION: 22
         (D) OTHER INFORMATION: /note= "Xaa May Be Either Thr, Gln,
             or Ser."

(xi) SEQUENCE DESCRIPTION: SEQ ID NO: 2:

Trp Xaa Xaa Xaa Xaa Xaa Xaa Xaa Gly Xaa Xaa Xaa Xaa Xaa Xaa Xaa
1               5                   10                  15

Xaa Xaa Xaa Xaa Xaa Xaa Trp Xaa Xaa Pro
            20                  25

(2) INFORMATION FOR SEQ ID NO: 3:

(i) SEQUENCE CHARACTERISTICS:
         (A) LENGTH: 5 amino acids
         (B) TYPE: amino acid
         (C) STRANDEDNESS: <Unknown>
         (D) TOPOLOGY: unknown (ii) MOLECULE TYPE: peptide (xi) SEQUENCE DESCRIPTION: SEQ ID NO: 3:

Pro Pro Pro Pro Tyr
1               5

(2) INFORMATION FOR SEQ ID NO: 4:

(i) SEQUENCE CHARACTERISTICS:
         (A) LENGTH: 129 base pairs
         (B) TYPE: nucleic acid
         (C) STRANDEDNESS: single
```

(D) TOPOLOGY: linear (ii) MOLECULE TYPE: DNA (genomic)

(xi) SEQUENCE DESCRIPTION: SEQ ID NO: 4:

TCCTCGAGTA TCGACATGCC TTAGACTGCT AGCACTATGT ACAACATGCT TCATCGCAAC      60

GAGCCAGGTG GGAGGAAGTT GAGCCCGCCC GCCAACGACA TGCCGCCCGC CCTCCTGAAG     120

AGGTCTAGA                                                            129

(2) INFORMATION FOR SEQ ID NO: 5:

(i) SEQUENCE CHARACTERISTICS:
            (A) LENGTH: 35 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 5:

Thr Ala Ser Thr Met Tyr Asn Met Leu His Arg Asn Glu Pro Gly Gly
1               5                  10                  15

Arg Lys Leu Ser Pro Pro Ala Asn Asp Met Pro Pro Ala Leu Leu Lys
            20                  25                  30

Arg Ser Arg
        35

(2) INFORMATION FOR SEQ ID NO: 6:

(i) SEQUENCE CHARACTERISTICS:
            (A) LENGTH: 13 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 6:

His Pro Gly Thr Pro Pro Pro Pro Tyr Thr Val Gly Pro
1               5                  10

(2) INFORMATION FOR SEQ ID NO: 7:

(i) SEQUENCE CHARACTERISTICS:
            (A) LENGTH: 13 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 7:

Pro Gly Tyr Pro Tyr Pro Pro Pro Pro Glu Phe Tyr
1               5                  10

(2) INFORMATION FOR SEQ ID NO: 8:

(i) SEQUENCE CHARACTERISTICS:
            (A) LENGTH: 13 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 8:

```
Tyr Val Gln Pro Pro Pro Pro Tyr Pro Gly Pro Met
1               5                   10
```

(2) INFORMATION FOR SEQ ID NO: 9:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 9:

```
Ser Gly Ser Gly Pro Gly Thr Pro Pro Pro Tyr Thr Val Gly Pro
1               5                   10                  15
Gly Tyr
```

(2) INFORMATION FOR SEQ ID NO: 10:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 10:

```
Ser Gly Ser Gly Tyr Val Gln Pro Pro Pro Pro Tyr Pro Gly Pro
1               5                   10                  15
Met
```

(2) INFORMATION FOR SEQ ID NO: 11:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 11:

```
Ser Gly Ser Gly Pro Gly Thr Pro Tyr Pro Pro Pro Glu Phe Tyr
1               5                   10                  15
```

(2) INFORMATION FOR SEQ ID NO: 12:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 12:

```
Val Pro Leu Pro Ala Gly Trp Glu Met Ala Lys Thr Ser Ser Gly Gln
1               5                   10                  15
Arg Tyr Phe Leu Asn His Ile Asp Gln Thr Thr Thr Trp Gln Asp Pro
            20                  25                  30
Arg Lys Ala Met Leu Ser
            35
```

(2) INFORMATION FOR SEQ ID NO: 13:

(i) SEQUENCE CHARACTERISTICS:
    (A) LENGTH: 38 amino acids
    (B) TYPE: amino acid
    (C) STRANDEDNESS: <Unknown>
    (D) TOPOLOGY: unknown (ii) MOLECULE TYPE: peptide (xi) SEQUENCE DESCRIPTION: SEQ ID NO: 13:

```
Val Pro Leu Pro Pro Gly Trp Glu Met Ala Lys Thr Pro Ser Gly Gln
1               5                   10                  15
Arg Tyr Phe Leu Asn His Ile Asp Gln Thr Thr Thr Trp Gln Asp Pro
            20                  25                  30
Arg Lys Ala Met Leu Ser
        35
```

(2) INFORMATION FOR SEQ ID NO: 14:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 14:

```
Gly Pro Leu Pro Asp Gly Trp Glu Gln Ala Met Thr Gln Asp Gly Glu
1               5                   10                  15
Ile Tyr Tyr Ile Asn His Lys Asn Lys Thr Thr Ser Trp Leu Asp Pro
            20                  25                  30
Arg Leu Asp Pro Arg Phe
        35
```

(2) INFORMATION FOR SEQ ID NO: 15:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 15:

```
Val Pro Leu Pro Ala Gly Trp Glu Met Ala Lys Thr Ser Ser Gly Gln
1               5                   10                  15
Arg Tyr Phe Leu Asn His Asn Asp Gln Thr Thr Thr Trp Gln Asp Pro
            20                  25                  30
Arg Lys Ala Met Leu Ser
        35
```

(2) INFORMATION FOR SEQ ID NO: 16:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 16:

```
Gly Pro Leu Pro Asp Gly Trp Glu Gln Ala Met Thr Gln Asp Gly Glu
1               5                   10                  15
```

```
Val Tyr Tyr Ile Asn His Lys Asn Lys Thr Thr Ser Trp Leu Asp Pro
            20                  25                  30

Arg Leu Asp Pro Arg Phe
            35

(2) INFORMATION FOR SEQ ID NO: 17:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 17:

Ser Pro Leu Pro Pro Gly Trp Glu Glu Arg Gln Asp Val Leu Gly Arg
1               5                  10                  15

Thr Tyr Tyr Val Asn His Glu Ser Arg Arg Thr Gln Trp Lys Arg Pro
            20                  25                  30

Ser Pro Asp Asp Asp Leu
            35

(2) INFORMATION FOR SEQ ID NO: 18:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 18:

Ser Pro Leu Pro Pro Gly Trp Glu Glu Arg Gln Asp Ile Leu Gly Arg
1               5                  10                  15

Thr Tyr Tyr Val Asn His Glu Ser Arg Arg Thr Gln Trp Lys Arg Pro
            20                  25                  30

Thr Arg Gln Asp Asn Leu
            35

(2) INFORMATION FOR SEQ ID NO: 19:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 19:

Gly Arg Leu Pro Pro Gly Trp Glu Arg Arg Thr Asp Asn Phe Gly Arg
1               5                  10                  15

Thr Tyr Tyr Val Asp His Asn Thr Arg Thr Thr Thr Trp Lys Arg Pro
            20                  25                  30

Thr Leu Asp Gln Thr Glu
            35

(2) INFORMATION FOR SEQ ID NO: 20:

(i) SEQUENCE CHARACTERISTICS:
        (A) LENGTH: 38 amino acids
        (B) TYPE: amino acid
```

```
          (C) STRANDEDNESS: <Unknown>
          (D) TOPOLOGY: unknown (ii) MOLECULE TYPE: peptide (xi) SEQUENCE DESCRIPTION: SEQ ID NO: 20:

Ser Gly Leu Pro Pro Gly Trp Glu Glu Lys Gln Asp Asp Arg Gly Arg
1               5                   10                  15

Ser Tyr Tyr Val Asp His Asn Ser Lys Thr Thr Thr Trp Ser Lys Pro
            20                  25                  30

Thr Met Gln Asp Asp Pro
        35

(2) INFORMATION FOR SEQ ID NO: 21:

(i) SEQUENCE CHARACTERISTICS:
          (A) LENGTH: 38 amino acids
          (B) TYPE: amino acid
          (C) STRANDEDNESS: <Unknown>
          (D) TOPOLOGY: unknown (ii) MOLECULE TYPE: peptide (xi) SEQUENCE DESCRIPTION: SEQ ID NO: 21:

Ser Gly Leu Pro Pro Gly Trp Glu Glu Lys Gln Asp Glu Arg Gly Arg
1               5                   10                  15

Ser Tyr Tyr Val Asp His Asn Ser Arg Thr Thr Thr Trp Thr Lys Pro
            20                  25                  30

Thr Val Gln Ala Thr Val
        35

(2) INFORMATION FOR SEQ ID NO: 22:

(i) SEQUENCE CHARACTERISTICS:
          (A) LENGTH: 38 amino acids
          (B) TYPE: amino acid
          (C) STRANDEDNESS: <Unknown>
          (D) TOPOLOGY: unknown (ii) MOLECULE TYPE: peptide (xi) SEQUENCE DESCRIPTION: SEQ ID NO: 22:

Gly Glu Leu Pro Ser Gly Trp Glu Gln Arg Phe Thr Pro Glu Gly Arg
1               5                   10                  15

Ala Tyr Phe Val Asp His Asn Thr Arg Thr Thr Thr Trp Val Asp Pro
            20                  25                  30

Arg Arg Gln Gln Tyr Ile
        35

(2) INFORMATION FOR SEQ ID NO: 23:

(i) SEQUENCE CHARACTERISTICS:
          (A) LENGTH: 38 amino acids
          (B) TYPE: amino acid
          (C) STRANDEDNESS: <Unknown>
          (D) TOPOLOGY: unknown (ii) MOLECULE TYPE: peptide (xi) SEQUENCE DESCRIPTION: SEQ ID NO: 23:

Gly Phe Leu Pro Lys Gly Trp Glu Val Arg His Ala Pro Asn Gly Arg
1               5                   10                  15

Pro Phe Phe Ile Asp His Asn Thr Lys Thr Thr Thr Trp Glu Asp Pro
            20                  25                  30
```

```
Arg Leu Lys Ile Pro Ala
        35

(2) INFORMATION FOR SEQ ID NO: 24:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 24:

Gly Pro Leu Pro Pro Gly Trp Glu Glu Arg Thr His Thr Asp Gly Arg
1               5                   10                  15

Val Phe Phe Ile Asn His Asn Ile Lys Lys Thr Gln Trp Glu Asp Pro
                20                  25                  30

Arg Leu Gln Asn Val Ala
        35

(2) INFORMATION FOR SEQ ID NO: 25:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 25:

Gly Pro Leu Pro Pro Gly Trp Glu Glu Arg Thr His Thr Asp Gly Arg
1               5                   10                  15

Ile Phe Tyr Ile Asn His Asn Ile Lys Arg Thr Gln Trp Glu Asp Pro
                20                  25                  30

Arg Leu Glu Asn Val Ala
        35

(2) INFORMATION FOR SEQ ID NO: 26:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 26:

Gly Pro Leu Pro Ser Gly Trp Glu Met Arg Leu Thr Asn Thr Ala Arg
1               5                   10                  15

Val Tyr Phe Val Asp His Asn Thr Lys Thr Thr Thr Trp Asp Asp Pro
                20                  25                  30

Arg Leu Pro Ser Ser Leu
        35

(2) INFORMATION FOR SEQ ID NO: 27:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown (ii) MOLECULE TYPE: peptide
```

(xi) SEQUENCE DESCRIPTION: SEQ ID NO: 27:

Thr Ser Val Gln Gly Pro Trp Glu Arg Ala Ile Ser Pro Asn Lys Val
1               5                   10                  15

Pro Tyr Tyr Ile Asn His Glu Thr Gln Thr Thr Cys Trp Asp His Pro
            20                  25                  30

Lys Met Thr Glu Leu Tyr
        35

(2) INFORMATION FOR SEQ ID NO: 28:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 28:

Thr Ser Val Gln Gly Pro Trp Glu Arg Ala Ile Ser Pro Asn Lys Val
1               5                   10                  15

Pro Tyr Tyr Met Asn His Gln Thr Gln Thr Thr Cys Trp Asp His Pro
            20                  25                  30

Lys Met Thr Glu Leu Tyr
        35

(2) INFORMATION FOR SEQ ID NO: 29:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 29:

Thr Ser Val Gln Leu Pro Trp Gln Arg Ser Ile Ser His Asn Lys Val
1               5                   10                  15

Pro Tyr Tyr Ile Asn His Gln Thr Gln Thr Thr Cys Trp Asp His Pro
            20                  25                  30

Lys Met Thr Glu Leu Phe
        35

(2) INFORMATION FOR SEQ ID NO: 30:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 30:

Leu Pro Ser Gly Trp Gly Trp Glu Gln Arg Lys Asp Pro His Gly Arg
1               5                   10                  15

Thr Tyr Tyr Val Asp His Asn Thr Arg Thr Thr Thr Trp Glu Arg Pro
            20                  25                  30

Gln Pro Leu Pro Pro Gly
        35

(2) INFORMATION FOR SEQ ID NO: 31:

(i) SEQUENCE CHARACTERISTICS:
       (A) LENGTH: 38 amino acids
       (B) TYPE: amino acid
       (C) STRANDEDNESS: <Unknown>
       (D) TOPOLOGY: unknown (ii) MOLECULE TYPE: peptide (xi) SEQUENCE DESCRIPTION: SEQ ID NO: 31:

Gln Pro Leu Pro Pro Gly Trp Glu Arg Arg Val Asp Arg Arg
1               5                  10                  15

Val Tyr Tyr Val Asp His Asn Thr Arg Thr Thr Trp Gln Arg Pro
                20                  25                  30

Thr Met Glu Ser Val Pro
        35

(2) INFORMATION FOR SEQ ID NO: 32:

(i) SEQUENCE CHARACTERISTICS:
       (A) LENGTH: 38 amino acids
       (B) TYPE: amino acid
       (C) STRANDEDNESS: <Unknown>
       (D) TOPOLOGY: unknown (ii) MOLECULE TYPE: peptide (xi) SEQUENCE DESCRIPTION: SEQ ID NO: 32:

Gly Pro Leu Pro Pro Gly Trp Glu Lys Arg Val Asp Ser Thr Asp Arg
1               5                  10                  15

Val Tyr Phe Val Asn His Asn Thr Lys Thr Thr Gln Trp Glu Asp Pro
                20                  25                  30

Arg Thr Gln Gly Leu Gln
        35

(2) INFORMATION FOR SEQ ID NO: 33:

(i) SEQUENCE CHARACTERISTICS:
       (A) LENGTH: 38 amino acids
       (B) TYPE: amino acid
       (C) STRANDEDNESS: <Unknown>
       (D) TOPOLOGY: unknown (ii) MOLECULE TYPE: peptide (xi) SEQUENCE DESCRIPTION: SEQ ID NO: 33:

Glu Pro Leu Pro Glu Gly Trp Glu Ile Arg Tyr Thr Arg Glu Gly Val
1               5                  10                  15

Arg Tyr Phe Val Asp His Asn Thr Arg Thr Thr Thr Phe Lys Asp Pro
                20                  25                  30

Arg Asn Gly Lys Ser Ser
        35

(2) INFORMATION FOR SEQ ID NO: 34:

(i) SEQUENCE CHARACTERISTICS:
       (A) LENGTH: 38 amino acids
       (B) TYPE: amino acid
       (C) STRANDEDNESS: <Unknown>
       (D) TOPOLOGY: unknown (ii) MOLECULE TYPE: peptide (xi) SEQUENCE DESCRIPTION: SEQ ID NO: 34:

Asp Ala Leu Pro Ala Gly Trp Glu Gln Arg Glu Leu Pro Asn Gly Arg

```
           1               5              10              15
Val Tyr Tyr Val Asp His Asn Thr Lys Thr Thr Thr Trp Glu Arg Pro
                20                  25                  30

Leu Pro Pro Gly Trp Glu
        35

(2) INFORMATION FOR SEQ ID NO: 35:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 35:

Arg Pro Leu Pro Pro Gly Trp Glu Lys Arg Thr Asp Pro Arg Gly Arg
  1               5                  10                  15

Phe Tyr Tyr Val Asp His Asn Thr Arg Thr Thr Thr Trp Gln Arg Pro
                20                  25                  30

Thr Ala Glu Tyr Val Arg
        35

(2) INFORMATION FOR SEQ ID NO: 36:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 36:

Gly Pro Leu Pro Pro Gly Trp Glu Lys Arg Gln Asp Val Asn Gly Arg
  1               5                  10                  15

Val Tyr Tyr Val Asn His Asn Thr Arg Thr Thr Gln Trp Glu Asp Pro
                20                  25                  30

Arg Thr Gln Gly Met Ile
        35

(2) INFORMATION FOR SEQ ID NO: 37:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 37:

Pro Ala Leu Pro Pro Gly Trp Glu Met Lys Tyr Thr Ser Glu Gly Val
  1               5                  10                  15

Arg Tyr Phe Val Asp His Asn Thr Arg Thr Thr Thr Phe Lys Asp Pro
                20                  25                  30

Arg Pro Gly Phe Glu Ser
        35

(2) INFORMATION FOR SEQ ID NO: 38:

(i) SEQUENCE CHARACTERISTICS:
        (A) LENGTH: 38 amino acids
```

```
          (B) TYPE: amino acid
          (C) STRANDEDNESS: <Unknown>
          (D) TOPOLOGY: unknown (ii) MOLECULE TYPE: peptide (xi) SEQUENCE DESCRIPTION: SEQ ID NO: 38:

Gly Pro Leu Pro Glu Asn Trp Glu Met Ala Tyr Thr Glu Asn Gly Glu
1               5                   10                  15

Val Tyr Phe Ile Asp His Asn Thr Lys Thr Thr Ser Trp Leu Asp Pro
            20                  25                  30

Arg Cys Leu Asn Lys Gln
        35

(2) INFORMATION FOR SEQ ID NO: 39:

(i) SEQUENCE CHARACTERISTICS:
          (A) LENGTH: 33 amino acids
          (B) TYPE: amino acid
          (C) STRANDEDNESS: <Unknown>
          (D) TOPOLOGY: unknown (ii) MOLECULE TYPE: peptide (ix) FEATURE:
          (A) NAME/KEY: Modified-site
          (B) LOCATION: 5
          (D) OTHER INFORMATION: /note= "A Hydrophobic Amino Acid."

(ix) FEATURE:
          (A) NAME/KEY: Modified-site
          (B) LOCATION: 12
          (D) OTHER INFORMATION: /note= "A Hydrophobic Amino Acid."

(ix) FEATURE:
          (A) NAME/KEY: Modified-site
          (B) LOCATION: 13
          (D) OTHER INFORMATION: /note= "A Hydrophobic Amino Acid."

(ix) FEATURE:
          (A) NAME/KEY: Modified-site
          (B) LOCATION: 14
          (D) OTHER INFORMATION: /note= "A Hydrophobic Amino Acid."

(ix) FEATURE:
          (A) NAME/KEY: Modified-site
          (B) LOCATION: 16
          (D) OTHER INFORMATION: /note= "A Hydrophobic Amino Acid."

(ix) FEATURE:
          (A) NAME/KEY: Modified-site
          (B) LOCATION: 20
          (D) OTHER INFORMATION: /note= "A Polar Amino Acid."

(ix) FEATURE:
          (A) NAME/KEY: Modified-site
          (B) LOCATION: 25
          (D) OTHER INFORMATION: /note= "A Hydrophobic Amino Acid."

(ix) FEATURE:
          (A) NAME/KEY: Modified-site
          (B) LOCATION: 28
          (D) OTHER INFORMATION: /note= "A Hydrophobic Amino Acid."

(ix) FEATURE:
          (A) NAME/KEY: Modified-site
          (B) LOCATION: 31
          (D) OTHER INFORMATION: /note= "A Hydrophobic Amino Acid."

(ix) FEATURE:
          (A) NAME/KEY: Modified-site
          (B) LOCATION: 33
          (D) OTHER INFORMATION: /note= "A Hydrophobic Amino Acid."

(xi) SEQUENCE DESCRIPTION: SEQ ID NO: 39:
```

```
Xaa Xaa Leu Pro Thr Gly Trp Glu Xaa Xaa Thr Thr Thr Gly Thr
1               5                   10                  15

Xaa Tyr Tyr His Xaa His Asn Thr Thr Thr Thr Trp Xaa Thr Pro
            20              25              30

Thr
```

(2) INFORMATION FOR SEQ ID NO: 40:

(i) SEQUENCE CHARACTERISTICS:
        (A) LENGTH: 33 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO: 40:

```
CTGTGCGGAT CCAAGACCTG AACACCAGAT GGA                              33
```

(2) INFORMATION FOR SEQ ID NO: 41:

(i) SEQUENCE CHARACTERISTICS:
        (A) LENGTH: 27 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO: 41:

```
CTGTGCGAAT TCCAAAGTCT CGAACAT                                     27
```

(2) INFORMATION FOR SEQ ID NO: 42:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: unknown (ii) MOLECULE TYPE: peptide (ix) FEATURE:
        (A) NAME/KEY: Modified-site
        (B) LOCATION: 2
        (D) OTHER INFORMATION: /note= "Xaa May Be Either Ser or
            Arg."

(xi) SEQUENCE DESCRIPTION: SEQ ID NO: 42:

```
Ser Xaa Xaa Xaa Xaa Xaa Xaa Xaa Xaa Xaa Xaa Xaa Xaa Xaa Ser
1               5                   10                  15

Arg Pro Thr
```

(2) INFORMATION FOR SEQ ID NO: 43:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 43:

```
Xaa Xaa Pro Xaa Tyr
1               5
```

(2) INFORMATION FOR SEQ ID NO: 44:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 44:

Pro Xaa Xaa Pro
1

(2) INFORMATION FOR SEQ ID NO: 45:

(i) SEQUENCE CHARACTERISTICS:
        (A) LENGTH: 2052 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 45:

```
GACTAATCAT GTACCTACAA GCACTCTAGT CCAAAACTCA TGCTGCTCGT ATGTAGTTAA      60

TGGAGACAAC ACACCTTCAT CTCCGTCTCA GGTTGCTGCC AGACCCAAAA ATACACCAGC     120

TCCAAAACCA CTCGCATCTG AGCCTGCCGA TGACACTGTT AATGGAGAAT CATCCTCATT     180

TGCACCAACT GATAATGCGT CTGTCACGGG TACTCCAGTA GTGTCTGAAG AAAATGCCTT     240

GTCTCCAAAT TGCACTAGTA CTACTGTTGA AGATCCTCCA GTTCAAGAAA TACTGACTTC     300

CTCAGAAAAC AATGAATGTA TTCCTTCTAC CAGTGCAGAA TTGGAATCTG AAGCTAGAAG     360

TATATTAGAG CCTGACACCT CTAATTCTAG AAGTAGTTCT GCTTTTGAAG CAGCCAAATC     420

AAGACAGCCA GATGGGTGTA TGGATCCTGT ACGGCAGCAG TCTGGGAATG CCAACACAGA     480

AACCTTGCCA TCAGGGTGGG AACAAAGAAA AGATCCTCAT GGTAGAACCT ATTATGTGGA     540

TCATAATACT CGAACTACCA CATGGGAGAG ACCACAACCT TTACCTCCAG GTTGGGAAAG     600

AAGAGTTGAT GATCGTAGAA GAGTTTATTA TGTGGATCAT AACACCAGAA CAACAACGTG     660

GCAGCGGCCT ACCATGGAAT CTGTCCGAAA TTTTGAACAG TGGCAATCTC AGCGGAACCA     720

ATTGCAGGGA GCTATGCAAC AGTTTAACCA ACGATACCTC TATTCGGCTT CAATGTTAGC     780

TGCAGAAAAT GACCCTTATG GACCTTTGCC ACCAGGCTGG GAAAAAGAG TGGATTCAAC      840

AGACAGGGTT TACTTTGTGA ATCATAACAC AAAAACAACC CAGTGGGAAG ATCCAAGAAC     900

TCAAGGCTTA CAGAATGAAG AACCCCTGCC AGAAGGCTGG GAAATTAGAT ATACTCGTGA     960

AGGTGTAAGG TACTTTGTTG ATCATAACAC AAGAACAACA ACATTCAAAG ATCCTCGCAA    1020

TGGGAAGTCA TCTGTAACTA AAGGTGGTCC ACAAATTGCT TATGAACGCG GCTTTAGGTG    1080

GAAGCTTGCT CACTTCCGTT ATTTGTGCCA GTCAATGCA CTACCTAGTC ATGTAAAGAT     1140

CAATGTGTCC CGGCAGACAT TGTTTGAAGA TTCCTTCCAA CAGATTATGG CATTAAAACC    1200

CTATGACTTG AGGAGGCGCT ATATGTAAT ATTTAGAGGA GAAGAAGGAC TTGATTATGG     1260

TGGCCTAGCG AGAGAATGGT TTTTCTTGCT TTCACATGAA GTTTTGAACC CAATGTATTG    1320

CTTATTTGAG TATGCGGGCA AGAACAACTA TTGTCTGCAG ATAAATCCAG CATCAACCAT    1380

TAATCCAGAC CATCTTTCAT ACTTCTGTTT CATTGGTCGT TTTATTGCCA TGGCACTATT    1440

TCATGGAAAG TTTATCGATA CTGGTTTCTC TTTACCATTC TACAAGCGTA TGTTAAGTAA    1500
```

-continued

```
AAAACTTACT ATTAAGGATT TGGAATCTAT TGATACTGAA TTTTATAACT CCCTTATCTG    1560

GATAAGAGAT AACAACATTG AAGAATGTGG CTTAGAAATG TACTTTTCTG TTGACATGGA    1620

GATTTTGGGA AAAGTTACTT CACATGACCT GAAGTTGGGA GGTTCCAATA TTCTGGTGAC    1680

TGAGGAGAAC AAAGATGAAT ATATTGGTTT AATGACAGAA TGGCGTTTTT CTCGAGGAGT    1740

ACAAGAACAG ACCAAAGCTT TCCTTGATGG TTTTAATGAA GTTGTTCCTC TTCAGTGGCT    1800

ACAGTACTTC GATGAAAAAG AATTAGAGGT TATGTTGTGT GGCATGCAGG AGGTTGACTT    1860

GGCAGATTGG CAGAGAAATA CTGTTTATCG ACATTATACA AGAAACAGCA AGCAAATCAT    1920

TTGGTTTTGG CAGTTTGTGA AAGAGACAGA CAATGAAGTA AGAATGCGAC TATTGCAGTT    1980

CGTCACTGGA ACCTGCCGTT TACCTCTAGG AGGATTTGCT GAGCTCATGG GAAGTAATGG    2040

GCCCCGGAAT TC                                                       2052
```

(2) INFORMATION FOR SEQ ID NO: 46:

(i) SEQUENCE CHARACTERISTICS:
        (A) LENGTH: 683 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 46:

```
Thr Asn His Val Pro Thr Ser Thr Leu Val Gln Asn Ser Cys Cys Ser
1               5                   10                  15

Tyr Val Val Asn Gly Asp Asn Thr Pro Ser Ser Pro Ser Gln Val Ala
            20                  25                  30

Ala Arg Pro Lys Asn Thr Pro Ala Pro Lys Pro Leu Ala Ser Glu Pro
        35                  40                  45

Ala Asp Asp Thr Val Asn Gly Glu Ser Ser Ser Phe Ala Pro Thr Asp
    50                  55                  60

Asn Ala Ser Val Thr Gly Thr Pro Val Val Ser Glu Glu Asn Ala Leu
65                  70                  75                  80

Ser Pro Asn Cys Thr Ser Thr Thr Val Glu Asp Pro Pro Val Gln Glu
                85                  90                  95

Ile Leu Thr Ser Ser Glu Asn Asn Glu Cys Ile Pro Ser Thr Ser Ala
            100                 105                 110

Glu Leu Glu Ser Glu Ala Arg Ser Ile Leu Glu Pro Asp Thr Ser Asn
        115                 120                 125

Ser Arg Ser Ser Ser Ala Phe Glu Ala Ala Lys Ser Arg Gln Pro Asp
    130                 135                 140

Gly Cys Met Asp Pro Val Arg Gln Gln Ser Gly Asn Ala Asn Thr Glu
145                 150                 155                 160

Thr Leu Pro Ser Gly Trp Glu Gln Arg Lys Asp Pro His Gly Arg Thr
                165                 170                 175

Tyr Tyr Val Asp His Asn Thr Arg Thr Thr Trp Glu Arg Pro Gln
            180                 185                 190

Pro Leu Pro Pro Gly Trp Glu Arg Val Asp Arg Arg Val
        195                 200                 205

Tyr Tyr Val Asp His Asn Thr Arg Thr Thr Trp Gln Arg Pro Thr
    210                 215                 220

Met Glu Ser Val Arg Asn Phe Glu Gln Trp Gln Ser Gln Arg Asn Gln
225                 230                 235                 240

Leu Gln Gly Ala Met Gln Gln Phe Asn Gln Arg Tyr Leu Tyr Ser Ala
```

-continued

```
                245                 250                 255
Ser Met Leu Ala Ala Glu Asn Asp Pro Tyr Gly Pro Leu Pro Pro Gly
                260                 265                 270

Trp Glu Lys Arg Val Asp Ser Thr Asp Arg Val Tyr Phe Val Asn His
            275                 280                 285

Asn Thr Lys Thr Thr Gln Trp Glu Asp Pro Arg Thr Gln Gly Leu Gln
        290                 295                 300

Asn Glu Glu Pro Leu Pro Glu Gly Trp Glu Ile Arg Tyr Thr Arg Glu
305                 310                 315                 320

Gly Val Arg Tyr Phe Val Asp His Asn Thr Arg Thr Thr Thr Phe Lys
                325                 330                 335

Asp Pro Arg Asn Gly Lys Ser Ser Val Thr Lys Gly Pro Gln Ile
                340                 345                 350

Ala Tyr Glu Arg Gly Phe Arg Trp Lys Leu Ala His Phe Arg Tyr Leu
                355                 360                 365

Cys Gln Ser Asn Ala Leu Pro Ser His Val Lys Ile Asn Val Ser Arg
                370                 375                 380

Gln Thr Leu Phe Glu Asp Ser Phe Gln Gln Ile Met Ala Leu Lys Pro
385                 390                 395                 400

Tyr Asp Leu Arg Arg Leu Tyr Val Ile Phe Arg Gly Glu Glu Gly
                405                 410                 415

Leu Asp Tyr Gly Gly Leu Ala Arg Glu Trp Phe Phe Leu Leu Ser His
                420                 425                 430

Glu Val Leu Asn Pro Met Tyr Cys Leu Phe Glu Tyr Ala Gly Lys Asn
                435                 440                 445

Asn Tyr Cys Leu Gln Ile Asn Pro Ala Ser Thr Ile Asn Pro Asp His
            450                 455                 460

Leu Ser Tyr Phe Cys Phe Ile Gly Arg Phe Ile Ala Met Ala Leu Phe
465                 470                 475                 480

His Gly Lys Phe Ile Asp Thr Gly Phe Ser Leu Pro Phe Tyr Lys Arg
                485                 490                 495

Met Leu Ser Lys Lys Leu Thr Ile Lys Asp Leu Glu Ser Ile Asp Thr
                500                 505                 510

Glu Phe Tyr Asn Ser Leu Ile Trp Ile Arg Asp Asn Asn Ile Glu Glu
            515                 520                 525

Cys Gly Leu Glu Met Tyr Phe Ser Val Asp Met Glu Ile Leu Gly Lys
            530                 535                 540

Val Thr Ser His Asp Leu Lys Leu Gly Gly Ser Asn Ile Leu Val Thr
545                 550                 555                 560

Glu Glu Asn Lys Asp Glu Tyr Ile Gly Leu Met Thr Glu Trp Arg Phe
                565                 570                 575

Ser Arg Gly Val Gln Glu Gln Thr Lys Ala Phe Leu Asp Gly Phe Asn
                580                 585                 590

Glu Val Val Pro Leu Gln Trp Leu Gln Tyr Phe Asp Glu Lys Glu Leu
            595                 600                 605

Glu Val Met Leu Cys Gly Met Gln Glu Val Asp Leu Ala Asp Trp Gln
            610                 615                 620

Arg Asn Thr Val Tyr Arg His Tyr Thr Arg Asn Ser Lys Gln Ile Ile
625                 630                 635                 640

Trp Phe Trp Gln Phe Val Lys Glu Thr Asp Asn Glu Val Arg Met Arg
                645                 650                 655

Leu Leu Gln Phe Val Thr Gly Thr Cys Arg Leu Pro Leu Gly Gly Phe
                660                 665                 670
```

Ala Glu Leu Met Gly Ser Asn Gly Pro Arg Asn
    675                 680

(2) INFORMATION FOR SEQ ID NO: 47:

(i) SEQUENCE CHARACTERISTICS:
        (A) LENGTH: 3476 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 47:

| | |
|---|---|
| GAATTCGCGG CCGCGTCCAC CGCTTCTGTG GCCACGGCAG ATGAAACAGA AAGGCTAAAG | 60 |
| AGGGCTGGAG TCAGGGGACT TCTCTTCCAC CAGCTTCACG GTGATGATAT GGCATCTGCC | 120 |
| AGCTCTAGCC GGGCAGGAGT GGCCCTGCCT TTTGAGAAGT CTCAGCTCAC TTTGAAAGTG | 180 |
| GTGTCCGCAA AGCCCAAGGT GCATAATCGT CAACCTCGAA TTAACTCCTA CGTGGAGGTG | 240 |
| GCGGTGGATG GACTCCCCAG TGAGACCAAG AAGACTGGGA AGCGCATTGG GAGCTCTGAG | 300 |
| CTTCTCTGGA ATGAGATCAT CATTTTGAAT GTCACGGCAC AGAGTCATTT AGATTTAAAG | 360 |
| GTCTGGAGCT GCCATACCTT GAGAAATGAA CTGCTAGGCA CCGCATCTGT CAACCTCTCC | 420 |
| AACGTCTTGA AGAACAATGG GGGCAAAATG GAGAACATGC AGCTGACCCT GAACCTGCAG | 480 |
| ACGGAGAACA AAGGCAGCGT TGTCTCAGGC GGAAAACTGA CAATTTTCCT GGACGGGCCA | 540 |
| ACTGTTGATC TGGGAAATGT GCCTAATGGC AGTGCCCTGA CAGATGGATC ACAGCTGCCT | 600 |
| TCGAGAGACT CCAGTGGAAC AGCAGTAGCT CCAGAGAACC GGCACCAGCC CCCCAGCACA | 660 |
| AACTGCTTTG GTGGAAGATC CCGGACGCAC AGACATTCGG GTGCTTCAGC CAGAACAACC | 720 |
| CCAGCAACCG GCGAGCAAAG CCCCGGTGCT CGGAGCCGGC ACCGCCAGCC CGTCAAGAAC | 780 |
| TCAGGCCACA GTGGCTTGGC CAATGGCACA GTGAATGATG AACCCACAAC AGCCACTGAT | 840 |
| CCCGAAGAAC CTTCCGTTGT TGGTGTGACG TCCCCACCTG CTGCACCCTT GAGTGTGACC | 900 |
| CCGAATCCCA ACACGACTTC TCTCCCTGCC CCAGCCACAC CGGCTGAAGG AGAGGAACCC | 960 |
| AGCACTTCGG GTACACAGCA GCTCCCAGCG GCTGCCCAGG CCCCCGACGC TCTGCCTGCT | 1020 |
| GGATGGGAAC AGCGAGAGCT GCCCAACGGA CGTGTCTATT ATGTTGACCA CAATACCAAG | 1080 |
| ACCACCACCT GGGAGCGGCC CCTTCCTCCA GGCTGGGAAA AACGCACAGA TCCCCGAGGC | 1140 |
| AGGTTTTACT ATGTGGATCA CAATACTCGG ACCACCACCT GGCAGCGTCC GACCGCGGAG | 1200 |
| TACGTGCGCA ACTATGAGCA GTGGCAGTCG CAGCGGAATC AGCTCCAGGG GGCCATGCAG | 1260 |
| CACTTCAGCC AAAGATTCCT ATACCAGTTT TGGAGTGCTT CGACTGACCA TGATCCCCTG | 1320 |
| GGCCCCCTCC CTCCTGGTTG GGAGAAAAGA CAGGACAATG GACGGGTGTA TTACGTGAAC | 1380 |
| CATAACACTC GCACGACCCA GTGGGAGGAT CCCCGGACCC AGGGGATGAT CCAGGAACCA | 1440 |
| GCTTTGCCCC CAGGATGGGA GATGAAATAC ACCAGCGAGG GGGTGCGATA CTTTGTGGAC | 1500 |
| CACAATACCC GCACCACCAC CTTTAAGGAT CCTCGCCCGG GGTTTGAGTC GGGGACGAAG | 1560 |
| CAAGGTTCCC CTGGTGCTTA TGACCGCAGT TTTCGGTGGA AGTATCACCA GTTCCGTTTC | 1620 |
| CTCTGCCATT CAAATGCCCT ACCTAGCCAC GTGAAGATCA GCGTTTGCAG GCAGACGCTT | 1680 |
| ACCTAGCCAC GTGAAGATCA GCGTTTCCAG GCAGACGCTT ATGACCTGCG CCGCCGGCTT | 1740 |
| TACATCATCA TGCGTGGCGA GGAGGGCCTG ACTATGGGG GCATCGCCAG AGAGTGGTTT | 1800 |
| TTCCTCCTGT CTCAGGAGGT GCTCAACCCT ATGTATTGTT TATTTGAATA TGCCGGAAAG | 1860 |

-continued

| | |
|---|---|
| AACAATTACT GCCTGCAGAT CAACCCCGCC TCCTCCATCA ACCCGGACCA CCTCACCTAC | 1920 |
| TTTCGCTTTA TAGGCAGATT CATCGCCATG GCGCTGTACC ATGGAAAGTT CATCGACACG | 1980 |
| GGCTTCACCC TCCCTTTCTA CAAGCGGATG CTCAATAAGA GACCAACCCT GAAAGACCTG | 2040 |
| GAGTCCATTG ACCCTGAGTT CTACAACTCC ATTGTCTGGA TCAAAGAGAA CAACCTGGAA | 2100 |
| GAATGTGGCC TGGAGCTGTA CTTCATCCAG GACATGGAGA TACTGGGCAA GGTCACCACC | 2160 |
| CACGAGCTGA AGGAGGGCGG CGAGAGCATC CGGGTCACGG AGGAGAACAA GGAAGAGTAC | 2220 |
| ATCATGCTGC TGACTGACTG GCGTTTCACC CGAGGCGTGG AAGAGCAGAC CAAAGCCTTC | 2280 |
| CTGGATGGCT TCAACGAGGT GGCCCCGCTG GAGTGGCTGC GCTACTTTGA CGAGAAAGAG | 2340 |
| CTGGAGCTGA TGCTGTGCGG CATGCAGGAG ATAGACATGA GCGACTGGCA GAAGAGCACC | 2400 |
| ATCTACCGGC ACTACACCAA GAACAGCAAG CAGATCCAGT GGTTCTGGCA GGTGGTGAAG | 2460 |
| GAGATGGACA ACGAGAAGAG GATCCGGCTG CTGCAGTTTG TCACCGGTAC CTGCCGCCTG | 2520 |
| CCCGTCGGGG GATTTGCCGA ACTCATCGGT AGCAACGGAC CACAGAAGTT TTGCATTGAC | 2580 |
| AAAGTTGGCA AGGAAACCTG GCTGCCCAGA AGCCACACCT GCTTCAACCG TCTGGATCTT | 2640 |
| CCACCCTACA AGAGCTACGA ACAGCTGAGA GAGAAGCTGC TGTATGCCAT TGAGGAGACC | 2700 |
| GAGGGCTTTG ACAGGAGTA ACCGAGGCCG CCCCTCCCAC GCCCCCAGC GCACATGTAG | 2760 |
| TCCTGAGTCC TCCCTGCCTG AGAGGCCACT GGCCCCGCAG CCCTTGGGAG GCCCCCGTGG | 2820 |
| ATGTGGCCCT GTGTGGGACC ACACTGTCAT CTCGCTGCTG GCAGAAAAGC CTGATCCCAG | 2880 |
| GAGGCCCTGC AGTTCCCCCG ACCCGCGGAT GGCAGTCTGG AATAAAGCCC CCTAGTTGCC | 2940 |
| TTTGGCCCCA CCTTTGCAAA GTTCCAGAGG GCTGACCCTC TCTGCAAAAC TCTCCCCTGT | 3000 |
| CCTCTAGACC CCACCCTGGG TGTATGTGAG TGTGCAAGGG AAGGTGTTGC ATCCCCAGGG | 3060 |
| GCTGCCGCAG AGGCCGGAGA CCTCCTGGAC TAGTTCGGCG AGGAGACTGG CCACTGGGGG | 3120 |
| TGGCTGTTCG GGACTGAGAG CGCCAAGGGT CTTTGCCAGC AAAGGAGGTT CTGCCTGTAA | 3180 |
| TTGAGCCTCT CTGATGATGG AGATGAAGTG AAGGTCTGAG GGACGGGCCC TGGGGCTAGG | 3240 |
| CCATCTCTGC CTGCCTCCCT AGCAGGCGCC AGCGGTGGAG GCTGAGTCGC AGGACACATG | 3300 |
| CCGGCCAGTT AATTCATTCT CAGCAAATGA AGGTTTGTCT AAGCTGCCTG GGTATCCACG | 3360 |
| GGACAAAAAC AGCAAACTCC CTCCAGACTT TGTCCATGTT ATAAACTTCA AAGTTGGTTG | 3420 |
| TTGTTTGTTA NGGTTTGCCA GGTTTTTTTG TTTACGCCTG CTGTCACTTT CCTGTC | 3476 |

(2) INFORMATION FOR SEQ ID NO: 48:

(i) SEQUENCE CHARACTERISTICS:
        (A) LENGTH: 906 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 48:

```
Glu Phe Ala Ala Ala Ser Thr Ala Ser Val Ala Thr Ala Asp Glu Thr
 1               5                  10                  15

Glu Arg Leu Lys Arg Ala Gly Val Arg Gly Leu Leu Phe His Gln Leu
                20                  25                  30

His Gly Asp Asp Met Ala Ser Ala Ser Ser Arg Ala Gly Val Ala
            35                  40                  45

Leu Pro Phe Glu Lys Ser Gln Leu Thr Leu Lys Val Val Ser Ala Lys
        50                  55                  60
```

```
Pro Lys Val His Asn Arg Gln Pro Arg Ile Asn Ser Tyr Val Glu Val
 65                  70                  75                  80

Ala Val Asp Gly Leu Pro Ser Glu Thr Lys Thr Gly Lys Arg Ile
             85                  90                  95

Gly Ser Ser Glu Leu Leu Trp Asn Glu Ile Ile Ile Leu Asn Val Thr
                100                 105                 110

Ala Gln Ser His Leu Asp Leu Lys Val Trp Ser Cys His Thr Leu Arg
            115                 120                 125

Asn Glu Leu Leu Gly Thr Ala Ser Val Asn Leu Ser Asn Val Leu Lys
        130                 135                 140

Asn Asn Gly Gly Lys Met Glu Asn Met Gln Leu Thr Leu Asn Leu Gln
145                 150                 155                 160

Thr Glu Asn Lys Gly Ser Val Val Ser Gly Lys Leu Thr Ile Phe
                165                 170                 175

Leu Asp Gly Pro Thr Val Asp Leu Gly Asn Val Pro Asn Gly Ser Ala
            180                 185                 190

Leu Thr Asp Gly Ser Gln Leu Pro Ser Arg Asp Ser Ser Gly Thr Ala
        195                 200                 205

Val Ala Pro Glu Asn Arg His Gln Pro Pro Ser Thr Asn Cys Phe Gly
    210                 215                 220

Gly Arg Ser Arg Thr His Arg His Ser Gly Ala Ser Ala Arg Thr Thr
225                 230                 235                 240

Pro Ala Thr Gly Glu Gln Ser Pro Gly Ala Arg Ser Arg His Arg Gln
                245                 250                 255

Pro Val Lys Asn Ser Gly His Ser Gly Leu Ala Asn Gly Thr Val Asn
            260                 265                 270

Asp Glu Pro Thr Thr Ala Thr Asp Pro Glu Glu Pro Ser Val Val Gly
        275                 280                 285

Val Thr Ser Pro Pro Ala Ala Pro Leu Ser Val Thr Pro Asn Pro Asn
    290                 295                 300

Thr Thr Ser Leu Pro Ala Pro Ala Thr Pro Ala Glu Gly Glu Glu Pro
305                 310                 315                 320

Ser Thr Ser Gly Thr Gln Gln Leu Pro Ala Ala Gln Ala Pro Asp
                325                 330                 335

Ala Leu Pro Ala Gly Trp Glu Gln Arg Glu Leu Pro Asn Gly Arg Val
            340                 345                 350

Tyr Tyr Val Asp His Asn Thr Lys Thr Thr Thr Trp Glu Arg Pro Leu
        355                 360                 365

Pro Pro Gly Trp Glu Lys Arg Thr Asp Pro Arg Gly Arg Phe Tyr Tyr
    370                 375                 380

Val Asp His Asn Thr Arg Thr Thr Thr Trp Gln Arg Pro Thr Ala Glu
385                 390                 395                 400

Tyr Val Arg Asn Tyr Glu Gln Trp Gln Ser Gln Arg Asn Gln Leu Gln
                405                 410                 415

Gly Ala Met Gln His Phe Ser Gln Arg Phe Leu Tyr Gln Phe Trp Ser
            420                 425                 430

Ala Ser Thr Asp His Asp Pro Leu Gly Pro Leu Pro Pro Gly Trp Glu
        435                 440                 445

Lys Arg Gln Asp Asn Gly Arg Val Tyr Tyr Val Asn His Asn Thr Arg
    450                 455                 460

Thr Thr Gln Trp Glu Asp Pro Arg Thr Gln Gly Met Ile Gln Glu Pro
465                 470                 475                 480

Ala Leu Pro Pro Gly Trp Glu Met Lys Tyr Thr Ser Glu Gly Val Arg
```

-continued

```
                485                 490                 495
Tyr Phe Val Asp His Asn Thr Arg Thr Thr Phe Lys Asp Pro Arg
                500                 505                 510
Pro Gly Phe Glu Ser Gly Thr Lys Gln Gly Ser Pro Gly Ala Tyr Asp
                515                 520                 525
Arg Ser Phe Arg Trp Lys Tyr His Gln Phe Arg Phe Leu Cys His Ser
                530                 535                 540
Asn Ala Leu Pro Ser His Val Lys Ile Ser Val Ser Arg Gln Thr Leu
545                 550                 555                 560
Phe Glu Asp Ser Phe Gln Gln Ile Met Asn Met Lys Pro Tyr Asp Leu
                565                 570                 575
Arg Arg Arg Leu Tyr Ile Ile Met Arg Gly Glu Glu Gly Leu Asp Tyr
                580                 585                 590
Gly Gly Ile Ala Arg Glu Trp Phe Phe Leu Leu Ser His Glu Val Leu
                595                 600                 605
Asn Pro Met Tyr Cys Leu Phe Glu Tyr Ala Gly Lys Asn Asn Tyr Cys
                610                 615                 620
Leu Gln Ile Asn Pro Ala Ser Ser Ile Asn Pro Asp His Leu Thr Tyr
625                 630                 635                 640
Phe Arg Phe Ile Gly Arg Phe Ile Ala Met Ala Leu Tyr His Gly Lys
                645                 650                 655
Phe Ile Asp Thr Gly Phe Thr Leu Pro Phe Tyr Lys Arg Met Leu Asn
                660                 665                 670
Lys Arg Pro Thr Leu Lys Asp Leu Glu Ser Ile Asp Pro Glu Phe Tyr
                675                 680                 685
Asn Ser Ile Val Trp Ile Lys Glu Asn Asn Leu Glu Glu Cys Gly Leu
690                 695                 700
Glu Leu Tyr Phe Ile Gln Asp Met Glu Ile Leu Gly Lys Val Thr Thr
705                 710                 715                 720
His Glu Leu Lys Glu Gly Gly Glu Ser Ile Arg Val Thr Glu Glu Asn
                725                 730                 735
Lys Glu Glu Tyr Ile Met Leu Leu Thr Asp Trp Arg Phe Thr Arg Gly
                740                 745                 750
Val Glu Glu Gln Thr Lys Ala Phe Leu Asp Gly Phe Asn Glu Val Ala
                755                 760                 765
Pro Leu Glu Trp Leu Arg Tyr Phe Asp Glu Lys Glu Leu Glu Leu Met
                770                 775                 780
Leu Cys Gly Met Gln Glu Ile Asp Met Ser Asp Trp Gln Lys Ser Thr
785                 790                 795                 800
Ile Tyr Arg His Tyr Thr Lys Asn Ser Lys Gln Ile Gln Trp Phe Trp
                805                 810                 815
Gln Val Val Lys Glu Met Asp Asn Glu Lys Arg Ile Arg Leu Leu Gln
                820                 825                 830
Phe Val Thr Gly Thr Cys Arg Leu Pro Val Gly Gly Phe Ala Glu Leu
                835                 840                 845
Ile Gly Ser Asn Gly Pro Gln Lys Phe Cys Ile Asp Lys Val Gly Lys
                850                 855                 860
Glu Thr Trp Leu Pro Arg Ser His Thr Cys Phe Asn Arg Leu Asp Leu
865                 870                 875                 880
Pro Pro Tyr Lys Ser Tyr Glu Gln Leu Arg Glu Lys Leu Leu Tyr Ala
                885                 890                 895
Ile Glu Glu Thr Glu Gly Phe Gly Gln Glu
                900                 905
```

(2) INFORMATION FOR SEQ ID NO: 49:

(i) SEQUENCE CHARACTERISTICS:
        (A) LENGTH: 673 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 49:

```
GGAGAAGTGC CTGGCGTGGA CTATAACTTT CTGACTGTGA AGGAGTTCTT GGACCTCGAG    60
CAGAGTGGGA CTCTTCTGGA AGTCGGCACC TATGAAGGAA ACTATTATGG GACACCCAAG   120
CCTCCTAGCC AGCCAGTCAG TGGGAAAGTG ATCACGACGG ATGCCTTGCA CAGCCTTCAG   180
TCTGGCTCTA AGCAGTCGAC CCCGAAGCGA ACCAAGTCCT ACAATGATAT GCAAAATGCT   240
GGCATAGTCC ACGCGGAGAA TGAGGAGGAG GATGACGTTC CTGAAATGAA CAGCAGCTTT   300
ACAGCCGATT CTGGTGAACA GAGGAGCAC ACTCTCCAAG AAACAGCATT ACCACCTGTG    360
AATAGTAGCA TCATCGCTGC TCCCATCACG GACCCTTCTC AGAAGTTCCC TCAATACCTA   420
CCTCTTTCTG CAGAGGATAA TTTAGGTCCT CTACCTGAAA ACTGGGAGAT GGCCTATACT   480
GAAAAATGGAG AAGTCTATTT TATAGACCAT AACACGAAAA CAACATCTTG GTTAGACCCT   540
CGGTGCCTAA CAAGCAGCA GAAGCCACTG GAAGAGTGTG AAGATGATGA AGGGGTACAC    600
ACCGAGGAGC TGGACAGTGA ACTAGAACTG CCTGCTGGTT GGGAAAAGAT TGAAGACCCA   660
TCCCCCGGAA TTC                                                      673
```

(2) INFORMATION FOR SEQ ID NO: 50:

(i) SEQUENCE CHARACTERISTICS:
        (A) LENGTH: 224 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 50:

```
Gly Glu Val Pro Gly Val Asp Tyr Asn Phe Leu Thr Val Lys Glu Phe
 1               5                  10                  15

Leu Asp Leu Glu Gln Ser Gly Thr Leu Leu Glu Val Gly Thr Tyr Glu
             20                  25                  30

Gly Asn Tyr Tyr Gly Thr Pro Lys Pro Pro Ser Gln Pro Val Ser Gly
         35                  40                  45

Lys Val Ile Thr Thr Asp Ala Leu His Ser Leu Gln Ser Gly Ser Lys
     50                  55                  60

Gln Ser Thr Pro Lys Arg Thr Lys Ser Tyr Asn Asp Met Gln Asn Ala
65                  70                  75                  80

Gly Ile Val His Ala Glu Asn Glu Glu Glu Asp Asp Val Pro Glu Met
                 85                  90                  95

Asn Ser Ser Phe Thr Ala Asp Ser Gly Glu Gln Glu Glu His Thr Leu
                100                 105                 110

Gln Glu Thr Ala Leu Pro Pro Val Asn Ser Ser Ile Ile Ala Ala Pro
            115                 120                 125

Ile Thr Asp Pro Ser Gln Lys Phe Pro Gln Tyr Leu Pro Leu Ser Ala
        130                 135                 140

Glu Asp Asn Leu Gly Pro Leu Pro Glu Asn Trp Glu Met Ala Tyr Thr
```

```
          145                 150                 155                 160
Glu Asn Gly Glu Val Tyr Phe Ile Asp His Asn Thr Lys Thr Thr Ser
                    165                 170                 175
Trp Leu Asp Pro Arg Cys Leu Asn Lys Gln Gln Lys Pro Leu Glu Glu
                180                 185                 190
Cys Glu Asp Asp Glu Gly Val His Thr Glu Glu Leu Asp Ser Glu Leu
            195                 200                 205
Glu Leu Pro Ala Gly Trp Glu Lys Ile Glu Asp Pro Ser Pro Gly Ile
        210                 215                 220
```

(2) INFORMATION FOR SEQ ID NO: 51:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 51:

```
Ser Ser Ile Asp Met Pro
1               5
```

(2) INFORMATION FOR SEQ ID NO: 52:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 52:

```
Pro Gly Thr Pro Tyr Pro Pro Pro Glu Phe Tyr
1               5                   10
```

(2) INFORMATION FOR SEQ ID NO: 53:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 53:

```
Pro Gly Thr Ala Pro Pro Pro Tyr Thr Val Gly Pro Gly Tyr
1               5                   10
```

(2) INFORMATION FOR SEQ ID NO: 54:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 54:

```
Pro Gly Thr Pro Pro Ala Tyr Thr Val Gly Pro Gly Tyr
1               5                   10
```

(2) INFORMATION FOR SEQ ID NO: 55:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 55:

```
Pro Gly Thr Pro Pro Pro Pro Tyr Thr Val Gly Pro Gly Tyr
1               5                   10                  15
```

(2) INFORMATION FOR SEQ ID NO: 56:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 56:

```
Glu Tyr Pro Pro Tyr Pro Pro Pro Tyr Pro Ser Gly Glu
1               5                   10
```

(2) INFORMATION FOR SEQ ID NO: 57:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 57:

```
Ser Lys Thr Thr Ser Pro Pro Pro Tyr Ser Leu Gly Pro Leu Lys
1               5                   10                  15
```

(2) INFORMATION FOR SEQ ID NO: 58:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 58:

```
His Ser Pro Pro Leu Pro Pro Tyr Thr Pro Pro Thr Leu
1               5                   10
```

(2) INFORMATION FOR SEQ ID NO: 59:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 59:

```
Pro Gly Thr Pro Pro Pro Asn Tyr Asp Ser Leu Arg Leu
1               5                   10
```

(2) INFORMATION FOR SEQ ID NO: 60:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 60:

```
Pro Gly Thr Pro Pro Lys Tyr Asn Thr Leu Arg Leu
1               5                   10
```

(2) INFORMATION FOR SEQ ID NO: 61:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 61:

```
Pro Pro Pro Ala Leu Pro Pro Pro Arg Pro Val Ala Asp Lys
1               5                   10                  15
```

(2) INFORMATION FOR SEQ ID NO: 62:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 62:

```
Gly Ile Leu Ala Pro Pro Val Pro Pro Arg Asn Thr Arg
1               5                   10
```

(2) INFORMATION FOR SEQ ID NO: 63:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 63:

```
Ser Val Pro Ala Pro Pro Leu Pro Pro Lys Ser Gly Gly
1               5                   10
```

(2) INFORMATION FOR SEQ ID NO: 64:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 64:

```
Ser Leu Gln Trp Met Asp Gly Val Gly Trp Tyr Met Glu
1               5                   10
```

(2) INFORMATION FOR SEQ ID NO: 65:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 65:

Arg Trp Ala Trp Asp Asp Gly Trp Met Phe Gly Ser Val
1               5                   10

(2) INFORMATION FOR SEQ ID NO: 66:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 66:

Ser Gly Leu Glu Gly Trp Tyr Trp Glu Arg Gly Trp Val
1               5                   10

(2) INFORMATION FOR SEQ ID NO: 67:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 67:

Ser Ile Trp Glu Met Gly Xaa Asp Trp Trp Ala Arg Pro
1               5                   10

(2) INFORMATION FOR SEQ ID NO: 68:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 68:

Arg Met Ser Trp Trp Glu Glu Trp Glu Phe Gly Leu Gly
1               5                   10

(2) INFORMATION FOR SEQ ID NO: 69:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 69:

Ser Trp Gly Leu Asp Gly Trp Leu Val Asp Gly Trp Ser (2) INFORMATION FOR SEQ ID NO: 70:

(i) SEQUENCE CHARACTERISTICS:
        (A) LENGTH: 53 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 70:

```
Phe Asn Asp Glu Ser Ser Glu Gly Pro Asp Lys Leu Lys Phe Lys Arg
 1               5                  10                  15
Trp Phe Trp Ser Ile Val Glu Lys Met Asn Ile Met Glu Arg Gln His
            20                  25                  30
Leu Val Tyr Phe Trp Thr Gly Ser Pro Ala Leu Pro Ala Ser Glu Glu
        35                  40                  45
Gly Phe Gln Pro Leu
    50
```

(2) INFORMATION FOR SEQ ID NO: 71:

(i) SEQUENCE CHARACTERISTICS:
        (A) LENGTH: 52 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 71:

```
Tyr Lys Asn Gly Tyr Ser Met Asn His Gln Val Ile His Asp Phe Ile
 1               5                  10                  15
Ser Ile Ile Ser Ala Phe Gly Lys His Glu Arg Arg Leu Phe Leu Gln
            20                  25                  30
Phe Leu Thr Gly Ser Pro Arg Leu Pro Ile Gly Gly Phe Lys Ser Leu
        35                  40                  45
Asn Pro Lys Phe
    50
```

(2) INFORMATION FOR SEQ ID NO: 72:

(i) SEQUENCE CHARACTERISTICS:
        (A) LENGTH: 48 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 72:

```
Tyr Val Gly Gly Phe Ser Asp Asp Ser Arg Ala Val Cys Trp Phe Trp
 1               5                  10                  15
Glu Ile Ile Glu Ser Trp Asp Tyr Pro Leu Gln Arg Lys Leu Leu Gln
            20                  25                  30
Phe Val Thr Ala Ser Asp Arg Ile Pro Ala Thr Gly Ile Ser Thr Ile
        35                  40                  45
```

(2) INFORMATION FOR SEQ ID NO: 73:

(i) SEQUENCE CHARACTERISTICS:
        (A) LENGTH: 51 amino acids

```
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 73:

Tyr His Lys Tyr Gln Ser Asn Ser Ile Gln Ile Gln Trp Phe Trp Arg
1               5                   10                  15

Ala Leu Arg Ser Phe Asp Gln Ala Asp Arg Ala Lys Phe Leu Gln Phe
            20                  25                  30

Val Thr Gly Thr Ser Arg Val Pro Leu Gln Gly Phe Ala Ala Leu Glu
        35                  40                  45

Gly Met Asn
    50

(2) INFORMATION FOR SEQ ID NO: 74:

(i) SEQUENCE CHARACTERISTICS:
            (A) LENGTH: 54 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 74:

Gly Pro Arg Arg Phe Thr Ile Glu Lys Ala Gly Glu Val Gln Gln Leu
1               5                   10                  15

Pro Lys Ser His Thr Cys Phe Asn Arg Val Asp Leu Pro Gln Tyr Val
            20                  25                  30

Asp Tyr Asp Ser Met Arg Gln Arg Leu Thr Leu Ala Val Glu Glu Thr
        35                  40                  45

Ile Gly Phe Gly Gln Glu
    50

(2) INFORMATION FOR SEQ ID NO: 75:

(i) SEQUENCE CHARACTERISTICS:
            (A) LENGTH: 55 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 75:

Gly Pro Gln Ser Phe Thr Val Glu Gln Trp Gly Thr Pro Asp Arg Leu
1               5                   10                  15

Pro Arg Ala His Thr Cys Phe Asn Arg Leu Asp Leu Pro Pro Tyr Glu
            20                  25                  30

Ser Phe Asp Glu Leu Trp Asp Arg Leu Gln Met Ala Ile Glu Asn Thr
        35                  40                  45

Gln Gly Phe Asp His Val Asp
    50              55

(2) INFORMATION FOR SEQ ID NO: 76:

(i) SEQUENCE CHARACTERISTICS:
            (A) LENGTH: 52 amino acids
            (B) TYPE: amino acid
            (C) STRANDEDNESS: <Unknown>
            (D) TOPOLOGY: unknown
```

(ii) MOLECULE TYPE: peptide (xi) SEQUENCE DESCRIPTION: SEQ ID NO: 76:

Lys Met Ile Ile Ala Lys Asn Gly Pro Asp Thr Glu Arg Leu Pro Thr
1               5                   10                  15

Ser His Thr Cys Phe Asn Val Leu Leu Pro Glu Tyr Ser Ser Lys
            20                  25                  30

Glu Lys Leu Arg Glu Arg Leu Lys Ala Ile Thr Tyr Ala Arg Gly
        35                  40                  45

Phe Gly Met Leu
    50

(2) INFORMATION FOR SEQ ID NO: 77:

(i) SEQUENCE CHARACTERISTICS:
        (A) LENGTH: 50 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 77:

Pro Ser Ile Thr Ile Arg Pro Pro Asp Asp Gln His Leu Pro Thr Ala
1               5                   10                  15

Asn Thr Cys Ile Ser Arg Leu Tyr Val Pro Leu Tyr Ser Ser Arg Gln
            20                  25                  30

Ile Leu Arg Gln Arg Leu Leu Leu Ala Ile Lys Thr Arg Asn Phe Gly
        35                  40                  45

Phe Val
    50

(2) INFORMATION FOR SEQ ID NO: 78:

(i) SEQUENCE CHARACTERISTICS:
        (A) LENGTH: 52 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 78:

Ala Phe Cys Ile His Asn Gly Gly Ser Asp Leu Glu Arg Leu Pro Thr
1               5                   10                  15

Ala Ser Thr Cys Met Asn Leu Leu Lys Leu Pro Glu Phe Tyr Asp Glu
            20                  25                  30

Thr Leu Leu Arg Ser Arg Leu Leu Tyr Ala Ile Glu Cys Ala Ala Gly
        35                  40                  45

Phe Glu Leu Ser
    50

(2) INFORMATION FOR SEQ ID NO: 79:

(i) SEQUENCE CHARACTERISTICS:
        (A) LENGTH: 53 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 79:

-continued

```
Pro Ser Ile Thr Ile Gln Ser Thr Ala Ser Gly Glu Glu Tyr Leu Pro
1               5                   10                  15

Val Ala His Thr Cys Tyr Asn Leu Leu Asp Leu Pro Lys Tyr Ser Ser
                20                  25                  30

Arg Glu Ile Leu Ser Ala Arg Leu Thr Gln Ala Leu Asp Asn Tyr Glu
            35                  40                  45

Gly Phe Ser Leu Ala
    50
```

(2) INFORMATION FOR SEQ ID NO: 80:

(i) SEQUENCE CHARACTERISTICS:
        (A) LENGTH: 53 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 80:

```
Gln Ile Val Ile Glu Ser Thr Glu Asn Pro Asp Asp Phe Leu Pro Ser
1               5                   10                  15

Val Met Thr Cys Val Asn Tyr Leu Lys Leu Pro Asp Tyr Ser Ser Ile
                20                  25                  30

Glu Ile Met Arg Glu Arg Leu Leu Ile Ala Ala Arg Glu Gly Gln Gln
            35                  40                  45

Ser Phe His Leu His
    50
```

(2) INFORMATION FOR SEQ ID NO: 81:

(i) SEQUENCE CHARACTERISTICS:
        (A) LENGTH: 52 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 81:

```
Pro Ser Val Thr Ile Arg Pro Ala Asp Asp Ser His Leu Pro Thr Ala
1               5                   10                  15

Asn Thr Cys Ile Ser Arg Leu Tyr Ile Pro Leu Tyr Ser Ser Arg Ser
                20                  25                  30

Ile Leu Arg Ser Lys Asn Leu Met Ala Ile Lys Xaa Xaa Ser Arg Asn
            35                  40                  45

Phe Gly Phe Val
    50
```

(2) INFORMATION FOR SEQ ID NO: 82:

(i) SEQUENCE CHARACTERISTICS:
        (A) LENGTH: 56 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 82:

```
Thr Ile Val Arg Lys Thr Phe Glu Asp Gly Leu Thr Ala Asp Glu Tyr
1               5                   10                  15

Leu Pro Ser Val Met Thr Cys Ala Asn Tyr Leu Lys Leu Pro Lys Tyr
```

```
                    20                  25                  30
Thr Ser Arg Asp Ile Met Arg Ser Arg Leu Cys Gln Ala Ile Glu Glu
            35                  40                  45
Gly Ala Gly Ala Phe Leu Leu Ser
    50                  55
```

(2) INFORMATION FOR SEQ ID NO: 83:

(i) SEQUENCE CHARACTERISTICS:
        (A) LENGTH: 53 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 83:

```
Pro Phe Lys Ile Ser Leu Leu Gly Ser His Asp Ser Asp Leu Pro
1               5                   10                  15

Leu Ala His Thr Cys Phe Asn Glu Ile Cys Leu Trp Asn Tyr Ser Ser
            20                  25                  30

Arg Lys Arg Leu Glu Leu Arg Leu Leu Trp Ala Ile Asn Glu Ser Glu
            35                  40                  45

Gly Tyr Gly Phe Arg
    50
```

(2) INFORMATION FOR SEQ ID NO: 84:

(i) SEQUENCE CHARACTERISTICS:
        (A) LENGTH: 58 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 84:

```
Gly Ile Gln Lys Phe Gln Ile His Arg Asp Asp Arg Ser Thr Asp Arg
1               5                   10                  15

Leu Pro Ser Ala His Thr Cys Phe Asn Gln Leu Asp Leu Pro Ala Tyr
            20                  25                  30

Glu Ser Phe Glu Lys Leu Arg His Met Leu Leu Leu Ala Ile Gln Glu
            35                  40                  45

Cys Ser Glu Gly Phe Gly Leu Ala Asn Lys
    50                  55
```

(2) INFORMATION FOR SEQ ID NO: 85:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 85:

```
Pro Gly Thr Pro Pro Pro Pro Tyr Thr Val Gly Pro Gly Tyr
1               5                   10
```

(2) INFORMATION FOR SEQ ID NO: 86:

(i) SEQUENCE CHARACTERISTICS:
        (A) LENGTH: 13 amino acids

```
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 86:

His Gly Pro Thr Pro Pro Pro Tyr Thr Val Gly Pro
1               5                   10

(2) INFORMATION FOR SEQ ID NO: 87:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 87:

Tyr Val Gln Pro Pro Pro Pro Tyr Pro Gly Pro Met
1               5                   10

(2) INFORMATION FOR SEQ ID NO: 88:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 88:

Pro Gly Tyr Pro Tyr Pro Pro Pro Pro Glu Phe Tyr
1               5                   10

(2) INFORMATION FOR SEQ ID NO: 89:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 89:

Pro Gly Thr Pro Ala Pro Pro Tyr Thr Val Gly Pro Gly Tyr
1               5                   10

(2) INFORMATION FOR SEQ ID NO: 90:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 90:

Pro Gly Thr Pro Pro Ala Pro Tyr Thr Val Gly Pro Gly Tyr
1               5                   10

(2) INFORMATION FOR SEQ ID NO: 91:

(i) SEQUENCE CHARACTERISTICS:
```

```
            (A) LENGTH: 15 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 91:

Asp Ser Gly Val Arg Pro Leu Pro Pro Leu Pro Asp Pro Gly Val
1               5                  10                  15

(2) INFORMATION FOR SEQ ID NO: 92:

(i) SEQUENCE CHARACTERISTICS:
            (A) LENGTH: 22 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 92:

Val Arg Pro Leu Pro Pro Leu Pro Glu Glu Leu Pro Arg Pro Arg Arg
1               5                  10                  15

Arg Pro Pro Pro Glu Asp
            20

(2) INFORMATION FOR SEQ ID NO: 93:

(i) SEQUENCE CHARACTERISTICS:
            (A) LENGTH: 15 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 93:

Pro Pro Pro Ala Leu Pro Pro Pro Arg Pro Val Ala Asp Lys
1               5                  10                  15

(2) INFORMATION FOR SEQ ID NO: 94:

(i) SEQUENCE CHARACTERISTICS:
            (A) LENGTH: 15 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 94:

Ala Pro Ala Pro Pro Pro Gly Pro Pro Arg Pro Ala Ala Ala Ala
1               5                  10                  15

(2) INFORMATION FOR SEQ ID NO: 95:

(i) SEQUENCE CHARACTERISTICS:
            (A) LENGTH: 17 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 95:

Gly Gly Gly Phe Pro Pro Leu Pro Pro Pro Pro Tyr Leu Pro Pro Leu
1               5                  10                  15
```

Gly (2) INFORMATION FOR SEQ ID NO: 96:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 96:

```
Ser Ile Ser Pro Arg Pro Arg Pro Pro Gly Arg Pro Val Ser Gly
1               5                   10                  15
```

(2) INFORMATION FOR SEQ ID NO: 97:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 97:

```
Pro Pro Pro Glu His Ile Pro Pro Pro Arg Pro Lys Arg Ile Leu
1               5                   10                  15
Glu
```

(2) INFORMATION FOR SEQ ID NO: 98:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 98:

```
Lys Glu Gly Glu Arg Ala Leu Pro Ser Ile Pro Lys Leu Ala Asn
1               5                   10                  15
```

(2) INFORMATION FOR SEQ ID NO: 99:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 99:

```
Ser Arg Leu Lys Pro Ala Pro Pro Pro Pro Ala Ala Ser Ala Gly
1               5                   10                  15
```

(2) INFORMATION FOR SEQ ID NO: 100:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 100:

Gln Ala Ser Leu Pro Pro Val Pro Pro Arg Asp Leu Leu Leu Pro
1               5                   10                  15

(2) INFORMATION FOR SEQ ID NO: 101:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 101:

Pro Val Pro Pro Thr Leu Arg Asp Leu Pro Pro Pro Pro Pro Asp
1               5                   10                  15

Arg Pro Tyr Ser
            20

(2) INFORMATION FOR SEQ ID NO: 102:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 102:

Ser Asp Gln Gly Arg Asn Leu Pro Gly Thr Pro Val Pro Ala Ser
1               5                   10                  15

(2) INFORMATION FOR SEQ ID NO: 103:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 103:

Arg His Ser Arg Arg Gln Leu Pro Pro Val Pro Pro Lys Pro Arg Pro
1               5                   10                  15

Leu Leu (2) INFORMATION FOR SEQ ID NO: 104:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 104:

Glu Lys Val Gly Phe Pro Val Thr Pro Gln Val Pro Leu Arg Pro Met
1               5                   10                  15

Thr Tyr (2) INFORMATION FOR SEQ ID NO: 105:

```
    (i) SEQUENCE CHARACTERISTICS:
        (A) LENGTH: 15 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 105:

Pro Gln Pro His Arg Val Leu Pro Thr Ser Pro Ser Asp Ile Ala
1               5                   10                  15

(2) INFORMATION FOR SEQ ID NO: 106:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 106:

Ala Asp Phe Gln Pro Pro Tyr Phe Pro Pro Pro Tyr Gln Pro Ile Tyr
1               5                   10                  15

Pro Gln Ser (2) INFORMATION FOR SEQ ID NO: 107:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 107:

Ser Ser Ala Ala Pro Pro Pro Pro Pro Arg Arg Ala Thr Pro Glu Lys
1               5                   10                  15

(2) INFORMATION FOR SEQ ID NO: 108:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 108:

Ser Lys Lys Gly Val Met Thr Ala Pro Pro Pro Pro Pro Pro Val
1               5                   10                  15

Tyr Glu Pro Gly Gly
            20

(2) INFORMATION FOR SEQ ID NO: 109:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 109:
```

-continued

Glu Ala Phe Gln Pro Gln Glu Pro Asp Phe Pro Pro Pro Pro Asp
1               5                   10                  15

Leu Glu (2) INFORMATION FOR SEQ ID NO: 110:

(i) SEQUENCE CHARACTERISTICS:
        (A) LENGTH: 24 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 110:

Asp Glu Leu Ala Pro Pro Leu Pro Pro Leu Pro Glu Gly Glu Val Pro
1               5                   10                  15

Pro Pro Arg Pro Pro Pro Pro Glu
            20

(2) INFORMATION FOR SEQ ID NO: 111:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 111:

Pro Gln Arg Arg Ala Pro Ala Val Pro Pro Ala Arg Pro Gly Ser Arg
1               5                   10                  15

(2) INFORMATION FOR SEQ ID NO: 112:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 112:

Leu Gly Gly Ala Pro Pro Val Pro Ser Arg Pro Gly Ala Ser Pro Asp
1               5                   10                  15

Gly (2) INFORMATION FOR SEQ ID NO: 113:

(i) SEQUENCE CHARACTERISTICS:
        (A) LENGTH: 62 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO: 113:

GGCTCGAGNN NSNNSNNSNN SNNSNNSNNS NNSNNSNNSN NSNNSTCTAG AAGGATCGGG      60

CC                                                                    62

(2) INFORMATION FOR SEQ ID NO: 114:

(i) SEQUENCE CHARACTERISTICS:

(A) LENGTH: 17 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO: 114:

GGCCCGATCC TTCTAGA                                                    17

(2) INFORMATION FOR SEQ ID NO: 115:

(i) SEQUENCE CHARACTERISTICS:
        (A) LENGTH: 51 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 115:

Tyr Arg His Tyr Thr Arg Asn Ser Lys Gln Ile Ile Trp Phe Trp Gln
1               5                   10                  15

Phe Val Lys Glu Thr Asp Asn Glu Val Arg Met Arg Leu Leu Gln Phe
            20                  25                  30

Val Thr Gly Thr Cys Arg Leu Pro Leu Gly Gly Phe Ala Glu Leu Met
        35                  40                  45

Gly Ser Asn
        50

(2) INFORMATION FOR SEQ ID NO: 116:

(i) SEQUENCE CHARACTERISTICS:
        (A) LENGTH: 51 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 116:

Tyr Arg His Tyr Thr Lys Asn Ser Lys Gln Ile Gln Trp Phe Trp Gln
1               5                   10                  15

Val Val Lys Glu Met Asp Asn Glu Lys Arg Ile Arg Leu Leu Gln Phe
            20                  25                  30

Val Thr Gly Thr Cys Arg Leu Pro Val Gly Gly Phe Ala Glu Leu Ile
        35                  40                  45

Gly Ser Asn
        50

(2) INFORMATION FOR SEQ ID NO: 117:

(i) SEQUENCE CHARACTERISTICS:
        (A) LENGTH: 51 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 117:

Tyr Arg Gly Tyr Gln Glu Ser Asp Glu Val Ile Gln Trp Phe Trp Lys
1               5                   10                  15

Cys Val Ser Glu Trp Asp Asn Glu Gln Arg Ala Arg Leu Leu Gln Phe
            20                  25                  30

Thr Thr Gly Thr Ser Arg Ile Pro Val Asn Gly Phe Lys Asp Leu Gln
        35                  40                  45

Gly Ser Asp
    50

(2) INFORMATION FOR SEQ ID NO: 118:

(i) SEQUENCE CHARACTERISTICS:
        (A) LENGTH: 54 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 118:

Phe Asn Asp Glu Ser Gly Glu Asn Ala Glu Lys Leu Leu Ile His Trp
1               5                   10                  15

Phe Trp Lys Ala Val Trp Met Met Asp Ser Glu Lys Arg Ile Arg Leu
                20                  25                  30

Leu Gln Phe Val Thr Gly Thr Ser Arg Val Pro Met Asn Gly Phe Ala
            35                  40                  45

Glu Leu Tyr Gly Ser Asn
    50

(2) INFORMATION FOR SEQ ID NO: 119:

(i) SEQUENCE CHARACTERISTICS:
        (A) LENGTH: 48 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 119:

Tyr Asp Gly Gly Tyr Thr Arg Asp Ser Val Leu Ile Arg Glu Phe Trp
1               5                   10                  15

Glu Ile Val His Ser Phe Thr Asp Glu Gln Arg Arg Leu Phe Leu Gln
                20                  25                  30

Phe Thr Thr Gly Thr Asp Arg Ala Pro Val Gly Gly Leu Gly Arg Leu
            35                  40                  45

NFORMATION FOR SEQ ID NO: 120:

(i) SEQUENCE CHARACTERISTICS:
        (A) LENGTH: 52 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 120:

Tyr Lys Gly Asp Tyr Ser Ala Thr His Pro Thr Gln Phe Lys Arg Trp
1               5                   10                  15

Phe Trp Ser Ile Val Glu Arg Met Ser Met Thr Glu Arg Gln Asp Leu
                20                  25                  30

Val Tyr Phe Trp Thr Ser Ser Pro Ser Leu Pro Ala Ser Glu Glu Gly
            35                  40                  45

Phe Gln Pro Met
    50

(2) INFORMATION FOR SEQ ID NO: 121:

(i) SEQUENCE CHARACTERISTICS:
        (A) LENGTH: 50 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 121:

```
Tyr Ser Gly Gly Tyr Ser Ala Asp His Pro Val Ile Arg Val Phe Trp
 1               5                  10                  15

Arg Val Val Glu Gly Phe Thr Asp Glu Glu Lys Arg Lys Leu Leu Lys
                20                  25                  30

Phe Val Thr Ser Cys Ser Arg Pro Pro Leu Leu Gly Phe Lys Glu Leu
                35                  40                  45

Tyr Pro
     50
```

(2) INFORMATION FOR SEQ ID NO: 122:

(i) SEQUENCE CHARACTERISTICS:
        (A) LENGTH: 50 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 122:

```
Pro Asp His Gly Tyr Thr His Asp Ser Arg Ala Val Lys Val Arg Leu
 1               5                  10                  15

Phe Trp Glu Thr Phe His Glu Phe Pro Leu Glu Lys Lys Arg Lys Phe
                20                  25                  30

Leu Leu Phe Leu Thr Gly Ser Asp Arg Ile Pro Ile Tyr Gly Met Ala
                35                  40                  45

Ser Leu
     50
```

(2) INFORMATION FOR SEQ ID NO: 123:

(i) SEQUENCE CHARACTERISTICS:
        (A) LENGTH: 50 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 123:

```
Ala Glu His Gly Tyr Thr Met Asp Ser Ser Ile Phe Leu Phe Glu Ile
 1               5                  10                  15

Leu Ser Ser Phe Asp Asn Glu Gln Gln Arg Leu Phe Leu Gln Phe Val
                20                  25                  30

Thr Gly Ser Pro Arg Leu Pro Val Gly Gly Phe Arg Ser Leu Asn Pro
                35                  40                  45

Pro Leu
     50
```

(2) INFORMATION FOR SEQ ID NO: 124:

(i) SEQUENCE CHARACTERISTICS:

(A) LENGTH: 54 amino acids
(B) TYPE: amino acid
(C) STRANDEDNESS: <Unknown>
(D) TOPOLOGY: unknown (ii) MOLECULE TYPE: peptide (xi) SEQUENCE DESCRIPTION: SEQ ID NO: 124:

Gly Pro Gln Lys Phe Cys Ile Asp Lys Val Gly Lys Glu Thr Trp Leu
1               5                   10                  15
Pro Arg Ser His Thr Cys Phe Asn Arg Leu Asp Leu Pro Pro Tyr Lys
                20                  25                  30
Ser Tyr Glu Gln Leu Arg Glu Lys Leu Leu Tyr Ala Ile Glu Glu Thr
            35                  40                  45
Glu Gly Phe Gly Gln Glu
        50

(2) INFORMATION FOR SEQ ID NO: 125:

(i) SEQUENCE CHARACTERISTICS:
(A) LENGTH: 2232 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO: 125:

| | | | | |
|---|---|---|---|---|
| TCGGCGGATT | CGTCGACCCA | CGCGTCCGGC | CCGAGCCCTC | GGAGGGCGGG GATGTCCCCG | 60 |
| AGCCTTGGGA | GACCATTTCA | GAGGAAGTGA | ATATCGCTGG | AGACTCTCTC GGTCTGGCTC | 120 |
| TGCCCCCACC | ACCGGCCTCC | CCAGGATCTC | GGACCAGCCC | TCAGGAGCTG TCAGAGGAAC | 180 |
| TAAGCAGAAG | GCTTCAGATC | ACTCCAGACT | CCAATGGGGA | ACAGTTCAGC TCTTTGATTC | 240 |
| AAAGAGAACC | CTCCTCAAGG | TTGAGGTCAT | GCAGTGTCAC | CGACGCAGTT GCAGAACAGG | 300 |
| GCCATCTACC | ACCGCCCAGT | GCCCCAGCTG | GGAGAGCGCG | TTCATCAACT GTCACGGGTG | 360 |
| GTGAGGAACC | AACGCCATCA | GTGGCCTATG | TACATACCAC | GCCGGGTCTG CCTTCAGGCT | 420 |
| GGGAAGAAAG | AAAAGATGCT | AAGGGGCGCA | CATACTATGT | CAATCATAAC AATCGAACCA | 480 |
| CAACTTGGAC | TCGACCTATC | ATGCAGCTTG | CAGAAGATGG | TGCGTCCGGA TCAGCCACAA | 540 |
| ACAGTAACAA | CCATCTAATC | GAGCCTCAGA | TCCGCCGGCC | TCGTAGCCTC AGCTCGCCAA | 600 |
| CAGTAACTTT | ATCTGCCCCG | CTGGAGGGTG | CCAAGGACTC | ACCCGTACGT CGGGCTGTGA | 660 |
| AAGACACCCT | TTCCAACCCA | CAGTCCCCAC | AGCCATCACC | TTACAACTCC CCCAAACCAC | 720 |
| AACACAAAGT | CACACAGAGC | TTCTTGCCAC | CCGGCTGGGA | AATGAGGATA GCGCCAAACG | 780 |
| GCCGGCCCTT | CTTCATTGAT | CATAACACAA | AGACTACAAC | CTGGGAAGAT CCACGTTTGA | 840 |
| AATTTCCAGT | ACATATGCGG | TCAAAGACAT | CTTTAAACCC | CAATGACCTT GGCCCCCTTC | 900 |
| CTCCTGGCTG | GGAAGAAAGA | ATTCACTTGG | ATGGCCGAAC | GTTTTATATT GATCATAATA | 960 |
| GCAAAATTAC | TCAGTGGGAA | GACCCAAGAC | TGCAGAACCC | AGCTATTACT GGTCCGGCTG | 1020 |
| TCCCTTACTC | CAGAGAATTT | AAGCAGAAAT | ATGACTACTT | CAGGAAGAAA TTAAAGAAAC | 1080 |
| CTGCTGATAT | CCCCAATAGG | TTTGAAATGA | AACTTCACAG | AAATAACATA TTTGAAGAGT | 1140 |
| CCTATCGGAG | AATTATGTCC | GTGAAAAGAC | CAGATGTCCT | AAAAGCTAGA CTGTGGATTG | 1200 |
| AGTTTGAATC | AGAGAAAGGT | CTTGACTATG | GGGGTGTGGC | CAGAGAATGG TTCTTCTTAC | 1260 |
| TGTCCAAAGA | GATGTTCAAC | CCCTACTACG | GCCTCTTTGA | GTACTCTGCC ACGGACAACT | 1320 |
| ACACCCTTCA | GATCAACCCT | AATTCAGGCC | TCTGTAATGA | GGATCATTTG TCCTACTTCA | 1380 |

-continued

```
CTTTTATTGG AAAAGTTGCT GGTCTGGCCG TATTTCATGG GAAGCTCTTA GATGGTTTCT    1440

TCATTAGACC ATTTTACAAG ATGATGTTGG GAAAGCAGAT AACCCTGAAT GACATGGAAT    1500

CTGTGGATAG TGAATATTAC AACTCTTTGA AATGGATCCT GGAGAATGAC CCTACTGAGC    1560

TGGACCTCAT GTTCTGCATA GACGAAGAAA ACTTTGGACA GACATATCAA GTGGATTTGA    1620

AGCCCAATGG GTCAGAAATA ATGGTCACAA ATGAAAACAA AAGGGAATAT ATCGACTTAG    1680

TCATCCAGTG GAGATTTGTG AACAGGGTCC AGAAGCAGAT GAACGCCTTC TTGGAGGGAT    1740

TCACAGAACT ACTTCCTATT GATTTGATTA AAATTTTTGA TGAAAATGAG CTGGAGTTGC    1800

TCATGTGCGG CCTCGGTGAT GTGGATGTGA ATGACTGGAG ACAGCATTCT ATTTACAAGA    1860

ACGGCTACTG CCCAAACCAC CCCGTCATTC AGTGGTTCTG GAAGGCTGTG CTACTCATGG    1920

ACGCCGAAAA GCGTATCCGG TTACTGCAGT TTGTCACAGG GACATCGCGA GTACCTATGA    1980

ATGGATTTGC CGAACTTTAT GGTTCCAATG GTCCTCAGCT GTTTACAATA GAGCAATGGG    2040

GCAGTCCTGA GAAACTGCCC AAAGCTCACA CATGCTTTAA TCGCCTTGAC TTACCTCCAT    2100

ATGAAACCTT TGAAGATTTA CAAGAGAAAC TTCTCATGGC CGTGGAAAAT GCTCAAGGAT    2160

TTGAAGGGGT GGATTAAGCA CCCTGTGCCT CGGGGGTGGT TGTTCTTCAA GCAATTTCTG    2220

CTTGCACTTT TG                                                        2232
```

(2) INFORMATION FOR SEQ ID NO: 126:

(i) SEQUENCE CHARACTERISTICS:
        (A) LENGTH: 725 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 126:

```
Ser Ala Glu Phe Val Asp Pro Arg Val Arg Pro Glu Pro Ser Glu Gly
1               5                   10                  15

Gly Asp Val Pro Glu Pro Trp Glu Thr Ile Ser Glu Glu Val Asn Ile
            20                  25                  30

Ala Gly Asp Ser Leu Gly Leu Ala Leu Pro Pro Pro Ala Ser Pro
        35                  40                  45

Gly Ser Arg Thr Ser Pro Gln Glu Leu Ser Glu Glu Leu Ser Arg Arg
    50                  55                  60

Leu Gln Ile Thr Pro Asp Ser Asn Gly Glu Gln Phe Ser Ser Leu Ile
65                  70                  75                  80

Gln Arg Glu Pro Ser Ser Arg Leu Arg Ser Cys Ser Val Thr Asp Ala
                85                  90                  95

Val Ala Glu Gln Gly His Leu Pro Pro Pro Ser Ala Pro Ala Gly Arg
            100                 105                 110

Ala Arg Ser Ser Thr Val Thr Gly Gly Glu Glu Pro Thr Pro Ser Val
        115                 120                 125

Ala Tyr Val His Thr Thr Pro Gly Leu Pro Ser Gly Trp Glu Glu Arg
    130                 135                 140

Lys Asp Ala Lys Gly Arg Thr Tyr Tyr Val Asn His Asn Asn Arg Thr
145                 150                 155                 160

Thr Thr Trp Thr Arg Pro Ile Met Gln Leu Ala Glu Asp Gly Ala Ser
                165                 170                 175

Gly Ser Ala Thr Asn Ser Asn Asn His Leu Ile Glu Pro Gln Ile Arg
            180                 185                 190
```

```
Arg Pro Arg Ser Leu Ser Ser Pro Thr Val Thr Leu Ser Ala Pro Leu
            195                 200                 205

Glu Gly Ala Lys Asp Ser Pro Val Arg Arg Ala Val Lys Asp Thr Leu
            210                 215                 220

Ser Asn Pro Gln Ser Pro Gln Pro Ser Pro Tyr Asn Ser Pro Lys Pro
225                 230                 235                 240

Gln His Lys Val Thr Gln Ser Phe Leu Pro Pro Gly Trp Glu Met Arg
                245                 250                 255

Ile Ala Pro Asn Gly Arg Pro Phe Phe Ile Asp His Asn Thr Lys Thr
            260                 265                 270

Thr Thr Trp Glu Asp Pro Arg Leu Lys Phe Pro Val His Met Arg Ser
            275                 280                 285

Lys Thr Ser Leu Asn Pro Asn Asp Leu Gly Pro Leu Pro Pro Gly Trp
            290                 295                 300

Glu Glu Arg Ile His Leu Asp Gly Arg Thr Phe Tyr Ile Asp His Asn
305                 310                 315                 320

Ser Lys Ile Thr Gln Trp Glu Asp Pro Arg Leu Gln Asn Pro Ala Ile
                325                 330                 335

Thr Gly Pro Ala Val Pro Tyr Ser Arg Glu Phe Lys Gln Lys Tyr Asp
                340                 345                 350

Tyr Phe Arg Lys Lys Leu Lys Lys Pro Ala Asp Ile Pro Asn Arg Phe
            355                 360                 365

Glu Met Lys Leu His Arg Asn Asn Ile Phe Glu Glu Ser Tyr Arg Arg
            370                 375                 380

Ile Met Ser Val Lys Arg Pro Asp Val Leu Lys Ala Arg Leu Trp Ile
385                 390                 395                 400

Glu Phe Glu Ser Glu Lys Gly Leu Asp Tyr Gly Gly Val Ala Arg Glu
                405                 410                 415

Trp Phe Phe Leu Leu Ser Lys Glu Met Phe Asn Pro Tyr Tyr Gly Leu
            420                 425                 430

Phe Glu Tyr Ser Ala Thr Asp Asn Tyr Thr Leu Gln Ile Asn Pro Asn
            435                 440                 445

Ser Gly Leu Cys Asn Glu Asp His Leu Ser Tyr Phe Thr Phe Ile Gly
450                 455                 460

Lys Val Ala Gly Leu Ala Val Phe His Gly Lys Leu Leu Asp Gly Phe
465                 470                 475                 480

Phe Ile Arg Pro Phe Tyr Lys Met Met Leu Gly Lys Gln Ile Thr Leu
                485                 490                 495

Asn Asp Met Glu Ser Val Asp Ser Glu Tyr Tyr Asn Ser Leu Lys Trp
            500                 505                 510

Ile Leu Glu Asn Asp Pro Thr Glu Leu Asp Leu Met Phe Cys Ile Asp
            515                 520                 525

Glu Glu Asn Phe Gly Gln Thr Tyr Gln Val Asp Leu Lys Pro Asn Gly
            530                 535                 540

Ser Glu Ile Met Val Thr Asn Glu Asn Lys Arg Glu Tyr Ile Asp Leu
545                 550                 555                 560

Val Ile Gln Trp Arg Phe Val Asn Arg Val Gln Lys Gln Met Asn Ala
                565                 570                 575

Phe Leu Glu Gly Phe Thr Glu Leu Leu Pro Ile Asp Leu Ile Lys Ile
            580                 585                 590

Phe Asp Glu Asn Glu Leu Glu Leu Leu Met Cys Gly Leu Gly Asp Val
            595                 600                 605
```

```
Asp Val Asn Asp Trp Arg Gln His Ser Ile Tyr Lys Asn Gly Tyr Cys
    610                 615                 620

Pro Asn His Pro Val Ile Gln Trp Phe Trp Lys Ala Val Leu Leu Met
625                 630                 635                 640

Asp Ala Glu Lys Arg Ile Arg Leu Leu Gln Phe Val Thr Gly Thr Ser
                645                 650                 655

Arg Val Pro Met Asn Gly Phe Ala Glu Leu Tyr Gly Ser Asn Gly Pro
                660                 665                 670

Gln Leu Phe Thr Ile Glu Gln Trp Gly Ser Pro Glu Lys Leu Pro Lys
                675                 680                 685

Ala His Thr Cys Phe Asn Arg Leu Asp Leu Pro Pro Tyr Glu Thr Phe
                690                 695                 700

Glu Asp Leu Gln Glu Lys Leu Leu Met Ala Val Glu Asn Ala Gln Gly
705                 710                 715                 720

Phe Glu Gly Val Asp
                725

(2) INFORMATION FOR SEQ ID NO: 127:

(i) SEQUENCE CHARACTERISTICS:
        (A) LENGTH: 26 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 127:

Trp Glu Glu Arg Lys Asp Ala Lys Gly Arg Thr Tyr Tyr Val Asn His
1               5                   10                  15

Asn Asn Arg Thr Thr Thr Trp Thr Arg Pro
                20                  25

(2) INFORMATION FOR SEQ ID NO: 128:

(i) SEQUENCE CHARACTERISTICS:
        (A) LENGTH: 26 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 128:

Trp Glu Met Arg Ile Ala Pro Asn Gly Arg Pro Phe Phe Ile Asp His
1               5                   10                  15

Asn Thr Lys Thr Thr Thr Trp Glu Asp Pro
                20                  25

(2) INFORMATION FOR SEQ ID NO: 129:

(i) SEQUENCE CHARACTERISTICS:
        (A) LENGTH: 26 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 129:

Trp Glu Glu Arg Ile His Leu Asp Gly Arg Thr Phe Tyr Ile Asp His
1               5                   10                  15

Asn Ser Lys Ile Thr Gln Trp Glu Asp Pro
```

(2) INFORMATION FOR SEQ ID NO: 130:

(i) SEQUENCE CHARACTERISTICS:
        (A) LENGTH: 107 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 130:

```
Tyr Lys Asn Gly Tyr Cys Pro Asn His Pro Val Ile Gln Trp Phe Trp
 1               5                  10                  15

Lys Ala Val Leu Leu Met Asp Ala Glu Lys Arg Ile Arg Leu Leu Gln
            20                  25                  30

Phe Val Thr Gly Thr Ser Arg Val Pro Met Asn Gly Phe Ala Glu Leu
        35                  40                  45

Tyr Gly Ser Asn Gly Pro Gln Leu Phe Thr Ile Glu Gln Trp Gly Ser
    50                  55                  60

Pro Glu Lys Leu Pro Lys Ala His Thr Cys Phe Asn Arg Leu Asp Leu
65                  70                  75                  80

Pro Pro Tyr Glu Thr Phe Glu Asp Leu Gln Glu Lys Leu Leu Met Ala
                85                  90                  95

Val Glu Asn Ala Gln Gly Phe Glu Gly Val Asp
                100                 105
```

(2) INFORMATION FOR SEQ ID NO: 131:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 131:

```
Gln Pro Leu Pro Pro Gly Trp Glu Arg Arg Val Asp Asp Arg Arg Arg
 1               5                  10                  15

Val Tyr Tyr Val Asp His Asn Thr Arg Thr Thr Thr Trp Gln Arg Pro
            20                  25                  30

Thr Met Glu Ser Val Arg
        35
```

(2) INFORMATION FOR SEQ ID NO: 132:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 132:

```
Pro Gly Leu Pro Ser Gly Trp Glu Glu Arg Lys Asp Ala Lys Gly Arg
 1               5                  10                  15

Thr Tyr Tyr Val Asn His Asn Asn Arg Thr Thr Thr Trp Thr Arg Pro
            20                  25                  30

Ile Met Gln Leu Ala Glu
        35
```

(2) INFORMATION FOR SEQ ID NO: 133:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 133:

Ser Phe Leu Pro Pro Gly Trp Glu Met Arg Ile Ala Pro Asn Gly Arg
1               5                   10                  15

Pro Phe Phe Ile Asp His Asn Thr Lys Thr Thr Thr Trp Glu Asp Pro
            20                  25                  30

Arg Leu Lys Phe Pro Val
            35

(2) INFORMATION FOR SEQ ID NO: 134:

(i) SEQUENCE CHARACTERISTICS:
        (A) LENGTH: 38 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 134:

Gly Pro Leu Pro Pro Gly Trp Glu Glu Arg Ile His Leu Asp Gly Arg
1               5                   10                  15

Thr Phe Tyr Ile Asp His Asn Ser Lys Ile Thr Gln Trp Glu Asp Pro
            20                  25                  30

Arg Leu Gln Asn Pro Ala
            35

(2) INFORMATION FOR SEQ ID NO: 135:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 135:

Thr Ser Gln Pro Pro Pro Pro Pro Tyr Tyr Pro Pro
1               5                   10

(2) INFORMATION FOR SEQ ID NO: 136:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 136:

Tyr Val Gln Ala Pro Pro Pro Tyr Pro Gly Pro Met
1               5                   10

(2) INFORMATION FOR SEQ ID NO: 137:

```
    (i) SEQUENCE CHARACTERISTICS:
        (A) LENGTH: 13 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 137:

Tyr Val Gln Pro Ala Pro Pro Pro Tyr Pro Gly Pro Met
1               5                   10

(2) INFORMATION FOR SEQ ID NO: 138:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 138:

Tyr Val Gln Pro Pro Ala Pro Pro Tyr Pro Gly Pro Met
1               5                   10

(2) INFORMATION FOR SEQ ID NO: 139:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 139:

Tyr Val Gln Pro Pro Pro Ala Pro Tyr Pro Gly Pro Met
1               5                   10

(2) INFORMATION FOR SEQ ID NO: 140:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 140:

Tyr Val Gln Pro Pro Pro Pro Ala Tyr Pro Pro Gly Pro Met
1               5                   10

(2) INFORMATION FOR SEQ ID NO: 141:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 141:

Ala Pro Pro Thr Pro Pro Pro Leu Pro Pro
1               5                   10
```

-continued (2) INFORMATION FOR SEQ ID NO: 142:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 142:

```
Gln His Ser Pro Tyr Trp Ala Pro Pro Cys Tyr Thr Leu Lys Pro Glu
1               5                   10                  15
Thr
```

(2) INFORMATION FOR SEQ ID NO: 143:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 143:

```
Arg Asp Gly Asp Arg Asn Arg Pro Pro Val Tyr Gln Asp Leu Leu Pro
1               5                   10                  15
```

(2) INFORMATION FOR SEQ ID NO: 144:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 144:

```
Glu Lys Ala Pro Leu Pro Pro Pro Glu Tyr Pro Asn Gln Ser
1               5                   10
```

(2) INFORMATION FOR SEQ ID NO: 145:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 145:

```
Met Thr Pro Tyr Arg Ser Pro Pro Pro Tyr Val Pro Pro
1               5                   10
```

(2) INFORMATION FOR SEQ ID NO: 146:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 146:

```
Gly Val Ile Met Tyr Ile Leu Leu Cys Gly Tyr Pro Pro Phe Tyr Ser
```

```
                1               5              10              15
Asn His Gly Leu Ala
                       20

(2) INFORMATION FOR SEQ ID NO: 147:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 147:

Gly Val Leu Ile Tyr Glu Met Ala Val Gly Phe Pro Pro Phe Tyr Ala
1               5              10                          15
Asp Gln Pro Ile Gln
                       20

(2) INFORMATION FOR SEQ ID NO: 148:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 148:

Phe Arg Met Gln Ala Gln Pro Pro Gly Tyr Arg His Val Ala Asp
1               5              10                      15

(2) INFORMATION FOR SEQ ID NO: 149:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 149:

Pro Asp Ser Asp Pro Gln Ile Pro Pro Pro Tyr Val Glu Pro Thr Ala
1               5              10                          15

(2) INFORMATION FOR SEQ ID NO: 150:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 150:

Thr Ala Thr Ala Ser Ala Pro Pro Pro Pro Tyr Val Gly Ser Gly Leu
1               5              10                          15

(2) INFORMATION FOR SEQ ID NO: 151:

(i) SEQUENCE CHARACTERISTICS:
        (A) LENGTH: 16 amino acids
        (B) TYPE: amino acid
        (C) STRANDEDNESS: <Unknown>
```

```
            (D) TOPOLOGY: unknown (ii) MOLECULE TYPE: peptide (xi) SEQUENCE DESCRIPTION: SEQ ID NO: 151:

His Leu Tyr Ser Pro Pro Pro Pro Pro Tyr Ser Gly Cys Ala
1               5                   10              15

(2) INFORMATION FOR SEQ ID NO: 152:

(i) SEQUENCE CHARACTERISTICS:
            (A) LENGTH: 12 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 152:

Pro His Pro Gln Pro Pro Pro Tyr Gly His Cys Val
1               5                   10

(2) INFORMATION FOR SEQ ID NO: 153:

(i) SEQUENCE CHARACTERISTICS:
            (A) LENGTH: 12 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 153:

Pro Arg Arg Gly Pro Pro Thr Tyr Arg Ala Asp Asp
1               5                   10

(2) INFORMATION FOR SEQ ID NO: 154:

(i) SEQUENCE CHARACTERISTICS:
            (A) LENGTH: 12 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 154:

Pro Leu Glu Pro Pro Pro Leu Tyr Leu Met Glu Asp
1               5                   10

(2) INFORMATION FOR SEQ ID NO: 155:

(i) SEQUENCE CHARACTERISTICS:
            (A) LENGTH: 12 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 155:

Pro Pro Pro Ala Pro Pro Gln Tyr Pro Asp Phe Ser
1               5                   10

(2) INFORMATION FOR SEQ ID NO: 156:

(i) SEQUENCE CHARACTERISTICS:
            (A) LENGTH: 12 amino acids
            (B) TYPE: amino acid
```

```
            (C) STRANDEDNESS: <Unknown>
            (D) TOPOLOGY: unknown (ii) MOLECULE TYPE: peptide (xi) SEQUENCE DESCRIPTION: SEQ ID NO: 156:

Pro Asn Ser Asp Pro Pro Arg Tyr Gln Phe Leu Trp
1               5                   10

(2) INFORMATION FOR SEQ ID NO: 157:

(i) SEQUENCE CHARACTERISTICS:
            (A) LENGTH: 12 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 157:

Pro His Ser Leu Pro Pro Thr Tyr Tyr Asp Asn Ser
1               5                   10

(2) INFORMATION FOR SEQ ID NO: 158:

(i) SEQUENCE CHARACTERISTICS:
            (A) LENGTH: 13 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 158:

Ile Ala Pro Pro Pro Pro Pro Tyr Asn Asn Glu Thr
1               5                   10

(2) INFORMATION FOR SEQ ID NO: 159:

(i) SEQUENCE CHARACTERISTICS:
            (A) LENGTH: 13 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 159:

Ser Arg Gly Met Pro Ser Tyr Glu Glu Ala Val Met Ala
1               5                   10

(2) INFORMATION FOR SEQ ID NO: 160:

(i) SEQUENCE CHARACTERISTICS:
            (A) LENGTH: 14 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 160:

Pro Gly Thr Pro Pro Pro Pro Asn His Asp Ser Leu Arg Leu
1               5                   10

(2) INFORMATION FOR SEQ ID NO: 161:

(i) SEQUENCE CHARACTERISTICS:
            (A) LENGTH: 13 amino acids
```

```
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 161:

Pro Gly Thr Ala Pro Pro Asn Tyr Asp Ser Leu Arg Leu
1               5                   10

(2) INFORMATION FOR SEQ ID NO: 162:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 162:

Pro Gly Thr Pro Ala Pro Asn Tyr Asp Ser Leu Arg Leu
1               5                   10

(2) INFORMATION FOR SEQ ID NO: 163:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 163:

Pro Gly Thr Pro Pro Pro Asn Ala Asp Ser Leu Arg Leu
1               5                   10

(2) INFORMATION FOR SEQ ID NO: 164:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 164:

Pro Gly Thr Pro Pro Pro Asn Tyr Asp Ala Leu Arg Leu
1               5                   10

(2) INFORMATION FOR SEQ ID NO: 165:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 165:

Pro Gly Thr Pro Pro Pro Asn Tyr Asp Ser Ala Arg Leu
1               5                   10

(2) INFORMATION FOR SEQ ID NO: 166:

(i) SEQUENCE CHARACTERISTICS:
```

(A) LENGTH: 13 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 166:

Pro Gly Thr Pro Pro Pro Asn Tyr Asp Ser Glu Arg Leu
1               5                   10

(2) INFORMATION FOR SEQ ID NO: 167:

(i) SEQUENCE CHARACTERISTICS:
            (A) LENGTH: 13 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 167:

Pro Gly Thr Pro Pro Pro Lys Ala Asn Thr Leu Arg Leu
1               5                   10

(2) INFORMATION FOR SEQ ID NO: 168:

(i) SEQUENCE CHARACTERISTICS:
            (A) LENGTH: 13 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 168:

Leu Thr Ala Pro Pro Pro Ala Tyr Ala Thr Leu Gly Pro
1               5                   10

(2) INFORMATION FOR SEQ ID NO: 169:

(i) SEQUENCE CHARACTERISTICS:
            (A) LENGTH: 13 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 169:

Leu Thr Ala Pro Pro Pro Ala Ala Ala Thr Leu Gly Pro
1               5                   10

(2) INFORMATION FOR SEQ ID NO: 170:

(i) SEQUENCE CHARACTERISTICS:
            (A) LENGTH: 17 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 170:

Pro Pro Leu Ala Leu Thr Ala Pro Pro Ala Tyr Ala Thr Leu Gly
1               5                   10                  15

Pro (2) INFORMATION FOR SEQ ID NO: 171:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 171:

```
Pro Ser Pro Ala Leu Thr Ala Pro Pro Ala Tyr Ala Thr Leu Gly
1               5                  10                  15
Pro
```

(2) INFORMATION FOR SEQ ID NO: 172:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 172:

```
Pro Ser Pro Ala Leu Thr Ala Pro Pro Ala Ala Ala Thr Leu Gly
1               5                  10                  15
Pro
```

(2) INFORMATION FOR SEQ ID NO: 173:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 173:

```
Pro Ser Pro Ala Leu Thr Ala Pro Pro Ala Tyr
1               5                  10
```

(2) INFORMATION FOR SEQ ID NO: 174:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 174:

```
Gln His Ser Pro Tyr Trp Ala Pro Pro Cys Tyr Thr Leu Lys Pro Glu
1               5                  10                  15
Thr
```

(2) INFORMATION FOR SEQ ID NO: 175:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: unknown (ii) MOLECULE TYPE: peptide

```
        (xi) SEQUENCE DESCRIPTION: SEQ ID NO: 175:

Met Thr Pro Tyr Arg Ser Pro Pro Pro Tyr Val Pro Pro
1               5                   10

(2) INFORMATION FOR SEQ ID NO: 176:

(i) SEQUENCE CHARACTERISTICS:
            (A) LENGTH: 16 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 176:

Pro Asp Ser Asp Pro Gln Ile Pro Pro Pro Tyr Val Glu Pro Thr Ala
1               5                   10                  15

(2) INFORMATION FOR SEQ ID NO: 177:

(i) SEQUENCE CHARACTERISTICS:
            (A) LENGTH: 16 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 177:

Thr Ala Thr Ala Ser Ala Pro Pro Pro Tyr Val Gly Ser Gly Leu
1               5                   10                  15

(2) INFORMATION FOR SEQ ID NO: 178:

(i) SEQUENCE CHARACTERISTICS:
            (A) LENGTH: 10 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 178:

Ala Pro Pro Thr Pro Pro Pro Leu Pro Pro
1               5                   10

(2) INFORMATION FOR SEQ ID NO: 179:

(i) SEQUENCE CHARACTERISTICS:
            (A) LENGTH: 13 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 179:

Asn Arg Leu Asp Leu Pro Pro Tyr Lys Ser Tyr Glu Gln
1               5                   10

(2) INFORMATION FOR SEQ ID NO: 180:

(i) SEQUENCE CHARACTERISTICS:
            (A) LENGTH: 13 amino acids
            (B) TYPE: amino acid
            (C) STRANDEDNESS: <Unknown>
            (D) TOPOLOGY: unknown
```

(ii) MOLECULE TYPE: peptide (xi) SEQUENCE DESCRIPTION: SEQ ID NO: 180:

Asn Arg Leu Asp Leu Pro Pro Ala Lys Ser Tyr Glu Gln
1               5                   10

(2) INFORMATION FOR SEQ ID NO: 181:

(i) SEQUENCE CHARACTERISTICS:
            (A) LENGTH: 13 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 181:

Asn Arg Leu Asp Leu Pro Pro Tyr Glu Thr Phe Glu Asp
1               5                   10

(2) INFORMATION FOR SEQ ID NO: 182:

(i) SEQUENCE CHARACTERISTICS:
            (A) LENGTH: 13 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 182:

Asn Arg Leu Asp Leu Pro Pro Ala Glu Thr Phe Glu Asp
1               5                   10

(2) INFORMATION FOR SEQ ID NO: 183:

(i) SEQUENCE CHARACTERISTICS:
            (A) LENGTH: 12 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 183:

Gly Leu Pro Pro Pro Tyr Asp Leu Thr Trp Val Asn
1               5                   10

(2) INFORMATION FOR SEQ ID NO: 184:

(i) SEQUENCE CHARACTERISTICS:
            (A) LENGTH: 12 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 184:

Gly Asp Val Arg Phe Trp Gly Ala Pro Pro Pro Tyr
1               5                   10

(2) INFORMATION FOR SEQ ID NO: 185:

(i) SEQUENCE CHARACTERISTICS:
            (A) LENGTH: 12 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 185:

Leu Lys Leu Pro Asp Tyr Trp Glu Ser Ser Ala Ser
1               5                   10

(2) INFORMATION FOR SEQ ID NO: 186:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 186:

Leu Lys Leu Pro Glu Tyr Trp Glu Ser Ser Ala Ser
1               5                   10

(2) INFORMATION FOR SEQ ID NO: 187:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 187:

Arg Ser Glu Arg Gly Val Pro Pro Thr Tyr Ala Glu Phe Phe Pro Met
1               5                   10                  15

(2) INFORMATION FOR SEQ ID NO: 188:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 188:

Asn Trp Pro His Val Met Pro Pro Tyr Ala Gln Tyr Arg
1               5                   10

(2) INFORMATION FOR SEQ ID NO: 189:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 189:

Gly Ala His Asp Ser Pro Pro Tyr Ser Arg Tyr Trp Pro
1               5                   10

(2) INFORMATION FOR SEQ ID NO: 190:

(i) SEQUENCE CHARACTERISTICS:
        (A) LENGTH: 14 amino acids
        (B) TYPE: amino acid
        (C) STRANDEDNESS: <Unknown>

```
            (D) TOPOLOGY: unknown (ii) MOLECULE TYPE: peptide (xi) SEQUENCE DESCRIPTION: SEQ ID NO: 190:

Gly Pro Ser Glu Gln Pro Pro Pro Tyr Glu Tyr Thr Val Lys
1               5                   10

(2) INFORMATION FOR SEQ ID NO: 191:

(i) SEQUENCE CHARACTERISTICS:
            (A) LENGTH: 16 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 191:

Ser Arg Ile Lys Gly Asp Pro Pro Gly Tyr Glu Glu Val Met Gly Leu
1               5                   10                  15

(2) INFORMATION FOR SEQ ID NO: 192:

(i) SEQUENCE CHARACTERISTICS:
            (A) LENGTH: 16 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 192:

Gln Thr Asp Tyr Tyr Pro Pro Gly Tyr Pro Trp Trp Glu Ser Arg
1               5                   10                  15

(2) INFORMATION FOR SEQ ID NO: 193:

(i) SEQUENCE CHARACTERISTICS:
            (A) LENGTH: 16 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 193:

Gly Val Glu Phe Gly Pro Pro Asp Tyr Glu Ala Leu Phe Lys Pro
1               5                   10                  15

(2) INFORMATION FOR SEQ ID NO: 194:

(i) SEQUENCE CHARACTERISTICS:
            (A) LENGTH: 12 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 194:

Met Leu Pro Glu Tyr Thr Glu Tyr Gly Phe Ser Met
1               5                   10

(2) INFORMATION FOR SEQ ID NO: 195:

(i) SEQUENCE CHARACTERISTICS:
            (A) LENGTH: 12 amino acids
            (B) TYPE: amino acid
```

```
        (C) STRANDEDNESS: <Unknown>
        (D) TOPOLOGY: unknown (ii) MOLECULE TYPE: peptide (xi) SEQUENCE DESCRIPTION: SEQ ID NO: 195:

Thr Leu Leu Pro Gly Tyr Leu Ser Asp Glu Tyr Trp
1               5                   10

(2) INFORMATION FOR SEQ ID NO: 196:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 196:

Leu Lys Leu Pro Asp Tyr Trp Glu Ser Ser Ala Ser
1               5                   10

(2) INFORMATION FOR SEQ ID NO: 197:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 197:

Leu Leu Pro Asn Tyr Gly Glu Trp Trp Arg Gly Gly
1               5                   10

(2) INFORMATION FOR SEQ ID NO: 198:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 198:

Ser Leu Leu Pro Thr Tyr Gly His Glu Leu Phe Trp
1               5                   10

(2) INFORMATION FOR SEQ ID NO: 199:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 199:

Ser Leu Leu Pro Glu Tyr Asn Met Pro Leu Tyr His
1               5                   10

(2) INFORMATION FOR SEQ ID NO: 200:

(i) SEQUENCE CHARACTERISTICS:
        (A) LENGTH: 12 amino acids
```

```
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 200:

Leu Met Leu Pro Ala Tyr Asn Glu Ala Val Thr Trp
1               5                   10

(2) INFORMATION FOR SEQ ID NO: 201:

(i) SEQUENCE CHARACTERISTICS:
            (A) LENGTH: 12 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 201:

Leu Met Leu Pro His Tyr Gly Asp Met Gln Phe Ala
1               5                   10

(2) INFORMATION FOR SEQ ID NO: 202:

(i) SEQUENCE CHARACTERISTICS:
            (A) LENGTH: 12 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 202:

Leu Leu Pro Met Tyr Gly Glu Ala Glu Ala Trp Phe
1               5                   10

(2) INFORMATION FOR SEQ ID NO: 203:

(i) SEQUENCE CHARACTERISTICS:
            (A) LENGTH: 14 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 203:

Gln Leu Pro Ile Ser Pro Pro Tyr Ser Glu Met Gly Leu
1               5                   10

(2) INFORMATION FOR SEQ ID NO: 204:

(i) SEQUENCE CHARACTERISTICS:
            (A) LENGTH: 14 amino acids
            (B) TYPE: amino acid
            (C) STRANDEDNESS: <Unknown>
            (D) TOPOLOGY: unknown (ii) MOLECULE TYPE: peptide (xi) SEQUENCE DESCRIPTION: SEQ ID NO: 204:

Gly Trp Thr Leu Gly Asp Pro Pro Tyr His Ile Ala Gly
1               5                   10

(2) INFORMATION FOR SEQ ID NO: 205:

(i) SEQUENCE CHARACTERISTICS:
```

(A) LENGTH: 14 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 205:

Arg Gly Gly Val Trp Leu Pro Pro Tyr Ser Ser Ile Asp Asn
1               5                   10

(2) INFORMATION FOR SEQ ID NO: 206:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 206:

His Lys Pro Leu Thr Pro Pro Tyr Asp Ala His Asp Phe
1               5                   10

(2) INFORMATION FOR SEQ ID NO: 207:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 207:

Leu Phe Trp Gln Val Gly Pro Pro Ser Tyr Glu Glu Ala Ile
1               5                   10

(2) INFORMATION FOR SEQ ID NO: 208:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 208:

Pro Ser Met Leu Thr Pro Pro Tyr Phe Glu His Lys Gln Asp Glu
1               5                   10                  15

(2) INFORMATION FOR SEQ ID NO: 209:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 209:

Trp Ser Met Lys Thr Ser Pro Pro Ser Tyr Glu Ser Ile Phe Gly Leu
1               5                   10                  15

(2) INFORMATION FOR SEQ ID NO: 210:

```
        (i) SEQUENCE CHARACTERISTICS:
              (A) LENGTH: 16 amino acids
              (B) TYPE: amino acid
              (C) STRANDEDNESS: <Unknown>
              (D) TOPOLOGY: unknown (ii) MOLECULE TYPE: peptide (xi) SEQUENCE DESCRIPTION: SEQ ID NO: 210:

Ala Val His Ser Leu Thr Leu Pro Ala Tyr Glu Ala Thr Glu Tyr Met
1               5                   10                  15

(2) INFORMATION FOR SEQ ID NO: 211:

(i) SEQUENCE CHARACTERISTICS:
              (A) LENGTH: 16 amino acids
              (B) TYPE: amino acid
              (C) STRANDEDNESS: <Unknown>
              (D) TOPOLOGY: unknown (ii) MOLECULE TYPE: peptide (xi) SEQUENCE DESCRIPTION: SEQ ID NO: 211:

Gly Arg Val Val Ser His Pro Pro Ala Tyr Cys Glu Leu Phe Lys Cys
1               5                   10                  15

(2) INFORMATION FOR SEQ ID NO: 212:

(i) SEQUENCE CHARACTERISTICS:
              (A) LENGTH: 16 amino acids
              (B) TYPE: amino acid
              (C) STRANDEDNESS: <Unknown>
              (D) TOPOLOGY: unknown (ii) MOLECULE TYPE: peptide (xi) SEQUENCE DESCRIPTION: SEQ ID NO: 212:

Ser Gly Arg Met Gln Gly Pro Pro Glu Tyr Gly Asp Met Glu Tyr Val
1               5                   10                  15

(2) INFORMATION FOR SEQ ID NO: 213:

(i) SEQUENCE CHARACTERISTICS:
              (A) LENGTH: 12 amino acids
              (B) TYPE: amino acid
              (C) STRANDEDNESS: <Unknown>
              (D) TOPOLOGY: unknown (ii) MOLECULE TYPE: peptide (xi) SEQUENCE DESCRIPTION: SEQ ID NO: 213:

Gly Met Leu Pro Ser Tyr Glu Glu Ala Val Met Ala
1               5                   10

(2) INFORMATION FOR SEQ ID NO: 214:

(i) SEQUENCE CHARACTERISTICS:
              (A) LENGTH: 12 amino acids
              (B) TYPE: amino acid
              (C) STRANDEDNESS: <Unknown>
              (D) TOPOLOGY: unknown (ii) MOLECULE TYPE: peptide (xi) SEQUENCE DESCRIPTION: SEQ ID NO: 214:

Pro Ile Ala Pro Pro Thr Tyr Trp Glu Trp Ala Leu
1               5                   10

(2) INFORMATION FOR SEQ ID NO: 215:
```

```
    (i) SEQUENCE CHARACTERISTICS:
        (A) LENGTH: 12 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 215:

Arg Leu Pro Ala Tyr Lys Glu Pro Ala Ala Thr Phe
1               5                   10

(2) INFORMATION FOR SEQ ID NO: 216:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 216:

Leu Pro Ser Tyr Ser Glu Trp Val Ala Glu Thr Arg
1               5                   10

(2) INFORMATION FOR SEQ ID NO: 217:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 217:

Leu Pro Thr Tyr Asn Glu Tyr Leu Thr Arg Ala Ala
1               5                   10

(2) INFORMATION FOR SEQ ID NO: 218:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 218:

Arg Val Tyr Arg Asp Leu Pro Pro Tyr Pro Gln Gly Thr
1               5                   10

(2) INFORMATION FOR SEQ ID NO: 219:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 219:

His Arg Ser Glu Leu Pro Pro Tyr Ser Glu Ala Val Lys
1               5                   10
```

(2) INFORMATION FOR SEQ ID NO: 220:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 220:

```
Gly Gly Trp Arg Ala Val Pro Pro Pro Tyr Pro Gly Ser Pro
1               5                   10
```

(2) INFORMATION FOR SEQ ID NO: 221:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 221:

```
Leu Met Arg Arg Ala Pro Pro Pro Tyr Pro Gln Val Ala
1               5                   10
```

(2) INFORMATION FOR SEQ ID NO: 222:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 222:

```
Arg Leu Tyr Thr Thr Pro Pro Pro Tyr Ala Ser Leu His Lys
1               5                   10
```

(2) INFORMATION FOR SEQ ID NO: 223:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 223:

```
Pro Met His Arg Val Gly Pro Pro Pro Tyr Pro Gly Leu
1               5                   10
```

(2) INFORMATION FOR SEQ ID NO: 224:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 224:

```
Pro Trp Leu Arg Gly Asp Pro Pro Tyr Met Glu Leu Val Ser Glu
1               5                   10                  15
```

(2) INFORMATION FOR SEQ ID NO: 225:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 225:

```
Gly Ser Trp Glu Thr Pro Pro Pro Ser Tyr Glu Glu Trp Leu Arg Lys
1               5                   10                  15
```

(2) INFORMATION FOR SEQ ID NO: 226:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 226:

```
Ala His Met Tyr Arg Pro Pro Pro Tyr Arg Gly Ser Ser Asp Gly
1               5                   10                  15
```

(2) INFORMATION FOR SEQ ID NO: 227:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 227:

```
Gly Arg Phe Leu Arg Glu Pro Pro Tyr Pro Asn Arg Asp Val Ala
1               5                   10                  15
```

(2) INFORMATION FOR SEQ ID NO: 228:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 228:

```
Val Ala Met Arg Asp Pro Pro Pro Tyr Asn Tyr Val Asp Ala Pro
1               5                   10                  15
```

(2) INFORMATION FOR SEQ ID NO: 229:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 229:

Val Ala Thr Leu Arg Pro Pro Ala Tyr Gly Val Glu Tyr Ser Arg
1               5                   10                  15

(2) INFORMATION FOR SEQ ID NO: 230:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 230:

Met Leu Lys Asp Val Ala Pro Pro Ala Tyr Glu Glu Ala Val Arg Arg
1               5                   10                  15

(2) INFORMATION FOR SEQ ID NO: 231:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 231:

Pro Pro Pro Asn Tyr
1               5

(2) INFORMATION FOR SEQ ID NO: 232:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 232:

Pro Pro Leu Asn Tyr
1               5

(2) INFORMATION FOR SEQ ID NO: 233:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 233:

Pro Pro Pro Asn His
1               5